(12) United States Patent
Sit et al.

(10) Patent No.: US 6,562,846 B2
(45) Date of Patent: May 13, 2003

(54) BISARYLIMIDAZOLYL FATTY ACID AMIDE HYDROLASE INHIBITORS

(75) Inventors: Sing-Yuen Sit, Meriden, CT (US); Kai Xie, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/128,480

(22) Filed: Apr. 23, 2002

(65) Prior Publication Data

US 2002/0188009 A1 Dec. 12, 2002

Related U.S. Application Data

(60) Provisional application No. 60/286,827, filed on Apr. 27, 2001.

(51) Int. Cl.[7] ................ A61K 31/4164; A61K 31/4439; C07D 233/64; C07D 401/12
(52) U.S. Cl. .................... 514/341; 514/399; 546/275.1; 548/338.1; 548/341.5; 548/336.1
(58) Field of Search ........................... 548/338.1, 341.5, 548/336.1; 546/275.1; 514/341, 399

(56) References Cited

U.S. PATENT DOCUMENTS 5,648,373 A * 7/1997 Winkler et al. ............. 514/398

OTHER PUBLICATIONS

Levine, "New Directions in Pain Research: Molecules to Maladies," Neuron, vol. 20, pp. 649–654, Apr. 1998.
Pasternak, "The Central Questions in Pain Perception May Be Peripheral," Proc. Natl. Acad. Sci., USA, vol. 95, pp. 10354–10355, Sep. 1998.
Hanus, et al., "Two New Unsatured Fatty Acid Ethanolamides in Brian That bind to the Cannabinoid Receptor," J. Med. Chem., vol. 36, pp. 3032–3034, 1993.
Mechoulam, et al., "Identification of an Endogenous 2–Monoglyceride, Present in Canine Gut, That Binds to Cannabinoid Receptors," Biochem. Pharmacol., vol. 50, No. 1, pp. 83–90, 1995.
Barg, et al., "Cannabinomimetic Behavioral Effects of and Adenylate Cyclase Inhibition by Two New Endogenous Anandamides," European Journal of Pharmacology, vol. 287, pp. 145–152, 1995.
Richardson, et al., "Cannabinoids Reduce Hyperalgesia and Inflammation Via Interaction with Peripheral CB1 Receptors," Pain, vol. 75, pp. 111–119, 1998.
Jaggar, et al., "The Anti–hyperalgesic Actions of the Cannabiniod Anandamide and the Putative CB2 Receptor Agonist Palmitoylethanolamide in Visceral and Somatic Inflammatory Pain," Pain, vol. 76, pp. 189–199, 1998.
Huang, et al., "Identification of New Class of Molecules, the Arachidonyl Amide Acids, and Characterization of One Member That Inhibits Pain," Journal of Biological Chemistry, vol. 276, No. 46, pp. 42639–42644, 2001.
Richardson, et al., "Hypoactivity of the Spinal Cannabinoid System Results in NMDA–Dependent Hyperalgesia," Journal of Neuroscience, vol. 18, No., pp. 451–457, 1998.
Meanwell et al., J. Med. Chem., 1992, vol. 35, pp. 3498–3512.*

* cited by examiner

*Primary Examiner*—Laura L. Stockton
(74) *Attorney, Agent, or Firm*—Shah R. Makujina

(57) ABSTRACT

The present invention relates to bisarylimidazolyl derivatives and pharmaceutical compositions comprising said compounds inhibiting fatty acid amide hydrolase and useful for the treatment of pain, particularly neuropathic pain, psychomotor disorder, hypertension, cardiovascular disease, eating disorder, nausea, AIDS-related complex, glaucoma, inflammation, psoriasis or multiple sclerosis, and other conditions the treatment of which can be effected by inhibiting fatty acid amide hydrolase.

20 Claims, 3 Drawing Sheets

BISARYLIMIDAZOLYL FATTY ACID AMIDE HYDROLASE INHIBITORS

CROSS REFERENCE TO RELATED APPLICATION

This non-provisional application claims priority from provisional application U.S. Ser. No. 60/286,827 filed Apr. 27, 2001.

FIELD OF THE INVENTION

The present invention relates to bisarylimidazolyl derivatives and pharmaceutical compositions comprising said derivatives which inhibit fatty acid amide hydrolase and are useful for the treatment of conditions affected by inhibiting fatty acid amide hydrolase.

BACKGROUND

Neuropathic pain is caused by injury to nerves as the result of many factors including physical damage (e.g., trauma, surgery), drugs such as Zidovudine (AZT), Carmustine (BCNU) and disease (e.g., diabetes, herpes zoster). The prevalence in the United States of neuropathies associated with diabetes, herpes and amputation is estimated at 1.5 million. The worldwide prevalence of diabetic neuropathy alone is expected to reach 12 million by 2007. Nerve injury can result in both allodynia and hyperalgesia.

Current treatment of neuropathic pain involves the use of non-steroidal anti-inflammatory drugs (NSAIDs) such as aspirin and acetaminophen) and other analgesics as well as anticonvulsants (e.g., carbamazepine, gabapentin) and tricyclic antidepressants (e.g., amitryptiline). Effective treatment of pain with current therapies is limited by adverse effects and a lack of efficacy against all components of pain.

Current research is aimed at understanding the molecular and physiological components of pain processing to develop more effective analgesics (Levine, J. D., New Directions in Pain Research: Meeting Report Molecules to Maladies, *Neuron* 20: 649–654, 1998; Pasternak, G. W., The Central Questions in Pain Perception May Be Peripheral, *PNAS* 95:10354–10355, 1998).

The analgesic properties of cannabinoids have been known for many years and to many cultures. Cannabinoids are active in many pre-clinical models of pain, including neuropathic pain. Within the last few years, several endogenous cannabinoids, including the fatty acid amides arachidonylethanolamide (anandamide), and arachidonyl amino acids such as N-arachidonylglycine, homo-γ-linolenyl-ethanolamide and docosatetraenyl-ethanolamide, as well as 2-arachidonyl-glycerol, have been shown to induce analgesia in laboratory animals (DeVane, W. A. et. al., Isolation and Structure of a Brain Constituent That Binds to the Cannabinoid Receptors, *Science* 258: 1946–1949, 1992; Hanus, L. et. al., Two New Unsaturated Fatty Acid Ethanolamides in Brain that Bind to the Cannabinoid Receptor, *J. Med. Chem.* 36: 3032–3034, 1993; Machoulam, R. et. al., Identification of an Endogenous 2-Monoglyceride, Present in Canine Gut, That Binds To Cannabinoid Receptors, *Biochem. Pharmacol.* 50: 83–90, 1995; Vogel, Z. et. al., Cannabinomimetic Behavioral Effects of and Adenylate Cyclase Inhibition By Two New Endogenous Anandamides, *Eur. J. Pharmacol.* 287: 145–152, 1995; Hargreaves, K. M. et al., Cannabinoids Reduce Hyperalgesia and Inflammation Via Interaction With Peripheral CB1 Receptors, *Pain* 75: 111–119, 1998; Rice, A. S. C., et. al., The Anti-Hyperalgesic Actions of the Cannabinoid Anandamide and the Putative CB2 Receptor Agonist Palmitoylethanolamide in Visceral and Somatic Inflammatory Pain, *Pain* 76: 189–199, 1998; Huang, S. M., et al., Identification of a New Class of Molecules, the Arachidonyl Amino Acids, and Characterization of One Member That Inhibits Pain, *J. Biological Chemistry*, 276: 46, 42639–42644, 2001). The ability of cannabinoid receptor antagonists and cannabinoid receptor antisense to induce hyperalgesia in animals suggests that endogenous cannabinoids regulate the nociceptive threshold (Hargreaves, K. M. et al., Hypoactivity of the Spinal Cannabinoid System Results in NMDA-Dependent Hyperalgesia, *J. Neurosci.* 18: 451–457, 1998; Piomelli, D. et. al., Control of Pain Initiation By Endogenous Cannabinoids, *Nature* 394: 277–281, 1998; Fields, H. L. et. al., An Analgesia Circuit Activated By Cannabinoids, *Nature* 395: 381–383, 1998). Elevation of levels of neuroactive fatty acid amides such as anandamide may provide a unique mechanism to achieve analgesia. The mechanisms by which endogenous cannabinoids are synthesized are not well understood; therefore, targets for drugs aimed at increasing the synthesis of these compounds are slow to be identified.

Anandamide and the other identified endogenous cannabinoids are inactivated through a cleavage mechanism by a membrane-bound enzyme, fatty acid amide hydrolase (FAAH). FAAH, therefore, provides an important target for regulating the activity of endogenous cannabinoids. The inhibition of FAAH may elevate levels of anandamide or other endogenous cannabinoids to increase the nociceptive threshold. Furthermore, the inhibition of FAAH would also extend the therapeutic benefits of other cannabinoid agonists in the treatment of emesis, anxiety, feeding behaviors, movement disorders, glaucoma, neuroprotection and cardiovascular disease.

SUMMARY OF THE INVENTION

Thus according to a first embodiment of the first aspect of the present invention are provided compounds of Formula (I)

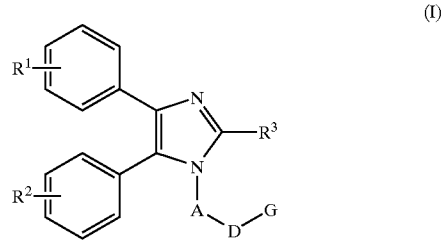

and pharmaceutically acceptable salts and solvates thereof wherein $R^1$ are $R^2$ are each independently H, $C_{1-3}$alkyl or halo;

$R^3$ is $C_1$–$C_3$alkyl or $C_{3-7}$cycloalkyl;

A is $C_{1-12}$alkylene or L;

L is -phenyl-O—$C_{1-4}$alkylene wherein said $C_{1-4}$alkylene is attached to D;

provided that if A is L, then D is X(O)O and A—D is not interrupted with J—J', —Z-phenyl- or —Z—$C_{1-3}$alkylene;

D is X(O)O, X(O)N(G'), HYC(O)O or HYC(O)ON=C (G');

X is C and is attached to A;

Y is N and is attached to A;

G is H, $C_{1-5}$alkyl, $C_{1-5}$haloalkyl, $C_{3-7}$cycloalkyl, phenyl, —$C_{1-2}$alkylene-phenyl, C-pyridyl or N-pyridyl, said phenyl or —C$_{1-2}$alkylene-phenyl are each optionally and independently substituted with one or more of the same or different substituents selected from the group consisting of halo, NO$_2$, CN, —C(O)O—C$_{1-3}$-alkyl, C$_{1-3}$alkyl, hydroxy and C$_{1-3}$alkoxy;

G' is H, C$_{1-5}$alkyl or C$_{1-5}$haloalkyl;

wherein A—D is optionally interrupted with J—J', —Z-phenyl- or —Z—C$_{1-3}$alkylene;

wherein

Z is O or S and is attached to A;

J is CH and is attached to A, D and J';

J' is C$_{1-4}$alkyl or phenyl; and provided that if A—D is interrpted with —Z-phenyl-, then A is C$_{1-5}$alkylene;

if A—D is not interrpted with —Z-phenyl-, then A is C$_{5-12}$alkylene.

According to another embodiment of the first aspect of the present invention are provided compounds of Formula (I) according to the first embodiment of the first aspect wherein R$^1$ and R$^2$ are each H.

According to another embodiment of the first aspect of the present invention are provided compounds of Formula (I) according to the first embodiment of the first aspect wherein R$^1$ and R$^2$ are each halo.

According to another embodiment of the first aspect of the present invention are provided compounds of Formula (I) according to the first embodiment of the first aspect wherein R$^1$ and R$^2$ are each fluoro.

According to another embodiment of the first aspect of the present invention are provided compounds of Formula (I) according to the first embodiment of the first aspect wherein R$^3$ is methyl.

According to another embodiment of the first aspect of the present invention are provided compounds of Formula (I) according to the first embodiment of the first aspect wherein R$^3$ is ethyl.

According to another embodiment of the first aspect of the present invention are provided compounds of Formula (I) according to the first embodiment of the first aspect wherein A is L.

According to another embodiment of the first aspect of the present invention are provided compounds of Formula (I) according to the first embodiment of the first aspect wherein A is C$_{3-10}$alkylene.

According to another embodiment of the first aspect of the present invention are provided compounds of Formula (I) according to the first embodiment of the first aspect wherein A is C$_{7-10}$alkylene.

According to another embodiment of the first aspect of the present invention are provided compounds of Formula (I) according to the first embodiment of the first aspect wherein A is C$_{4-8}$alkylene.

According to another embodiment of the first aspect of the present invention are provided compounds of Formula (I) according to the first embodiment of the first aspect wherein A is C$_{5-7}$alkylene.

According to another embodiment of the first aspect of the present invention are provided compounds of Formula (I) according to the first embodiment of the first aspect wherein A is C$_{8-9}$alkylene.

According to another embodiment of the first aspect of the present invention are provided compounds of Formula (I) according to the first embodiment of the first aspect wherein A is C$_9$alkylene.

According to another embodiment of the first aspect of the present invention are provided compounds of Formula (I) according to the first embodiment of the first aspect wherein A is C$_6$alkylene.

According to another embodiment of the first aspect of the present invention are provided compounds of Formula (I) according to the first embodiment of the first aspect wherein A is C$_{1-4}$alkylene.

According to another embodiment of the first aspect of the present invention are provided compounds of Formula (I) according to the first embodiment of the first aspect wherein D is X(O)O.

According to another embodiment of the first aspect of the present invention are provided compounds of Formula (I) according to the first embodiment of the first aspect wherein D is X(O)N(G').

According to another embodiment of the first aspect of the present invention are provided compounds of Formula (I) according to the first embodiment of the first aspect wherein D is HYC(O)O.

According to another embodiment of the first aspect of the present invention are provided compounds of Formula (I) according to the first embodiment of the first aspect wherein D is HYC(O)ON=C(G').

According to another embodiment of the first aspect of the present invention are provided compounds of Formula (I) according to the first embodiment of the first aspect wherein G is C$_{1-5}$alkyl.

According to another embodiment of the first aspect of the present invention are provided compounds of Formula (I) according to the first embodiment of the first aspect wherein G is C$_{3-7}$cycloalkyl.

According to another embodiment of the first aspect of the present invention are provided compounds of Formula (I) according to the first embodiment of the first aspect wherein G is —C$_{1-2}$alkylene-phenyl.

According to another embodiment of the first aspect of the present invention are provided compounds of Formula (I) according to the first embodiment of the first aspect wherein G is phenyl or —C$_{1-2}$alkylene-phenyl, said phenyl or phenyl of said —C$_{1-2}$alkylene-phenyl are optionally substituted with the same or different substituents selected from the group consisting of halo, CN, —C(O)O—C$_{1-3}$-alkyl, C$_{1-3}$alkyl and C$_{1-3}$alkoxy.

According to another embodiment of the first aspect of the present invention are provided compounds of Formula (I) according to the first embodiment of the first aspect wherein G is phenyl or —C$_{1-2}$alkylene-phenyl, said phenyl or phenyl of said —C$_{1-2}$alkylene-phenyl are substituted with halo, —C(O)O—C$_{1-3}$-alkyl, C$_{1-3}$alkyl or C$_{1-3}$alkoxy.

According to another embodiment of the first aspect of the present invention are provided compounds of Formula (I) according to the first embodiment of the first aspect wherein G is phenyl or —C$_{1-2}$alkylene-phenyl, said phenyl or phenyl of said —C$_{1-2}$alkylene-phenyl are substituted with fluoro.

According to another embodiment of the first aspect of the present invention are provided compounds of Formula (I) according to the first embodiment of the first aspect wherein G is phenyl or —C$_{1-2}$alkylene-phenyl, said phenyl or phenyl of said —C$_{1-2}$alkylene-phenyl are substituted with cyano.

According to another embodiment of the first aspect of the present invention are provided compounds of Formula (I) according to the first embodiment of the first aspect wherein A—D are not interrupted with J—J', —Z-phenyl- or —Z—C$_{1-3}$alkylene.

According to another embodiment of the first aspect of the present invention are provided compounds of Formula (I) according to the first embodiment of the first aspect wherein A—D are interrupted with J—J', —Z-phenyl- or —Z—C$_{1-3}$alkylene.

According to another embodiment of the first aspect of the present invention are provided compounds of Formula (I) according to the first embodiment of the first aspect wherein A—D is interrupted with J—J'.

According to another embodiment of the first aspect of the present invention are provided compounds of Formula (I) according to the first embodiment of the first aspect wherein A—D is interrupted with —Z-phenyl- .

According to another embodiment of the first aspect of the present invention are provided compounds of Formula (I) according to the first embodiment of the first aspect wherein A—D is interrupted with —Z—$C_{1-3}$alkylene.

According to another embodiment of the first aspect of the present invention are provided compounds of Formula (I) according to the first embodiment of the first aspect wherein $R^1$ and $R^2$ are each H, $R^3$ is $C_{1-3}$alkyl, A is $C_{7-10}$alkylene, D is X(O)O and A—D is not interrupted with J—J', —Z-phenyl- or —Z—$C_{1-3}$alkylene.

According to another embodiment of the first aspect of the present invention are provided compounds of Formula (I) according to the first embodiment of the first aspect wherein $R^1$ and $R^2$ are each H, $R^3$ is $C_{1-3}$alkyl, A is $C_{1-5}$alkylene, D is X(O)O and A—D is interrupted with J—J', —Z-phenyl- or —Z—$C_{1-3}$alkylene.

According to another embodiment of the first aspect of the present invention are provided compounds of Formula (I) according to the first embodiment of the first aspect wherein $R^1$ and $R^2$ are each H, $R^3$ is $C_{1-3}$alkyl, A is $C_{7-10}$alkylene, D is X(O)N(G') and A—D is not interrupted with J—J', —Z-phenyl- or —Z—$C_{1-3}$alkylene.

According to another embodiment of the first aspect of the present invention are provided compounds of Formula (I) according to the first embodiment of the first aspect wherein $R^1$ and $R^2$ are each H, $R^3$ is $C_{1-3}$alkyl, A is $C_{1-5}$alkylene, D is X(O)N(G') and A—D is interrupted with J—J', —Z-phenyl- or —Z—$C_{1-3}$alkylene.

According to another embodiment of the first aspect of the present invention are provided compounds of Formula (I) according to the first embodiment of the first aspect wherein $R^1$ and $R^2$ are each H, $R^3$ is $C_{1-3}$alkyl, A is $C_{7-10}$alkylene, D is HYC(O)O and A—D is not interrupted with J—J', —Z-phenyl- or —Z—$C_{1-3}$alkylene.

According to another embodiment of the first aspect of the present invention are provided compounds of Formula (I) according to the first embodiment of the first aspect wherein $R^1$ and $R^2$ are each H, $R^3$ is $C_{1-3}$alkyl, A is $C_{1-5}$alkylene, D is HYC(O)O and A—D is interrupted with J—J', —Z-phenyl- or —Z—$C_{1-3}$alkylene.

According to another embodiment of the first aspect of the present invention are provided compounds of Formula (I) according to the first embodiment of the first aspect wherein $R^1$ and $R^2$ are each H, $R^3$ is $C_{1-3}$alkyl, A is $C_{7-10}$alkylene, D is HYC(O)ON=C(G') and A—D is not interrupted with J—J', —Z-phenyl- or —Z—$C_{1-3}$alkylene.

According to another embodiment of the first aspect of the present invention are provided compounds of Formula (I) according to the first embodiment of the first aspect wherein $R^1$ and $R^2$ are each H, $R^3$ is $C_{1-3}$alkyl, A is $C_{1-5}$alkylene, D is HYC(O)ON=C(G') and A—D is interrupted with J—J', —Z-phenyl- or —Z—$C_{1-3}$alkylene.

According to another embodiment of the first aspect of the present invention are provided [6-(2-Methyl-4,5-diphenyl-imidazol-1-yl)-hexyl]-carbamic acid 2-fluoro-phenyl ester;

[6-(2-Ethyl-4,5-diphenyl-imidazol-1-yl)-hexyl]-carbamic acid tert-butyl ester;

[6-(2-Ethyl-4,5-diphenyl-imidazol-1-yl)-hexyl]-carbamic acid sec-butyl ester;

[6-(2-Methyl-4,5-diphenyl-imidazol-1-yl)-hexyl]-carbamic acid benzyl ester;

2-Propanone,O-[6-(2-methyl-4,5-diphenyl-1H-imidazol-1-yl)hexyl]amino]carbonyl]oxime;

[6-(2-Methyl-4,5-diphenyl-imidazol-1-yl)-hexyl]-carbamic acid methyl ester;

6-(2-Methyl-4,5-diphenyl-imidazol-1-yl)-hexyl]-carbamic acid phenyl ester;

[6-(2-Methyl-4,5-diphenyl-imidazol-1-yl)-hexyl]-carbamic acid 4-fluoro-phenyl ester;

[6-(2-Methyl-4,5-diphenyl-imidazol-1-yl)-hexyl]-carbamic acid 2,4-difluoro-phenyl ester;

[6-(2-Methyl-4,5-diphenyl-imidazol-1-yl)-hexyl]-carbamic acid 4-chloro-phenyl ester;

[6-(2-Methyl-4,5-diphenyl-imidazol-1-yl)-hexyl]-carbamic acid 4-methoxy-phenyl ester;

[6-(2-Methyl-4,5-diphenyl-imidazol-1-yl)-hexyl]-carbamic acid o-tolyl ester;

[6-(2-Methyl-4,5-diphenyl-imidazol-1-yl)-hexyl]-carbamic acid 4-cyano-phenyl ester;

[6-(2-Methyl-4,5-diphenyl-imidazol-1-yl)-hexyl]-carbamic acid 2,6-dimethoxy-phenyl ester;

[6-(2-Methyl-4,5-diphenyl-imidazol-1-yl)-hexyl]-carbamic acid 2-methoxy-phenyl ester;

[7-(2-Methyl-4,5-diphenyl-imidazol-1-yl)-heptyl-carbamic acid methyl ester;

[7-(2-Methyl-4,5-diphenyl-imidazol-1-yl)-heptyl]-carbamic acid ethyl ester;

[7-(2-Methyl-4,5-diphenyl-imidazol-1-yl)-heptyl]-carbamic acid phenyl ester;

[7-(2-Methyl-4,5-diphenyl-imidazol-1-yl)-heptyl]-carbamic acid 4-fluoro-phenyl ester;

[7-(2-Methyl-4,5-diphenyl-imidazol-1-yl)-heptyl]-carbamic acid 2-fluoro-phenyl ester;

[7-(2-Methyl-4,5-diphenyl-imidazol-1-yl)-heptyl]-carbamic acid 2,4-difluoro-phenyl ester;

[7-(2-Methyl-4,5-diphenyl-imidazol-1-yl)-heptyl]-carbamic acid 4-chloro-phenyl ester;

[7-(2-Methyl-4,5-diphenyl-imidazol-1-yl)-heptyl]-carbamic acid 4-methoxy-phenyl ester;

[7-(2-Methyl-4,5-diphenyl-imidazol-1-yl)-heptyl]-carbamic acid o-tolyl ester;

[7-(2-Methyl-4,5-diphenyl-imidazol-1-yl)-heptyl]-carbamic acid 4-cyano-phenyl ester;

[7-(2-Methyl-4,5-diphenyl-imidazol-1-yl)-heptyl]-carbamic acid 2,6-dimethoxy-phenyl ester;

[7-(2-Methyl-4,5-diphenyl-imidazol-1-yl)-heptyl]-carbamic acid 2-methoxy-phenyl ester;

[5-(2-Methyl-4,5-diphenyl-imidazol-1-yl)-pentyl]-carbamic acid ethyl ester;

[5-(2-Methyl-4,5-diphenyl-imidazol-1-yl)-pentyl]-carbamic acid phenyl ester;

[5-(2-Methyl-4,5-diphenyl-imidazol-1-yl)-pentyl]-carbamic acid 4-fluoro-phenyl ester;

[5-(2-Methyl-4,5-diphenyl-imidazol-1-yl)-pentyl]-carbamic acid 2,4-difluoro-phenyl ester;

[5-(2-Methyl-4,5-diphenyl-imidazol-1-yl)-pentyl]-carbamic acid 2-fluoro-phenyl ester;

[5-(2-Methyl-4,5-diphenyl-imidazol-1-yl)-pentyl]-carbamic acid 4-chloro-phenyl ester;

[5-(2-Methyl-4,5-diphenyl-imidazol-1-yl)-pentyl]-carbamic acid 4-methoxy-phenyl ester;

[5-(2-Methyl-4,5-diphenyl-imidazol-1-yl)-pentyl]-carbamic acid o-tolyl ester;

[5-(2-Methyl-4,5-diphenyl-imidazol-1-yl)-pentyl]-carbamic acid 4-cyano-phenyl ester;

[5-(2-Methyl-4,5-diphenyl-imidazol-1-yl)-pentyl]-carbamic acid 2,6-dimethoxy-phenyl ester;

[5-(2-Methyl-4,5-diphenyl-imidazol-1-yl)-pentyl]-carbamic acid 2-methoxy-phenyl ester;
[6-(2-Methyl-4,5-diphenyl-imidazol-1-yl)-hexyl]-carbamic acid 3,4-difluoro-phenyl ester;
{6-[4,5-Bis-(4-fluoro-phenyl)-2-methyl-imidazol-1-yl]-hexyl}-carbamic acid 2-fluoro-phenyl ester;
{6-[4,5-Bis-(4-fluoro-phenyl)-2-methyl-imidazol-1-yl]-hexyl}-carbamic acid 2,6-difluoro-phenyl ester;
[6-(2-Methyl-4,5-diphenyl-imidazol-1-yl)-hexyl]-carbamic acid ethyl ester;
Benzaldehyde, O-[6-(2-methyl-4,5-diphenyl-1H-imidazol-1-yl)hexyl]amino]carbonyl]oxime;
4-Fluorobenzaldehyde,O-[6-(2-methyl-4,5-diphenyl-1H-imidazol-1-yl)hexyl]amino]carbonyl]oxime;
2-Nitrobenzaldehye, O-[6-(2-methyl-4,5-diphenyl-1H-imidazol-1-yl)hexyl]amino]carbonyl]oxime;
3-Nitrobenzaldehyde, O-[6-(2-methyl-4,5-diphenyl-1H-imidazol-1-yl)hexyl]amino]carbonyl]oxime;
4-Nitrobenzaldehyde, O-[6-(2-methyl-4,5-diphenyl-1H-imidazol-1-yl)hexyl]amino]carbonyl]oxime;
3-Pyridinecarboxaldehyde, O-[6-(2-methyl-4,5-diphenyl-1H-imidazol-1-yl)hexyl]amino]carbonyl]oxime;
{4-[2-(2-Methyl-4,5-diphenyl-imidazol-1-yl)-ethoxy]-phenyl}-carbamic acid 3,4-difluoro-phenyl ester;
{4-[2-(2-Methyl-4,5-diphenyl-imidazol-1-yl)-ethoxy]-phenyl}-carbamic acid 4-chloro-phenyl ester;
{4-[3-(2-Methyl-4,5-diphenyl-imidazol-1-yl)-propoxy]-phenyl}-carbamic acid 3,4-difluoro-phenyl ester;
{4-[3-(2-Methyl-4,5-diphenyl-imidazol-1-yl)-propoxy]-phenyl}-carbamic acid 4-methoxy-phenyl ester;
{4-[3-(2-Methyl-4,5-diphenyl-imidazol-1-yl)-propoxy]-phenyl}-carbamic acid 4-chloro-phenyl ester;
{4-[3-(2-Methyl-4,5-diphenyl-imidazol-1-yl)-propoxy]-phenyl}-carbamic acid 2-methoxy-phenyl ester;
{4-[3-(2-Methyl-4,5-diphenyl-imidazol-1-yl)-propoxy]-phenyl}-carbamic acid 3-chloro-phenyl ester;
{4-[2-(2-Methyl-4,5-diphenyl-imidazol-1-yl)-ethoxyl-phenyl}-carbamic acid phenyl ester;
{4-[2-(2-Methyl-4,5-diphenyl-imidazol-1-yl)-ethoxy]-phenyl}-carbamic acid 2-fluoro-phenyl ester;
{4-[2-(2-Methyl-4,5-diphenyl-imidazol-1-yl)-ethoxy]-phenyl}-carbamic acid 4-fluoro-phenyl ester;
{4-[3-(2-Methyl-4,5-diphenyl-imidazol-1-yl)-propoxy]-phenyl}-carbamic acid phenyl ester;
{4-[2-(2-Methyl-4,5-diphenyl-imidazol-1-yl)-ethoxy]-phenyl}-carbamic acid 4-methoxy-phenyl ester;
{4-[3-(2-Methyl-4,5-diphenyl-imidazol-1-yl)-propoxy]-phenyl}-carbamic acid 2-fluoro-phenyl ester;
{4-[3-(2-Methyl-4,5-diphenyl-imidazol-1-yl)-propoxy]-phenyl}-carbamic acid 2,6-difluoro-phenyl ester;
{4-[2-(2-Methyl-4,5-diphenyl-imidazol-1-yl)-ethoxy]-phenyl}-carbamic acid ethyl ester;
[1-Methyl-6-(2-methyl-4,5-diphenyl-imidazol-1-yl)-hexyl]-carbamic acid 2-fluoro-phenyl ester;
[1-Ethyl-6-(2-methyl-4,5-diphenyl-imidazol-1-yl)-hexyl]-carbamic acid 2-fluoro-phenyl ester;
[1-Isopropyl-6-(2-methyl-4,5-diphenyl-imidazol-1-yl)-hexyl]-carbamic acid 2-fluoro-phenyl ester or
[6-(2-Methyl-4,5-diphenyl-imidazol-1-yl)-1-phenyl-hexyl]-carbamic acid 2-fluoro-phenyl ester.

According to another embodiment of the first aspect of the present invention are provided [6-(2-Methyl-4,5-diphenyl-imidazol-1-yl)-hexyl]-carbamic acid 2-fluoro-phenyl ester;
2-Propanone,O-[6-(2-methyl-4,5-diphenyl-1H-imidazol-1-yl)hexyl]amino]carbonyl]oxime;
[6-(2-Methyl-4,5-diphenyl-imidazol-1-yl)-hexyl]-carbamic acid cyclohexyl ester;
[6-(2-Methyl-4,5-diphenyl-imidazol-1-yl)-hexyl]-carbamic acid methyl ester;
6-(2-Methyl-4,5-diphenyl-imidazol-1-yl)-hexyl]-carbamic acid phenyl ester;
[6-(2-Methyl-4,5-diphenyl-imidazol-1-yl)-hexyl]-carbamic acid 4-fluoro-phenyl ester;
[6-(2-Methyl-4,5-diphenyl-imidazol-1-yl)-hexyl]-carbamic acid 2,4-difluoro-phenyl ester;
[6-(2-Methyl-4,5-diphenyl-imidazol-1-yl)-hexyl]-carbamic acid 4-chloro-phenyl ester;
[6-(2-Methyl-4,5-diphenyl-imidazol-1-yl)-hexyl]-carbamic acid 4-methoxy-phenyl ester;
[6-(2-Methyl-4,5-diphenyl-imidazol-1-yl)-hexyl]-carbamic acid o-tolyl ester;
[6-(2-Methyl-4,5-diphenyl-imidazol-1-yl)-hexyl]-carbamic acid 4-cyano-phenyl ester;
[6-(2-Methyl-4,5-diphenyl-imidazol-1-yl)-hexyl]-carbamic acid 2,6-dimethoxy-phenyl ester;
[6-(2-Methyl-4,5-diphenyl-imidazol-1-yl)-hexyl]-carbamic acid 2-methoxy-phenyl ester;
[7-(2-Methyl-4,5-diphenyl-imidazol-1-yl)-heptyl]-carbamic acid methyl ester;
[7-(2-Methyl-4,5-diphenyl-imidazol-1-yl)-heptyl]-carbamic acid ethyl ester;
[7-(2-Methyl-4,5-diphenyl-imidazol-1-yl)-heptyl]-carbamic acid phenyl ester;
[7-(2-Methyl-4,5-diphenyl-imidazol-1-yl)-heptyl]-carbamic acid 4-fluoro-phenyl ester;
[7-(2-Methyl-4,5-diphenyl-imidazol-1-yl)-heptyl]-carbamic acid 2-fluoro-phenyl ester;
[7-(2-Methyl-4,5-diphenyl-imidazol-1-yl)-heptyl]-carbamic acid 2,4-difluoro-phenyl ester;
[7-(2-Methyl-4,5-diphenyl-imidazol-1-yl)-heptyl]-carbamic acid 4-chloro-phenyl ester;
[7-(2-Methyl-4,5-diphenyl-imidazol-1-yl)-heptyl]-carbamic acid 4-methoxy-phenyl ester;
[7-(2-Methyl-4,5-diphenyl-imidazol-1-yl)-heptyl]-carbamic acid o-tolyl ester;
[7-(2-Methyl-4,5-diphenyl-imidazol-1-yl)-heptyl]-carbamic acid 4-cyano-phenyl ester;
[7-(2-Methyl-4,5-diphenyl-imidazol-1-yl)-heptyl]-carbamic acid 2,6-dimethoxy-phenyl ester;
[7-(2-Methyl-4,5-diphenyl-imidazol-1-yl)-heptyl]-carbamic acid 2-methoxy-phenyl ester;
[5-(2-Methyl-4,5-diphenyl-imidazol-1-yl)-pentyl]-carbamic acid ethyl ester;
[5-(2-Methyl-4,5-diphenyl-imidazol-1-yl)-pentyl]-carbamic acid phenyl ester;
[5-(2-Methyl-4,5-diphenyl-imidazol-1-yl)-pentyl]-carbamic acid 4-fluoro-phenyl ester;
[5-(2-Methyl-4,5-diphenyl-imidazol-1-yl)-pentyl]-carbamic acid 2,4-difluoro-phenyl ester;
[5-(2-Methyl-4,5-diphenyl-imidazol-1-yl)-pentyl]-carbamic acid 2-fluoro-phenyl ester;
[5-(2-Methyl-4,5-diphenyl-imidazol-1-yl)-pentyl]-carbamic acid 4-chloro-phenyl ester;
[5-(2-Methyl-4,5-diphenyl-imidazol-1-yl)-pentyl]-carbamic acid 4-methoxy-phenyl ester;
[5-(2-Methyl-4,5-diphenyl-imidazol-1-yl)-pentyl]-carbamic acid o-tolyl ester;
[5-(2-Methyl-4,5-diphenyl-imidazol-1-yl)-pentyl]-carbamic acid 4-cyano-phenyl ester;
[5-(2-Methyl-4,5-diphenyl-imidazol-1-yl)-pentyl]-carbamic acid 2-methoxy-phenyl ester;
[6-(2-Methyl-4,5-diphenyl-imidazol-1-yl)-hexyl]-carbamic acid 3,4-difluoro-phenyl ester;
[6-(2-Methyl-4,5-diphenyl-imidazol-1-yl)-hexyl]-carbamic acid isopropyl ester;

{6-[4,5-Bis-(4-fluoro-phenyl)-2-methyl-imidazol-1-yl]-hexyl}-carbamic acid 2-fluoro-phenyl ester;
{6-[4,5-Bis-(4-fluoro-phenyl)-2-methyl-imidazol-1-yl]-hexyl}-carbamic acid 2,6-difluoro-phenyl ester;
[6-(2-Methyl-4,5-diphenyl-imidazol-1-yl)-hexyl]-carbamic acid ethyl ester;
Benzaldehyde, O-[6-(2-methyl-4,5-diphenyl-1H-imidazol-1-yl)hexyl]amino]carbonyl]oxime;
4-Fluorobenzaldehyde,O-[6-(2-methyl-4,5-diphenyl-1H-imidazol-1-yl)hexyl]amino]carbonyl]oxime;
2-Nitrobenzaldehye, O-[6-(2-methyl-4,5-diphenyl-1H-imidazol-1-yl)hexyl]amino]carbonyl]oxime;
3-Nitrobenzaldehyde, O-[6-(2-methyl-4,5-diphenyl-1H-imidazol-1-yl)hexyl]amino]carbonyl]oxime;
4-Nitrobenzaldehyde, O-[6-(2-methyl-4,5-diphenyl-1H-imidazol-1-yl)hexyl]amino]carbonyl]oxime;
3-Pyridinecarboxaldehyde, O-[6-(2-methyl-4,5-diphenyl-1H-imidazol-1-yl)hexyl]amino]carbonyl]oxime;
{4-[3-(2-Methyl-4,5-diphenyl-imidazol-1-yl)-propoxy]-phenyl}-carbamic acid 3,4-difluoro-phenyl ester;
{4-[3-(2-Methyl-4,5-diphenyl-imidazol-1-yl)-propoxy]-phenyl}-carbamic acid 4-methoxy-phenyl ester;
{4-[3-(2-Methyl-4,5-diphenyl-imidazol-1-yl)-propoxy]-phenyl}-carbamic acid 4-chloro-phenyl ester;
{4-[3-(2-Methyl-4,5-diphenyl-imidazol-1-yl)-propoxy]-phenyl}-carbamic acid 2-methoxy-phenyl ester;
{4-[3-(2-Methyl-4,5-diphenyl-imidazol-1-yl)-propoxy]-phenyl}-carbamic acid 3-chloro-phenyl ester;
[1-Methyl-6-(2-methyl-4,5-diphenyl-imidazol-1-yl)-hexyl]-carbamic acid 2-fluoro-phenyl ester;
[1-Ethyl-6-(2-methyl-4,5-diphenyl-imidazol-1-yl)-hexyl]-carbamic acid 2-fluoro-phenyl ester;
[1-Isopropyl-6-(2-methyl-4,5-diphenyl-imidazol-1-yl)-hexyl]-carbamic acid 2-fluoro-phenyl ester; or
[6-(2-Methyl-4,5-diphenyl-imidazol-1-yl)-1-phenyl-hexyl]-carbamic acid 2-fluoro-phenyl ester.

According to another embodiment of the first aspect of the present invention are provided [6-(2-Methyl-4,5-diphenyl-imidazol-1-yl)-hexyl]-carbamic acid 2-fluoro-phenyl ester;
2-Propanone,O-[6-(2-methyl-4,5-diphenyl-1H-imidazol-1-yl)hexyl]amino]carbonyl]oxime;
6-(2-Methyl-4,5-diphenyl-imidazol-1-yl)-hexyl]-carbamic acid phenyl ester;
[6-(2-Methyl-4,5-diphenyl-imidazol-1-yl)-hexyl]-carbamic acid 4-fluoro-phenyl ester;
[6-(2-Methyl-4,5-diphenyl-imidazol-1-yl)-hexyl]-carbamic acid 2,4-difluoro-phenyl ester;
[6-(2-Methyl-4,5-diphenyl-imidazol-1-yl)-hexyl]-carbamic acid 4-chloro-phenyl ester;
[6-(2-Methyl-4,5-diphenyl-imidazol-1-yl)-hexyl]-carbamic acid 4-methoxy-phenyl ester;
[6-(2-Methyl-4,5-diphenyl-imidazol-1-yl)-hexyl]-carbamic acid o-tolyl ester;
[6-(2-Methyl-4,5-diphenyl-imidazol-1-yl)-hexyl]-carbamic acid 4-cyano-phenyl ester;
[7-(2-Methyl-4,5-diphenyl-imidazol-1-yl)-heptyl]-carbamic acid ethyl ester;
[7-(2-Methyl-4,5-diphenyl-imidazol-1-yl)-heptyl]-carbamic acid phenyl ester;
[7-(2-Methyl-4,5-diphenyl-imidazol-1-yl)-heptyl]-carbamic acid 4-fluoro-phenyl ester;
[7-(2-Methyl-4,5-diphenyl-imidazol-1-yl)-heptyl]-carbamic acid 2-fluoro-phenyl ester;
[7-(2-Methyl-4,5-diphenyl-imidazol-1-yl)-heptyl]-carbamic acid 2,4-difluoro-phenyl ester;
[7-(2-Methyl-4,5-diphenyl-imidazol-1-yl)-heptyl]-carbamic acid 4-chloro-phenyl ester;
[7-(2-Methyl-4,5-diphenyl-imidazol-1-yl)-heptyl]-carbamic acid 4-methoxy-phenyl ester;
[7-(2-Methyl-4,5-diphenyl-imidazol-1-yl)-heptyl]-carbamic acid o-tolyl ester;
[7-(2-Methyl-4,5-diphenyl-imidazol-1-yl)-heptyl]-carbamic acid 4-cyano-phenyl ester;
[7-(2-Methyl-4,5-diphenyl-imidazol-1-yl)-heptyl]-carbamic acid 2-methoxy-phenyl ester;
[5-(2-Methyl-4,5-diphenyl-imidazol-1-yl)-pentyl]-carbamic acid phenyl ester;
[5-(2-Methyl-4,5-diphenyl-imidazol-1-yl)-pentyl]-carbamic acid 4-fluoro-phenyl ester;
[5-(2-Methyl-4,5-diphenyl-imidazol-1-yl)-pentyl]-carbamic acid 2,4-difluoro-phenyl ester;
[5-(2-Methyl-4,5-diphenyl-imidazol-1-yl)-pentyl]-carbamic acid 2-fluoro-phenyl ester;
[5-(2-Methyl-4,5-diphenyl-imidazol-1-yl)-pentyl]-carbamic acid 4-chloro-phenyl ester;
[5-(2-Methyl-4,5-diphenyl-imidazol-1-yl)-pentyl]-carbamic acid 4-methoxy-phenyl ester;
[5-(2-Methyl-4,5-diphenyl-imidazol-1-yl)-pentyl]-carbamic acid 4-cyano-phenyl ester;
[5-(2-Methyl-4,5-diphenyl-imidazol-1-yl)-pentyl]-carbamic acid 2,6-dimethoxy-phenyl ester;
[6-(2-Methyl-4,5-diphenyl-imidazol-1-yl)-hexyl]-carbamic acid 3,4-difluoro-phenyl ester;
{6-[4,5-Bis-(4-fluoro-phenyl)-2-methyl-imidazol-1-yl]-hexyl}-carbamic acid 2-fluoro-phenyl ester;
{6-[4,5-Bis-(4-fluoro-phenyl)-2-methyl-imidazol-1-yl]-hexyl}-carbamic acid 2,6-difluoro-phenyl ester;
Benzaldehyde, O-[6-(2-methyl-4,5-diphenyl-1H-imidazol-1-yl)hexyl]amino]carbonyl]oxime;
4-Fluorobenzaldehyde,O-[6-(2-methyl-4,5-diphenyl-1H-imidazol-1-yl)hexyl]amino]carbonyl]oxime;
2-Nitrobenzaldehye, O-[6-(2-methyl-4,5-diphenyl-1H-imidazol-1-yl)hexyl]amino]carbonyl]oxime;
3-Nitrobenzaldehyde, O-[6-(2-methyl-4,5-diphenyl-1H-imidazol-1-yl)hexyl]amino]carbonyl]oxime;
4-Nitrobenzaldehyde, O-[6-(2-methyl-4,5-diphenyl-1H-imidazol-1-yl)hexyl]amino]carbonyl]oxime;
3-Pyridinecarboxaldehyde, O-[6-(2-methyl-4,5-diphenyl-1H-imidazol-1-yl)hexyl]amino]carbonyl]oxime;
[1-Methyl-6-(2-methyl-4,5-diphenyl-imidazol-1-yl)-hexyl]-carbamic acid 2-fluoro-phenyl ester; or
[1-Ethyl-6-(2-methyl-4,5-diphenyl-imidazol-1-yl)-hexyl]-carbamic acid 2-fluoro-phenyl ester.

According to another embodiment of the first aspect of the present invention are provided [6-(2-Methyl-4,5-diphenyl-imidazol-1-yl)-hexyl]-carbamic acid 2-fluoro-phenyl ester;
6-(2-Methyl-4,5-diphenyl-imidazol-1-yl)-hexyl]-carbamic acid phenyl ester;
[6-(2-Methyl-4,5-diphenyl-imidazol-1-yl)-hexyl]-carbamic acid 4-fluoro-phenyl ester;
[6-(2-Methyl-4,5-diphenyl-imidazol-1-yl)-hexyl]-carbamic acid 2,4-difluoro-phenyl ester;
[6-(2-Methyl-4,5-diphenyl-imidazol-1-yl)-hexyl]-carbamic acid 4-chloro-phenyl ester;
[6-(2-Methyl-4,5-diphenyl-imidazol-1-yl)-hexyl]-carbamic acid o-tolyl ester;
[7-(2-Methyl-4,5-diphenyl-imidazol-1-yl)-heptyl]-carbamic acid phenyl ester;
[7-(2-Methyl-4,5-diphenyl-imidazol-1-yl)-heptyl]-carbamic acid 2-fluoro-phenyl ester;
[7-(2-Methyl-4,5-diphenyl-imidazol-1-yl)-heptyl]-carbamic acid 4-chloro-phenyl ester;
[7-(2-Methyl-4,5-diphenyl-imidazol-1-yl)-heptyl]-carbamic acid 4-cyano-phenyl ester;

[6-(2-Methyl-4,5-diphenyl-imidazol-1-yl)-hexyl]-carbamic acid 3,4-difluoro-phenyl ester;
{6-[4,5-Bis-(4-fluoro-phenyl)-2-methyl-imidazol-1-yl]-hexyl}-carbamic acid 2-fluoro-phenyl ester; or
[1-Methyl-6-(2-methyl-4,5-diphenyl-imidazol-1-yl)-hexyl]-carbamic acid 2-fluoro-phenyl ester.

According to various embodiments of a second aspect of the present invention are provided pharmaceutical formulations comprising compounds of Formula (I) as defined herein.

According to various embodiments of a third aspect of the present invention are provided methods of treating conditions the treatment of which can be effected by the inhibition of FAAH by the administration of pharmaceutical compositions comprising compounds of Formula (I) as defined herein.

According to another embodiment of the third aspect of the present invention is provided a method of treating pain, more particularly chronic pain, acute pain and neuropathic pain by the administration of pharmaceutical compositions comprising compounds of Formula (I) as defined herein.

According to another embodiment of the third aspect of the present invention is provided a method of treating pain, more particularly chronic pain, acute pain and neuropathic pain by the administration of a pharmaceutical composition comprising

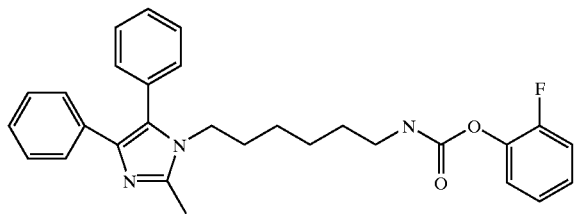

or salt or solvate thereof.

According to another embodiment of the third aspect of the present invention is provided a method of treating neuropathic pain by the administration of a pharmaceutical composition comprising

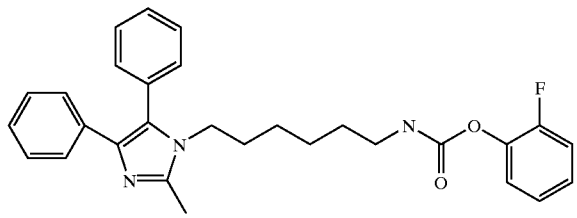

or salt or solvate thereof.

According to another embodiment of the third aspect of the present invention is provided a method of providing neuroprotection and contraception and yet further methods of psychomotor disorder, hypertension, cardiovascular disease, eating disorder, nausea, AIDS-related complex, glaucoma, inflammation, psoriasis and multiple sclerosis by the administration of pharmaceutical compositions comprising compounds of Formula (I) as defined herein. See Raphael Mechoulam, "Looking Back at Cannabis Research," *Current Pharmaceutical Design*, 2000, Vol. 6, No. 13, pp. 1313–1322 (p. 1319); Sumner H. Burstein, "Ajulemic Acid (CT3): A Potent Analog of the Acid Metabolites of THC," *Current Pharmaceutical Design*, 2000, Vol. 6, No. 13, pp. 1339–1345 (p. 1340); Vincenzo Di Marzo, et al., "Endocannabinoids: New Targets for Drug Development," *Current Pharmaceutical Design*, 2000, Vol. 6, No. 13, pp. 1361–1380 (p. 1362); and Sonya L. Palmer, et al., "Natural and Synthetic Endocannabinoids and Their Structure-Activity Relationships," *Current Pharmaceutical Design*, 2000, Vol. 6, No. 13, pp. 1381–1397 (p. 1386).

Other embodiments of the present invention may comprise a suitable combination of two or more of embodiments and/or aspects disclosed herein.

Yet other embodiments and aspects of the invention will be apparent according to the description provided below.

DETAILED DESCRIPTION OF THE INVENTION

Figure 1:
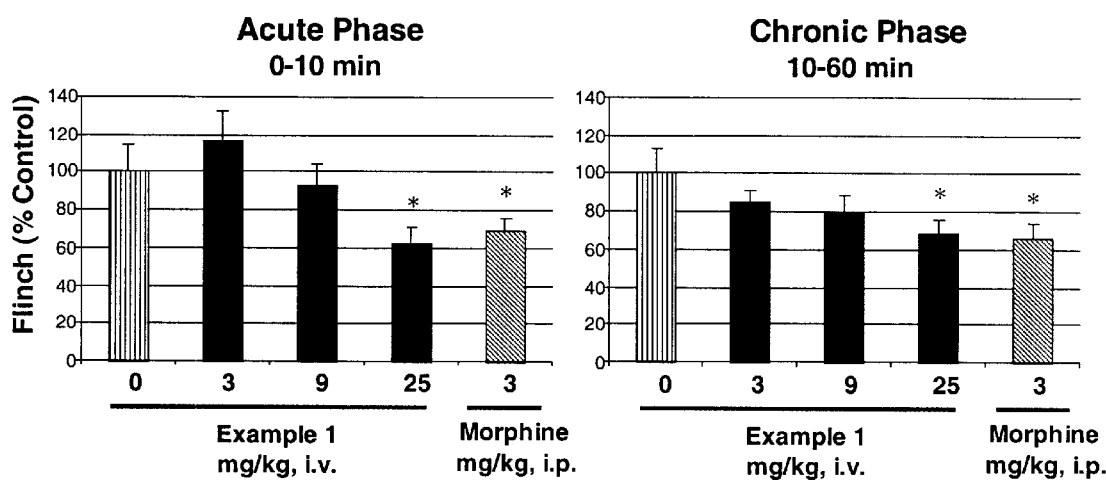
FIG. 1A illustrates results from a rat formalin model used for testing acute chemo-induced pain. The single asterisk (*) applies when p is less than 0.05.
FIG. 1B illustrates results from a rat formalin model used for testing chronic chemo-induced pain. The single asterisk (*) applies when p is less than 0.05.

The description of the invention herein should be construed in congruity with the laws and principals of chemical bonding. For example, when a moiety is optionally substituted and said substitution requires the removal of a hydrogen atom from the moiety to be substituted, the description of the moiety should be read to include the moiety with or without said hydrogen atom. As another example, if a variable is defined as a particular moiety or atom and is further defined to have value of 0 or some integer, the bond(s) attaching said moiety should be suitably removed in the event the variable equals 0. An embodiment or aspect which depends from another embodiment or aspect, will describe only the variables having values and provisos that differ from the embodiment or aspect from which it depends. It is to be understood that the present invention may include any and all possible stereoisomers, geometric isomers, diastereoisomers, enantiomers, anomers and optical isomers, unless a particular description specifies otherwise. As used herein, "halo" or "halogen" includes fluoro, chloro, bromo and iodo. As used herein, "alkyl" or "alkylene" includes straight or branched chain configurations.

The compounds of this invention can exist in the form of pharmaceutically acceptable salts. Such salts include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group can exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

The dosage and dosage regimen and scheduling of a compounds of the present invention must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level which will produce effective beneficial effects without causing any harmful or untoward side effects.

Compounds of the present invention may be synthesized according to the description provided below. Variables provided in the schema below are defined in accordance with the description of compounds of Formula (I) unless otherwise specified.

EXPERIMENTALS
Scheme 1

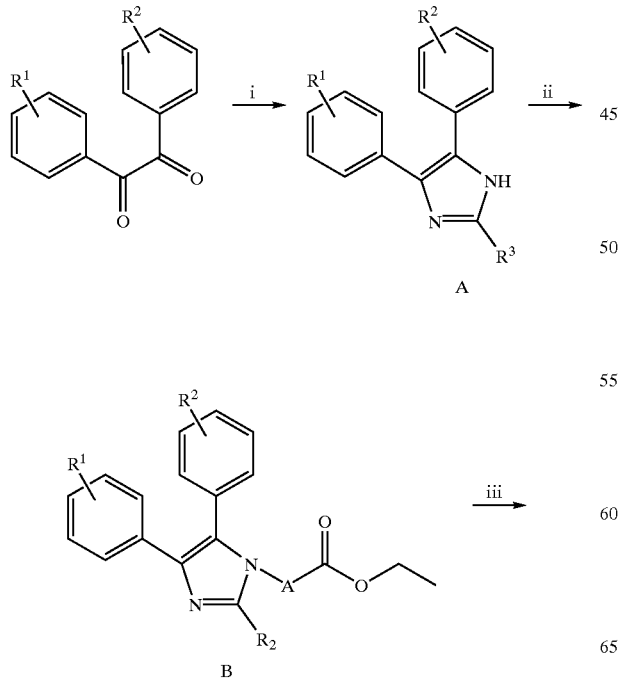

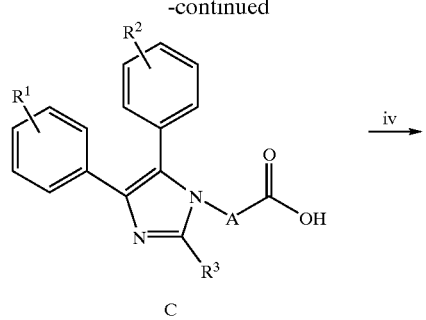

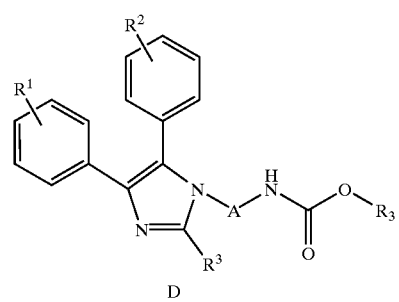

Reaction conditions: (i) aldehyde, CH₃COONH₄, CH₃COOH, 100° C.; (ii) bromide, NaH, DMF, rt; (iii) NaOH, EtOH, rt; (iv)(a) N₃P(O)(OPh)₂, Et₃N, toluene, 105° C., (b) R₃OH, 80° C.

The following Intermediates 1–13 may be used to synthesize Examples 1–51.

Intermediate 1

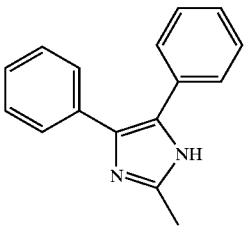

2-Methyl-4,5-diphenyl-1H-imidazole: (Scheme 1, (A)) To a solution of benzil (3.0 g, 14 mmol) in glacial acetic acid (100 mL) was added ammonium acetate (22.2 g, 284 mmol) followed with acetaldehyde (1.26 g, 28 mmol). The resultant suspension was stirred at 100° C. for 2.5 hours. After removal of most of solvent, the residue was dissolved in EtOAc. The precipitate ammonium acetate was filtered off. The filtrate was washed with 2N NaOH, H₂O, and then was dried over MgSO₄. After filtration and concentration in vacuo, the residue was purified by flash chromatography (SiO₂: EtOAc/Hexanes). This compound was obtained as a white solid (0.96 g, 4.1 mmol, 29% yield): mp 232–235° C.; MS m/e 235.0 (MH⁺); ¹H NMR (DMSO-d₆) δ7.27 (br m, 10H), 2.33 (s, 3H); ¹³C NMR (DMSO-d₆) δ144.3, 128.7, 128.3, 127.8, 127.3, 126.3, and 14.0. Anal. Calcd for $C_{16}H_{14}N_2 \cdot 0.12 H_2O$: C, 81.26; H, 6.07; N, 11.85. Found: C, 81.20; H, 6.03; N, 11.89.

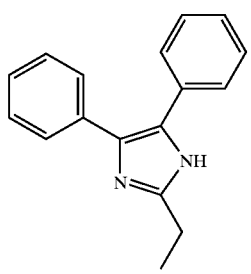

Intermediate 2

2-Ethyl-4,5-diphenyl-1H-imidazole: (Scheme 1, (A)) Prepared as described for the example above. $^1$H NMR (DMSO): δ1.30 (t, 3H), 2.72 (q, 2H), 7.44 (b, 10H), 12.02 (b, 1H); Mass Spec: 249.26 (MH$^+$).

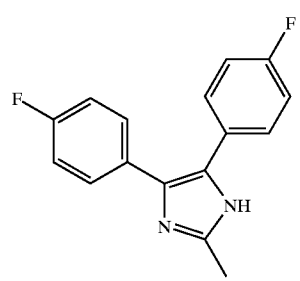

Intermediate 3

4,5-Bis-(4-fluoro-phenyl)-2-methyl-1H-imidazole: (Scheme 1, (A)) Prepared as described for the example above. $^1$H NMR (DMSO): δ2.32 (s, 3H), 7.13 (t, 2H), 7.27 (t, 2H), 7.47 (m, 4H), 12.15 (b, 1H).

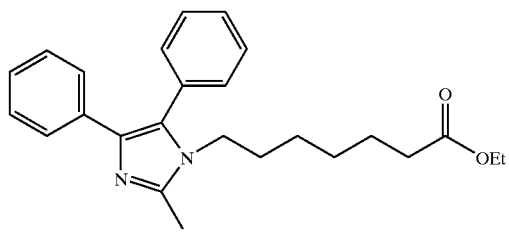

Intermediate 4

7-(2-Methyl-4,5-diphenyl-imidazol-1-yl)-heptanoic acid ethyl ester: (Scheme 1, (B)) To a solution of 2-methyl-4,5-diphenyl-1H-imidazole (0.20 g, 0.85 mmol) in DMF (6 mL) was added NaH (60% in mineral oil, 0.038 g, 0.94 mmol). The resulting mixture was stirred at rt for 10 min. The stirring continued for 2 hours after addition of ethyl 7-bromoheptanoate (0.21 g, 0.90 mmol). The reaction mixture was diluted with diethyl ether (30 mL), washed by water, and then was dried over MgSO$_4$. After filtration and concentration in vacuo, the residue was purified by flash chromatography (SiO$_2$: EtOAc/Hexanes). This compound was obtained as a colorless oil (0.24 g, 0.61 mmol, 72% yield): $^1$H NMR (DMSO-d$_6$) δ1.08 (m, 4H), 1.15 (t, J=7.2 Hz, 3H), 1.33 (m, 4H), 2.16 (t, J=6.6 Hz, 2H), 2.40 (s, 3H), 3.68 (t, J=7.8 Hz, 2H), 4.03 (q, J=4.5 Hz, 2H), 7.05)m, 1H), 7.13 (m, 2H), 7.34 (m, 4H), 7.48 (m, 3H); $^{13}$C NMR (DMSO-d$_6$) δ13.4, 14.4, 24.3, 25.7, 27.8, 29.6, 33.5, 43.3, 59.9, 125.8, 126.0, 128.1, 128.3, 128.8, 129.3, 131.1, 131.8, 135.2, 135.3, and 144.0. Anal. Calcd for C$_{25}$H$_{30}$N$_2$O$_2$: C, 76.89; H, 7.74; N, 7.17. Found: C, 76.33; H, 7.67, N, 6.85.

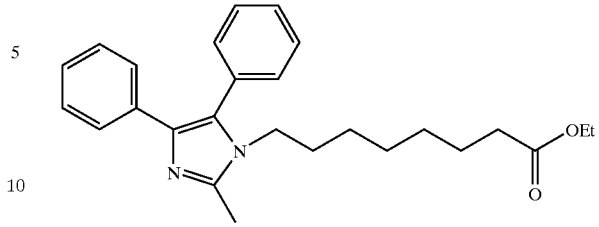

Intermediate 5

8-(2-Methyl-4,5-diphenyl-imidazol-1-yl)-octanoic acid ethyl ester: (Scheme 1, (B)) Prepared as described for the example above. $^1$H NMR (DMSO): δ1.06 (b, 6H), 1.20 (t, 3H), 1.42 (m, 4H), 2.22 (t, 2H), 2.49 (s, 3H), 3.70 (t, 2H), 4.06 (q, 2H), 7.16 (m, 3H), 7.35 (m, 4H), 7.51 (m, 3H). Mass Spec: 405.32 (MH$^+$).

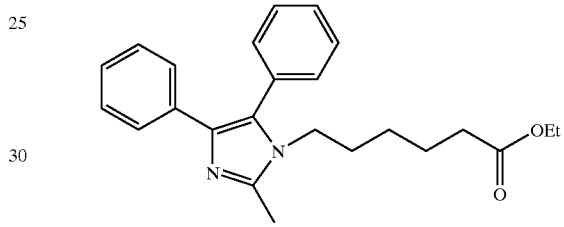

Intermediate 6

6-(2-Methyl-4,5-diphenyl-imidazol-1-yl)-hexanoic acid ethyl ester: (Scheme 1, (B)) Prepared as described for the example above. $^1$H NMR (DMSO): δ1.13 (m, 2H), 1.17 (t, 3H), 1.43 (m, 4H), 2.15 (t, 2H), 2.40 (s, 3H), 3.70 (t, 2H), 4.04 (q, 2H), 7.13 (m, 3H), 7.47 (m, 4H), 7.54 (m, 3H). Mass Spec: 377.26 (MH$^+$).

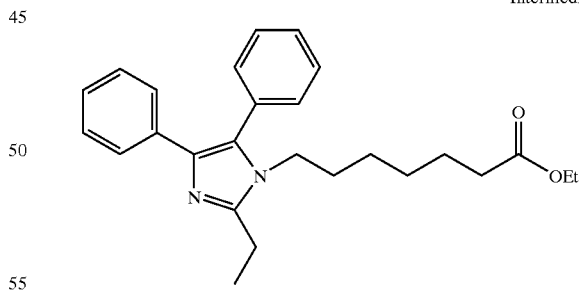

Intermediate 7

8-(2-Ethyl-4,5-diphenyl-imidazol-1-yl)-heptanoic acid ethyl ester: (Scheme 1, (B)) Prepared as described for the example above. $^1$H NMR (DMSO-d$_6$) δ1.08 (m, 4H), 1.15 (t, J=7.2 Hz, 3H), 1.33 (m, 7H), 2.16 (t, J=6.6 Hz, 2H), 2.71 (q, J=7.5 Hz), 3.68 (t, J=7.8 Hz, 2H), 4.03 (q, J=4.5 Hz, 2H), 7.05 (m, 1H), 7.13 (m, 2H), 7.34 (m, 4H), 7.48 (m, 3H). Anal. Calcd for C$_{26}$H$_{32}$N$_2$O$_2$: C, 77.19; H, 7.97; N, 6.92. Found: C, 77.06; H, 8.13; N, 6.89. Mass Spec: 405.2 (MH$^+$).

Intermediate 8

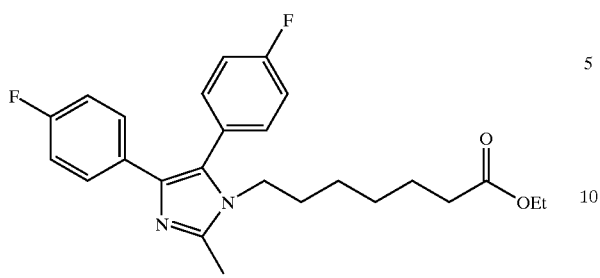

7-[4,5-Bis-(4-fluoro-phenyl)-2-methyl-imidazol-1-yl]-heptanoic acid ethyl ester: (Scheme 1, (B)) Prepared as described for the example above. $^1$H NMR (DMSO): δ1.09 (m, 4H), 1.17 (t, 3H), 1.38 (m, 4H), 2.19 (t, 2H), 2.39 (s, 3H), 3.6 (t, 2H), 4.05 (q, 2H), 7.03 (t, 2H), 7.36 (m, 4H), 7.41 (m, 2H). Mass Spec: 427.49 (MH$^+$).

Intermediate 9

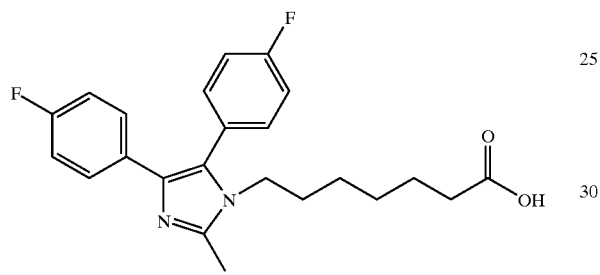

7-[4,5-Bis-(4-fluoro-phenyl)-2-methyl-imidazol-1-yl]-heptanoic acid: (Scheme 1, (C)) To a solution of 7-[4,5-Bis-(4-fluoro-phenyl)-2-methyl-imidazol-1-yl]-heptanoic acid ethyl ester (1.9 g, 4.4 mmol) in EtOH (10 mL) was added NaOH (10 N, 2 mL, 20 mmol). The resulting mixture was stirred at rt for 1 hour, diluted with EtOAc (100 mL), washed by HCl (0.5 N), and then was dried over MgSO$_4$. After filtration and concentration in vacuo, the residue was purified by flash chromatography (SiO$_2$: MeOH/CH$_2$Cl$_2$). This compound was obtained as a white solid in HCl salt form (1.9 g, 4.3 mmol, 98% yield): $^1$H NMR (DMSO): δ1.15 (m, 4H), 1.37 (t, 2H), 1.47 (t, 2H), 2.13 (t, 2H), 2.73 (s, 3H), 4.03 (t, 2H), 7.35 (t,2H), 7.45 (m, 4H), 7.57 (m, 2H), 12.1 (b, 1H).

Intermediate 10

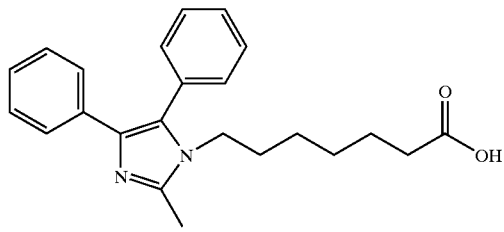

8-(2-Methyl-4,5-diphenyl-imidazol-1-yl)-heptanoic acid: (Scheme 1, (C)) Prepared as described for the example above. $^1$H NMR (DMSO-d$_6$) δ11.95 (br s, 1H), 7.56 (m, 3H), 7.46 (m, 2H), 7.38 (m, 2H), 7.28 (m, 3H), 3.83 (t, 2H, J=7.5 Hz), 2.67 (s, 3H), 2.09 (t, 2H, J=7.5 Hz), 1.38 (m, 2H), 1.25 (m, 2H), and 1.09 (m, 4H), $^{13}$C NMR (DMSO-d$_6$) δ174.5, 144.4, 131.3, 130.1, 129.6, 128.9, 128.8, 128.4, 128.1, 126.8, 44.3, 33.8, 29.4, 28.9, 25.6, 22.3 and 11.7. Anal. Calcd for C$_{23}$H$_{26}$N$_2$O$_2$.0.95 HCl.0.32 C$_6$H$_{14}$: C, 70.48; H, 7.46; N, 6.60. Found: C, 70.82; H, 7.08, N, 6.64.

Intermediate 11

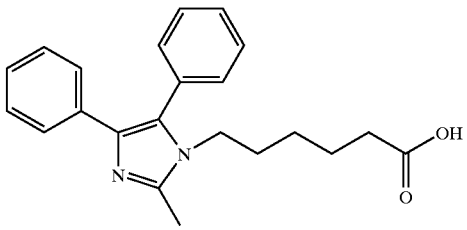

6-(2-Methyl-4,5-diphenyl-imidazol-1-yl)-hexanoic acid: (Scheme 1, (C)) Prepared as described for the example above. $^1$H NMR DMSO): δ1.17 (m, 2H), 1.33 (m, 2H), 1.51 (m, 2H), 2.09 (t, 2H), 2.76 (s, 3H), 4.03 (t, 2H), 7.38 (m, 5H), 7.49 (m, 2H), 7.65 (m, 3H).

Intermediate 12

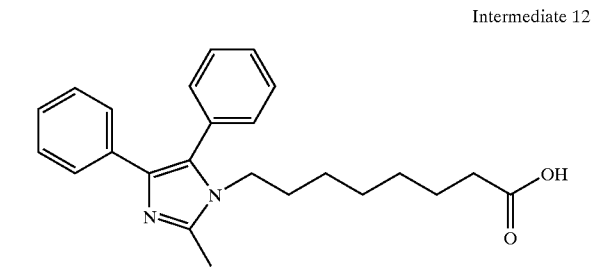

8-(2-Methyl-4,5-diphenyl-imidazol-1-yl)-octanoic acid: (Scheme 1, (C)) Prepared as described for the example above. $^1$H NMR (DMSO): δ1.07 (b, 6H), 1.39 (m, 2H), 1.48 (m, 2H), 2.15 (t, 2H), 2.72 (s, 3H), 3.92 (t, 2H), 7.35 (s, 5H), 7.52 (m, 2H), 7.606 (m, 3H), 12.1 (b, 1H). Anal. Calcd. for C$_{24}$H$_{28}$N$_2$O$_2$.0.982HCl. 0.59H2O: C, 68.16; H, 7.19; N, 6.62. Found: C, 68.00; H, 7.09; N, 6.81.

Intermediate 13

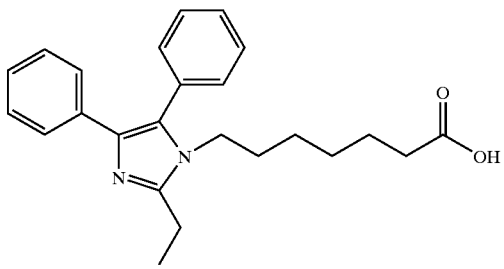

8-(2-Ethyl-4,5-diphenyl-imidazol-1-yl)-heptanoic acid: (Scheme 1, (C)) Prepared as described for the example above. $^1$H NMR (DMSO-d$_6$) δ11.95 (br s, 1H), 7.56 (m, 3H), 7.46 (m, 2H), 7.38 (m, 2H), 7.28 (m, 3H), 3.83 (t, 2H, J=7.5 Hz), 3.13 (q, J=7.8 Hz, 2H), 2.09 (t, 2H, J=7.5 Hz), 1.38 (m, 5H), 1.25 (m, 2H), and 1.09 (m, 4H). Anal. Calcd for C$_{24}$H$_{28}$N$_2$O$_2$.1.00HCl.0.44 C$_6$H$_{14}$: C, 68.44; H, 7.15; N, 6.65. Found: C, 68.43; H, 6.98; N, 6.53.

EXAMPLE 1

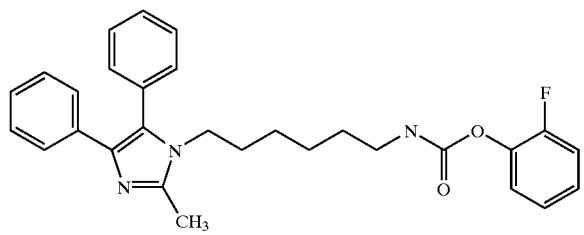

[6-(2-Methyl-4,5-diphenyl-imidazol-1-yl)-hexyl]-carbamic acid 2-fluoro-phenyl ester: (Scheme 1 (D)) To a suspension of 8-(2-Methyl-4,5-diphenyl-imidazol-1-yl)-heptanoic acid (11.3 g, 28.3 mmol) in a mixture of $Et_3N$ (10 g, 99 mmol) and toluene (200 mL) was added azide (11.0 g, 39.7 mmol). The resultant mixture was stirred at r.t. for 10 min. and then at 108° C. under $N_2$ for 90 min. After the mixture was cooled to r.t., 2-fluorophenol (3.8 g, 37 mmol) was added. The reaction mixture was stirred at r.t. for 10 min and then at 80° C. for 1 h. The mixture was diluted with EtOAc, washed with $H_2O$, and then was dried over $MgSO_4$. After filtration and concentration in vacuo, the residue was purified by flash chromatography ($SiO_2$: EtOAc/Hexanes). This compound was obtained as a white solid (7.3 g, 15.5 mmol, 55% yield): mp 129–131° C.; $^1$H NMR (DMSO-$d_6$) δ7.85 (br s, 1H), 7.50 (m, 3H), 7.33 (m, 5H), 7.30–7.05 (m, 6H), 3.69 (t, 2H, J=4.8 Hz), 2.95 (dd, 2H, J=4.8, 3.6 Hz), 2.4 (s, 3H), 1.4 (m, 2H), 1.3 (m, 2H), 1.09 (m, 4H). Anal. Calcd for $C_{29}H_{30}FN_3O_2$: C, 73.86; H, 6.41; N, 8.91. Found: C, 73.63; H, 6.45; N, 8.81. Mass Spec: 472.2 (MH$^+$).

EXAMPLE 2

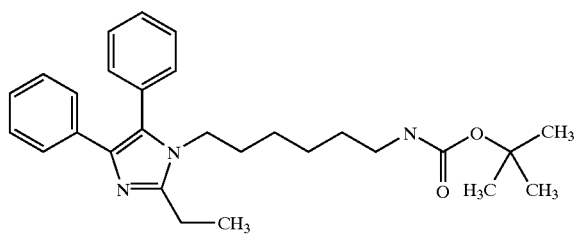

[6-(2-Ethyl-4,5-diphenyl-imidazol-1-yl)-hexyl]-carbamic acid tert-butyl ester (Scheme 1, (D)) Prepared as described for the example above. $^1$H NMR (DMSO): δ1.04 (m, 4H), 1.28 (m, 7H), 1.35 (s, 9H), 2.79 (m, 4H), 3.68 (t, 2H), 7.08 (t, 1H), 7.16 (t, 2H), 7.36 (m, 4H), 7.51 (m, 3H). Anal. Calcd. for C28H37N3O2. 0.196 CH2Cl2. 0.4 C6H14: C, 73.68; H, 8.69; N, 8.43. Found: C, 73.81; H, 8.38; N, 8.19. Mass Spec: 448.2 (MH$^+$).

EXAMPLE 3

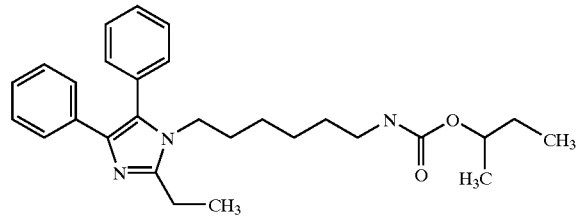

6-(2-Ethyl-4,5-diphenyl-imidazol-1-yl)-hexyl]-carbamic acid sec-butyl ester: (Scheme 1, (D)) Prepared as described for the example above. $^1$H NMR (DMSO): δ0.84 (t, 3H), 1.03 (bs, 4H), 1.11 (d, J=6.27 Hz, 3H), 1.36 (t, 2H), 1.48 (m, 7H), 2.76 (q, 2H), 2.84 (q, 2H), 3.71 (t, 2H), 4.55 (m, 1H), 6.8 (t, 1H), 7.05 (m, 1H), 7.16 (t, 2H), 7.36 (m, 4H), 7.50 (m, 3H). Anal. Calcd. for $C_{28}H_{37}N_3O_2$. 0.17 $CH_2Cl_2$. 0.245 $C_6H_{14}$: C, 73.66; H, 8.50; N, 8.70. Found: C, 73.73; H, 8.19; N, 8.69. Mass Spec: 448.2 (MH$^+$).

EXAMPLE 4

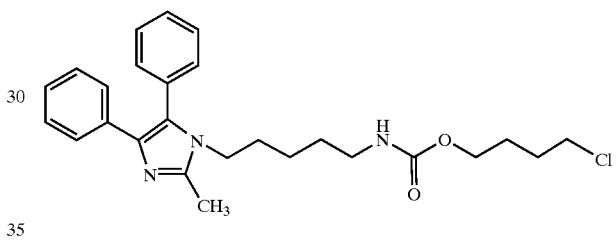

[6-(2-Methyl-4,5-diphenyl-imidazol-1-yl)-hexyl]-carbamic acid 4-chloro-butyl ester: (Scheme 1, (D)) Prepared as described for the example above. Analytical HPLC 1.46 min (89%). Mass Spec: 454.3 (MH$^+$).

EXAMPLE 5

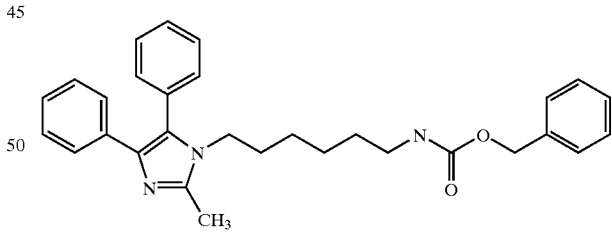

[6-(2-Methyl-4,5-diphenyl-imidazol-1-yl)-hexyl]-carbamic acid benzyl ester: (Scheme 1 (D)) Prepared as described for the example above. This compound was purified by preparative HPLC (YMC 30×100 mm (5 uM packing), 10% MeOH/90% water/01% TFA as mobile phase A, 90% MeOH/10%water/0.1% TFA as mobile phase B). $^1$H NMR (DMSO): δ1.067 (bs, 4H), 1.26 (t, 2H), 1.47 (t, 2H), 2.73 (s, 3H), 2.91 (q, 2H), 3.94 (t, 2H), 5.01 (s, 2H), 7.20 (m, 3H), 7.35 (m, 8H), 7.49 (m, 2H), 7.59 (d, J=6.69 mHz, 3H). Mass Spec: 468.17 (MH$^+$).

EXAMPLE 6

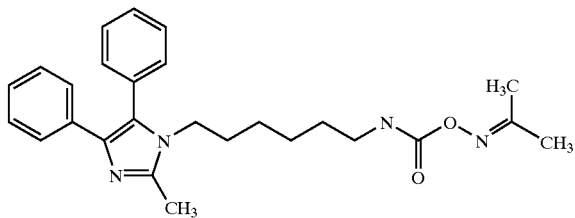

2-Propanone,O-[6-(2-methyl-4,5-diphenyl-1H-imidazol-1-yl)hexyl]amino]carbonyl]oxime: (Scheme 1 (D)) Prepared as described for the example above. $^1$H NMR (DMSO): δ1.11 (m, 4H), 1.30 (m, 2H), 1.50 (m, 2H), 1.92 (d, J=9.25 mHz, 6H), 2.74 (s, 3H), 2.96 (m, 2H), 3.94 (t, 2H), 7.29 (t, 1H), 7.39 (m, 2H), 7.41 (m, 3H), 7.49 (m, 2H), 7.61 (m, 2H). Mass Spec: 433.31 (MH$^+$).

EXAMPLE 7

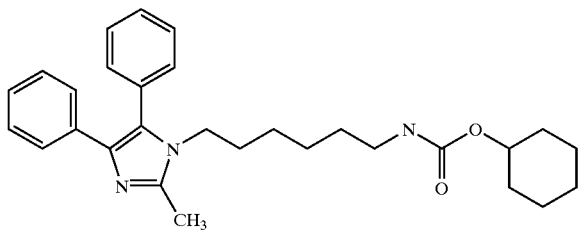

[6-(2-Methyl-4,5-diphenyl-imidazol-1-yl)-hexyl]-carbamic acid cyclohexyl ester: (Scheme 1 (D)) Prepared as described for the example above. Analytical HPLC 1.64 min (85%). Mass spec: 460.21 (MH$^+$).

EXAMPLE 8

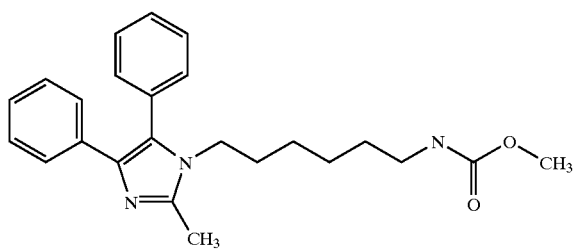

[6-(2-Methyl-4,5-diphenyl-imidazol-1-yl)-hexyl]-carbamic acid methyl ester: Prepared as described for the example above. Analytical HPLC 1.33 min (80%). Mass spec : 392.12 (MH$^+$).

EXAMPLE 9

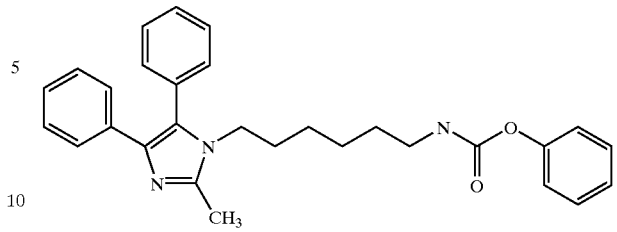

6-(2-Methyl-4,5-diphenyl-imidazol-1-yl)-hexyl]-carbamic acid phenyl ester: (Scheme 1 (D)) Prepared as described for the example above. Analytical HPLC 1.50 min (83%). Mass Spec: 454.15 (MH$^+$).

EXAMPLE 10

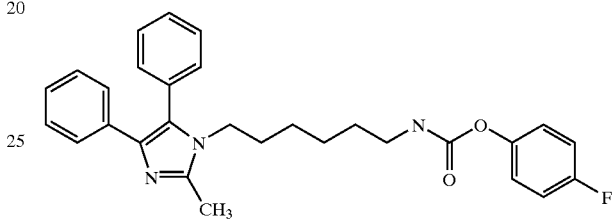

[6-(2-Methyl-4,5-diphenyl-imidazol-1-yl)-hexyl]-carbamic acid 4-fluoro-phenyl ester: (Scheme 1 (D)) Prepared as described for the example above. Analytical HPLC 1.52 min (97%). Mass Spec: 472.09 (MH$^+$).

EXAMPLE 11

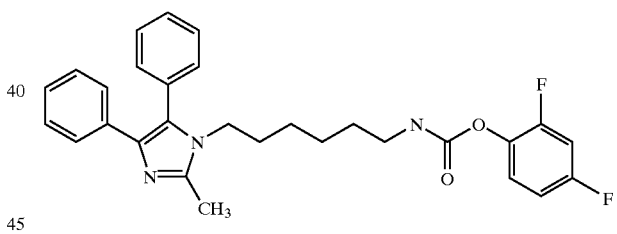

[6-(2-Methyl-4,5-diphenyl-imidazol-1-yl)-hexyl]-carbamic acid 2,4-difluoro-phenyl ester: (Scheme 1 (D)) Prepared as described for the example above. Analytical HPLC 1.54 min (96%). Mass Spec. 490.06 (MH$^+$).

EXAMPLE 12

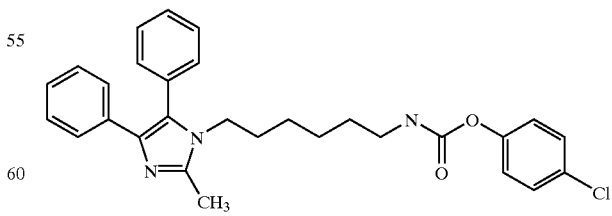

[6-(2-Methyl-4,5-diphenyl-imidazol-1-yl)-hexyl]-carbamic acid 4-chloro-phenyl ester: (Scheme 1 (D)) Prepared as described for the example above. Analytical HPLC 1.61 min (95%). Mass Spec: 488.02 (MH$^+$).

EXAMPLE 13

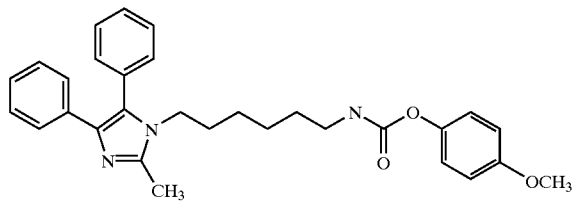

[6-(2-Methyl-4,5-diphenyl-imidazol-1-yl)-hexyl]-carbamic acid 4-methoxy-phenyl ester: (Scheme 1 (D)) Prepared as described for the example above. Analytical HPLC 1.51 min (96%). Mass Spec: 484.11 (MH$^+$).

EXAMPLE 14

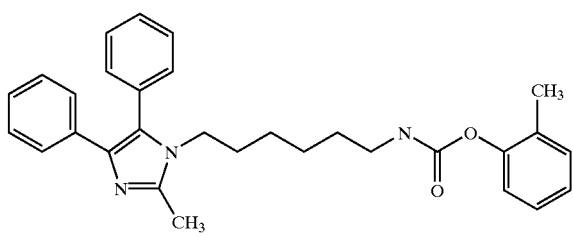

[6-(2-Methyl-4,5-diphenyl-imidazol-1-yl)-hexyl]-carbamic acid o-tolyl ester: (Scheme 1 (D)) Prepared as described for the example above. H Analytical HPLC 1.54 min (92%). Mass Spec: 468.11 (MH$^+$).

EXAMPLE 15

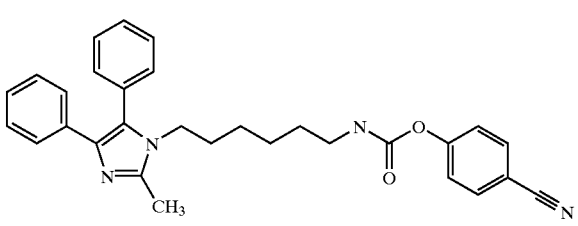

[6-(2-Methyl-4,5-diphenyl-imidazol-1-yl)-hexyl]-carbamic acid 4-cyano-phenyl ester: (Scheme 1 (D)) Prepared as described for the example above. Analytical HPLC 1.46 min (94%). Mass Spec: 479.08 (MH$^+$).

EXAMPLE 16

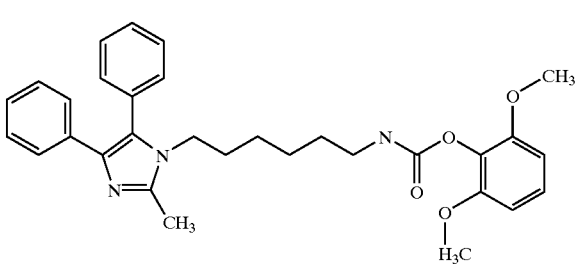

[6-(2-Methyl-4,5-diphenyl-imidazol-1-yl)-hexyl]-carbamic acid 2,6-dimethoxy-phenyl ester: (Scheme 1 (D)) Prepared as described for the example above. Analytical HPLC 1.43 min (94%). Mass Spec: 514.10 (MH$^+$).

EXAMPLE 17

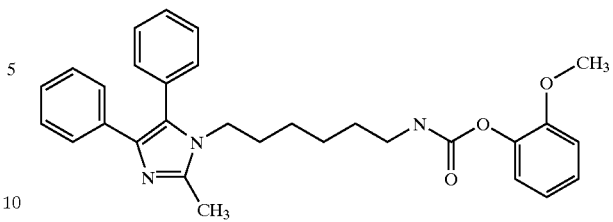

[6-(2-Methyl-4,5-diphenyl-imidazol-1-yl)-hexyl]-carbamic acid 2-methoxy-phenyl ester: (Scheme 1 (D)) Prepared as described for the example above. Analytical HPLC 1.48 min (99%). Mass Spec: 484.12 (MH$^+$).

EXAMPLE 18

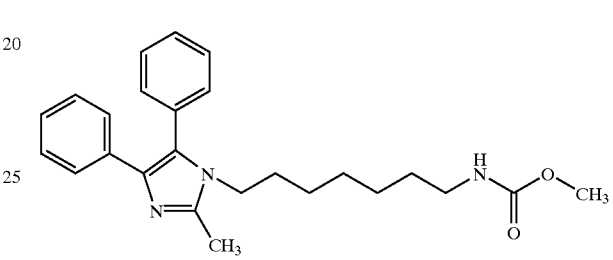

[7-(2-Methyl-4,5-diphenyl-imidazol-1-yl)-heptyl]-carbamic acid methyl ester: (Scheme 1 (D)) Prepared as described for the example above. Analytical HPLC 1.41 min (98%). Mass Spec: 406.32 (MH$^+$).

EXAMPLE 19

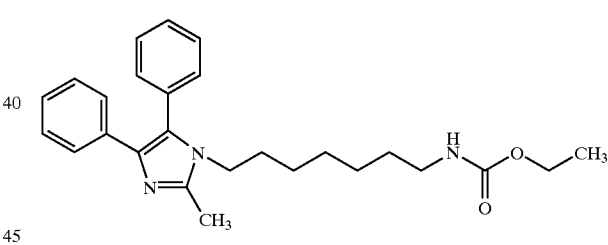

[7-(2-Methyl-4,5-diphenyl-imidazol-1-yl)-heptyl]-carbamic acid ethyl ester: (Scheme 1 (D)) Prepared as described for the example above. Analytical HPLC 1.49 min (95%). Mass Spec: 420.35 (MH$^+$).

EXAMPLE 20

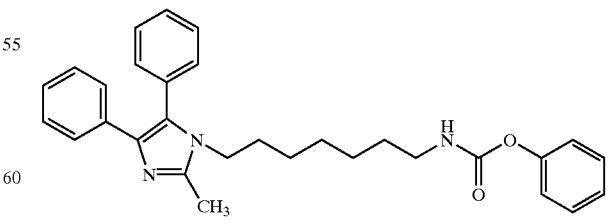

[7-(2-Methyl-4,5-diphenyl-imidazol-1-yl)-heptyl]-carbamic acid phenyl ester: (Scheme 1 (D)) Prepared as described for the example above. Analytical HPLC 1.58 min (99%). Mass Spec: 468.32 (MH$^+$).

EXAMPLE 21

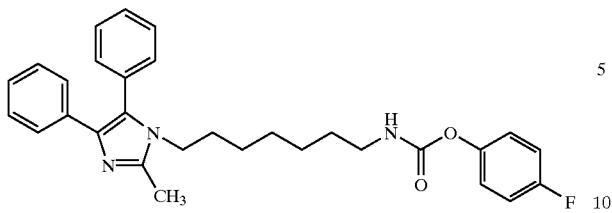

[7-(2-Methyl-4,5-diphenyl-imidazol-1-yl)-heptyl]-carbamic acid 4-fluoro-phenyl ester: (Scheme 1 (D)) Prepared as described for the example above. Analytical HPLC 1.60 min (98%). Mass Spec: 486.30 (MH$^+$).

EXAMPLE 22

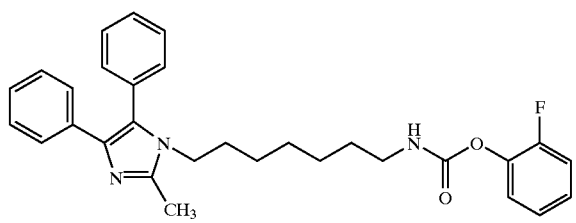

[7-(2-Methyl-4,5-diphenyl-imidazol-1-yl)-heptyl]-carbamic acid 2-fluoro-phenyl ester: (Scheme 1 (D)) Prepared as described for the example above. Analytical HPLC 1.58 min (96%). Mass Spec: 486.31 (MH$^+$).

EXAMPLE 23

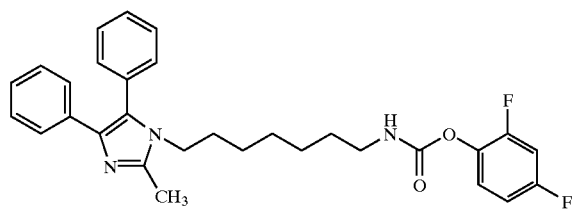

[7-(2-Methyl-4,5-diphenyl-imidazol-1-yl)-heptyl]-carbamic acid 2,4-difluoro-phenyl ester: (Scheme 1 (D)) Prepared as described for the example above. Analytical HPLC 1.61 min (90%). Mass Spec: 504.31 (MH$^+$).

EXAMPLE 24

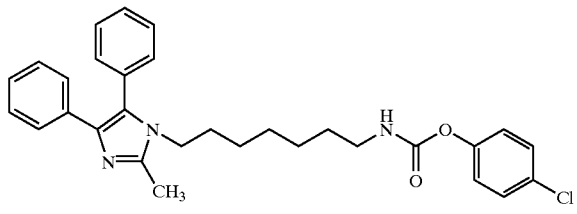

[7-(2-Methyl-4,5-diphenyl-imidazol-1-yl)-heptyl]-carbamic acid 4-chloro-phenyl ester: (Scheme 1 (D)) Prepared as described for the example above. Analytical HPLC 1.68 min (90%). Mass Spec: 502.29 (MH$^+$).

EXAMPLE 25

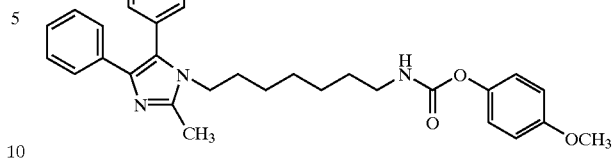

[7-(2-Methyl-4,5-diphenyl-imidazol-1-yl)-heptyl]-carbamic acid 4-methoxy-phenyl ester: (Scheme 1 (D)) Prepared as described for the example above. Analytical HPLC 1.59 min (90%). Mass Spec: 498.33 (MH$^+$).

EXAMPLE 26

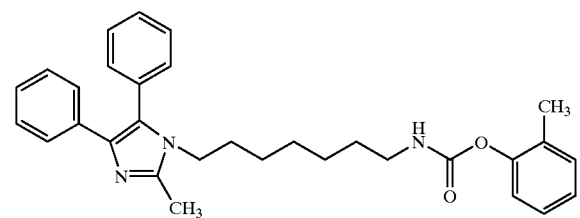

[7-(2-Methyl-4,5-diphenyl-imidazol-1-yl)-heptyl]-carbamic acid o-tolyl ester: (Scheme 1 (D)) Prepared as described for the example above. Analytical HPLC 1.63 min (90%). Mass Spec: 482.33 (MH$^+$).

EXAMPLE 27

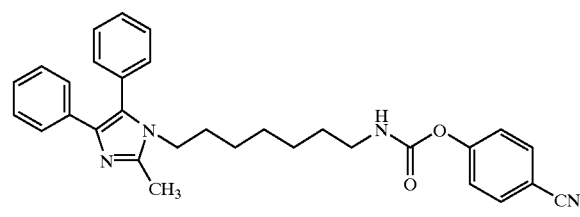

[7-(2-Methyl-4,5-diphenyl-imidazol-1-yl)-heptyl]-carbamic acid 4-cyano-phenyl ester: (Scheme 1 (D)) Prepared as described for the example above. Analytical HPLC 1.53 min (90%). Mass Spec: 493.31 (MH$^+$).

EXAMPLE 28

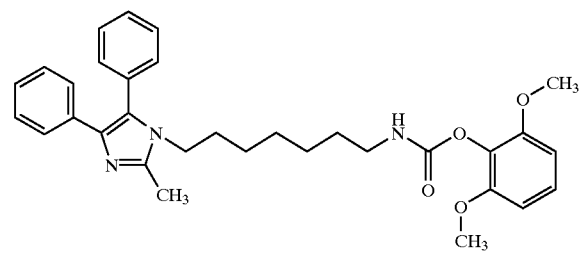

[7-(2-Methyl-4,5-diphenyl-imidazol-1-yl)-heptyl]-carbamic acid 2,6-dimethoxy-phenyl ester: (Scheme 1 (D)) Prepared as described for the example above. Analytical HPLC 1.53 min (96%). Mass Spec: 528.37 (MH$^+$).

EXAMPLE 29

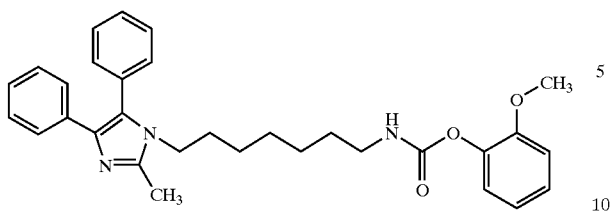

[7-(2-Methyl-4,5-diphenyl-imidazol-1-yl)-heptyl]-carbamic acid 2-methoxy-phenyl ester: (Scheme 1 (D)) Prepared as described for the example above. Analytical HPLC 1.57 min (90%). Mass Spec: 498.33 (MH$^+$).

EXAMPLE 30

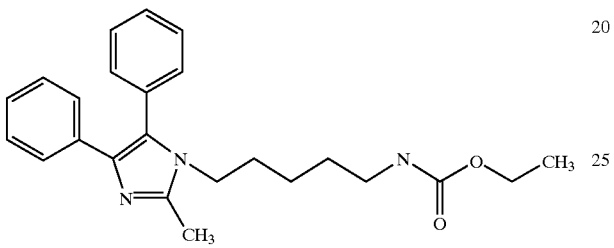

[5-(2-Methyl-4,5-diphenyl-imidazol-1-yl)-pentyl]-carbamic acid ethyl ester: (Scheme 1 (D)) Prepared as described for the example above. Analytical HPLC 1.36 min (98%). Mass Spec: 392.35 (MH$^+$).

EXAMPLE 31

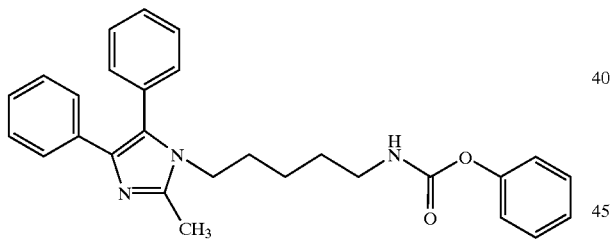

[5-(2-Methyl-4,5-diphenyl-imidazol-1-yl)-pentyl]-carbamic acid phenyl ester: (Scheme 1 (D)) Prepared as described for the example above. Analytical HPLC 1.48 min (97%). Mass Spec: 440.36 (MH$^+$).

EXAMPLE 32

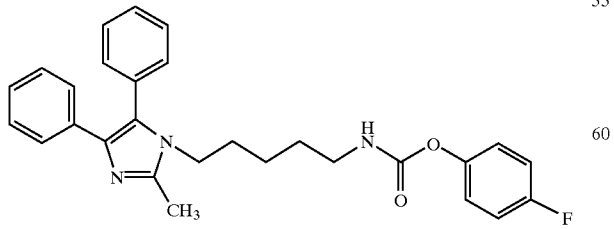

[5-(2-Methyl-4,5-diphenyl-imidazol-1-yl)-pentyl]-carbamic acid 4-fluoro-phenyl ester: (Scheme 1 (D)) Prepared as described for the example above. Analytical HPLC 1.51 min (97%). Mass Spec: 458.33 (MH$^+$).

EXAMPLE 33

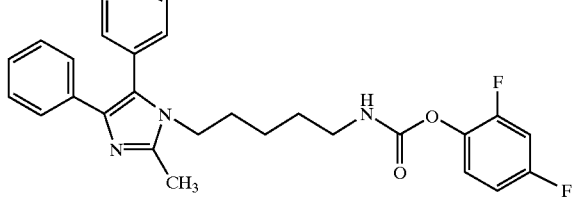

[5-(2-Methyl-4,5-diphenyl-imidazol-1-yl)-pentyl]-carbamic acid 2,4-difluoro-phenyl ester: (Scheme 1 (D)) Prepared as described for the example above. Analytical HPLC 1.52 min (95%). Mass Spec: 476.32 (MH$^+$).

EXAMPLE 34

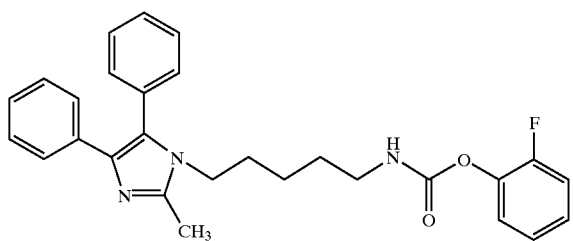

[5-(2-Methyl-4,5-diphenyl-imidazol-1-yl)-pentyl]-carbamic acid 2-fluoro-phenyl ester: (Scheme 1 (D)) Prepared as described for the example above. Analytical HPLC 1.48 min (98%). Mass Spec: 458.33 (MH$^+$).

EXAMPLE 35

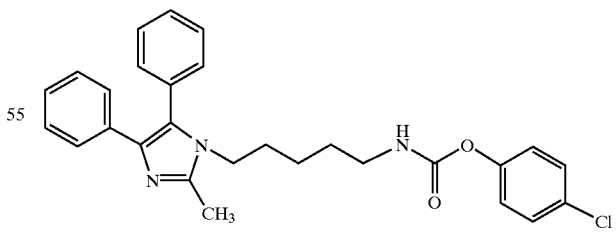

[5-(2-Methyl-4,5-diphenyl-imidazol-1-yl)-pentyl]-carbamic acid 4-chloro-phenyl ester: (Scheme 1 (D)) Prepared as described for the example above. Analytical HPLC 1.62 min (98%). Mass spec: 474.29 (MH$^+$).

EXAMPLE 36

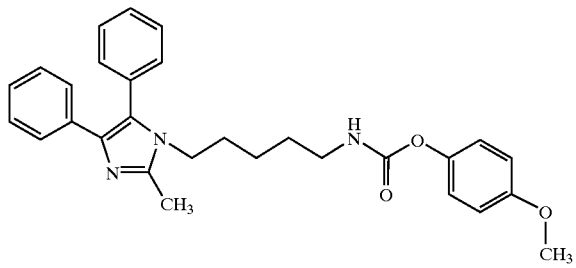

[5-(2-Methyl-4,5-diphenyl-imidazol-1-yl)-pentyl]-carbamic acid 4-methoxy-phenyl ester: (Scheme 1 (D)) Prepared as described for the example above. Analytical HPLC 1.49 min (99%). Mass Spec: 470.35 (MH+).

EXAMPLE 37

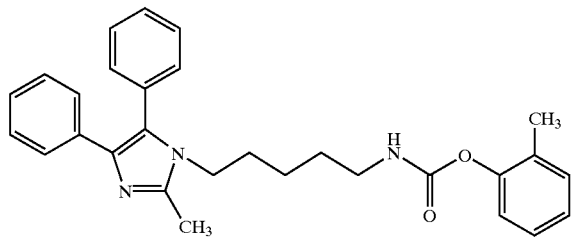

[5-(2-Methyl-4,5-diphenyl-imidazol-1-yl)-pentyl]-carbamic acid o-tolyl ester: (Scheme 1 (D)) Prepared as described for the example above. Analytical HPLC 1.56 min (95%). Mass Spec: 454.36 (MH+).

EXAMPLE 38

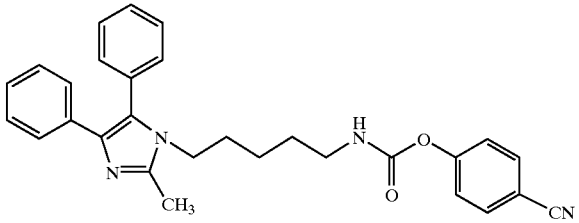

[5-(2-Methyl-4,5-diphenyl-imidazol-1-yl)-pentyl]-carbamic acid 4-cyano-phenyl ester: (Scheme 1 (D)) Prepared as described for the example above. Analytical HPLC 1.44 min (99%). Mass Spec: 465.32 (MH+).

EXAMPLE 39

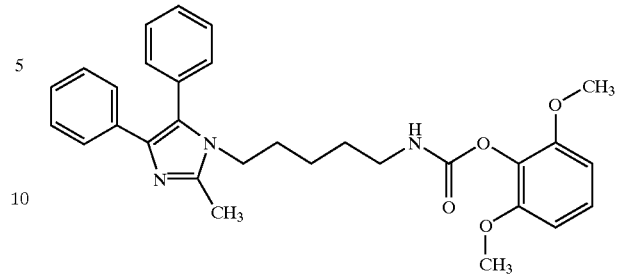

[5-(2-Methyl-4,5-diphenyl-imidazol-1-yl)-pentyl]-carbamic acid 2,6-dimethoxy-phenyl ester: (Scheme 1 (D)) Prepared as described for the example above. Analytical HPLC 1.44 min (99%). Mass Spec: 500.38 (MH+).

EXAMPLE 40

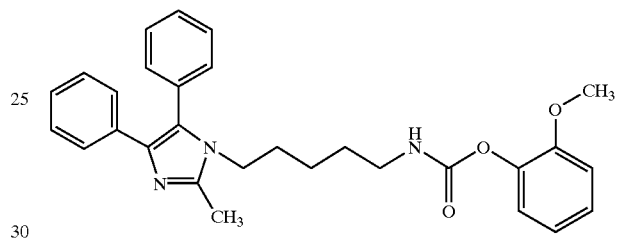

[5-(2-Methyl-4,5-diphenyl-imidazol-1-yl)-pentyl]-carbamic acid 2-methoxy-phenyl ester: (Scheme 1 (D)) Prepared as described for the example above. Analytical HPLC 1.46 min (97%). Mass Spec: 470.34 (MH+).

EXAMPLE 41

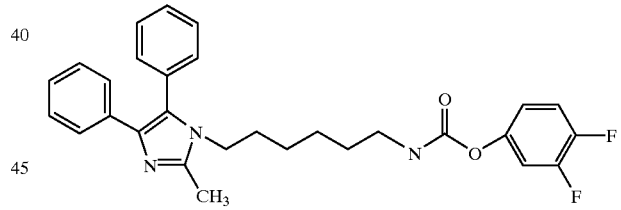

[6-(2-Methyl-4,5-diphenyl-imidazol-1-yl)-hexyl]-carbamic acid 3,4-difluoro-phenyl ester: (Scheme 1 (D)) Prepared as described for the example above. Analytical HPLC 1.55 min (84%). Mass Spec: 490.32 (MH+).

EXAMPLE 42

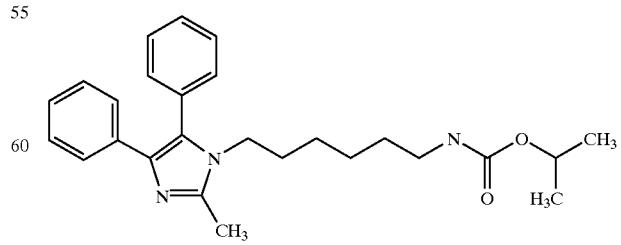

[6-(2-Methyl-4,5-diphenyl-imidazol-1-yl)-hexyl]-carbamic acid isopropyl ester: (Scheme 1 (D)) Prepared as described for the example above. Analytical HPLC 1.47 min (83%). Mass spec: 420.17 (MH+).

EXAMPLE 43

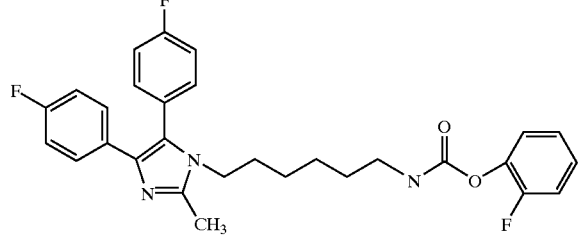

{6-[4,5-Bis-(4-fluoro-phenyl)-2-methyl-imidazol-1-yl]-hexyl}-carbamic acid 2-fluoro-phenyl ester: (Scheme 1 (D)) Prepared as described for the example above. Analytical HPLC 1.50 min (95%). Mass Spec: 508.29 (MH+).

EXAMPLE 44

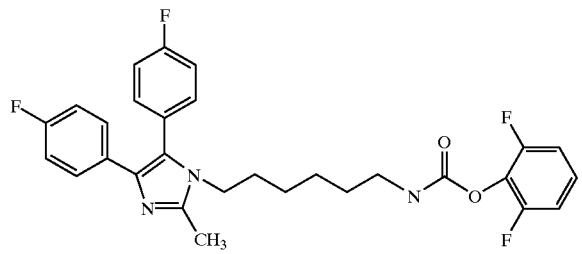

{6-[4,5-Bis-(4-fluoro-phenyl)-2-methyl-imidazol-1-yl]-hexyl}-carbamic acid 2,6-difluoro-phenyl ester: (Scheme 1 (D)) Prepared as described for the example above. Analytical HPLC 1.50 min (85%). Mass Spec: 526.31 (MH+).

EXAMPLE 45

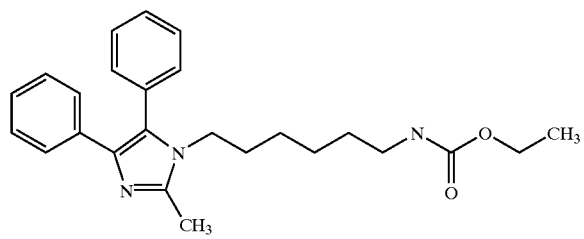

[6-(2-Methyl-4,5-diphenyl-imidazol-1-yl)-hexyl]-carbamic acid ethyl ester (Scheme 1 (D)) Prepared as described for the example above. Analytical HPLC 1.40 min (82%). Mass Spec: 406.15 (MH+).

EXAMPLE 46

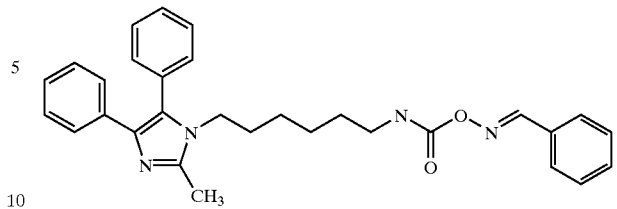

Benzaldehyde, O-[6-(2-methyl-4,5-diphenyl-1H-imidazol-1-yl)hexyl]amino]carbonyl]oxime: (Scheme 1 (D)) Prepared as described for the example above. Analytical HPLC 1.48 min (89%). Mass Spec: 481.26 (MH+).

EXAMPLE 47

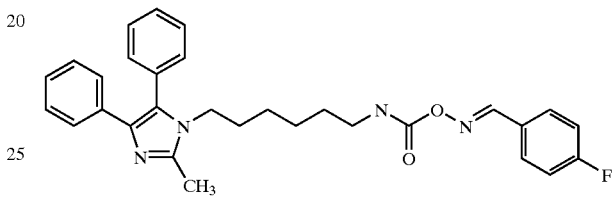

4-Fluorobenzaldehyde,O-[6-(2-methyl-4,5-diphenyl-1H-imidazol-1-yl)hexyl]amino]carbonyl]oxime: (Scheme 1 (D)) Prepared as described for the example above. Analytical HPLC 1.58 min (87%). Mass Spec: 499.32 (MH+).

EXAMPLE 48

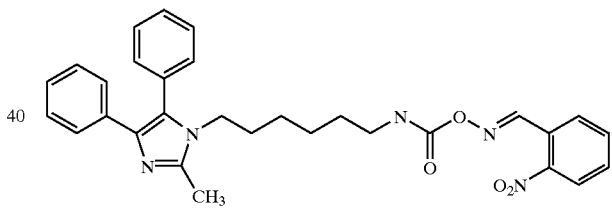

2-Nitrobenzaldehye, O-[6-(2-methyl-4,5-diphenyl-1H-imidazol-1-yl)hexyl]amino]carbonyl]oxime: (Scheme 1 (D)) Prepared as described for the example above. Analytical HPLC 1.56 min (95%). Mass Spec: 526.3 (MH+).

EXAMPLE 49

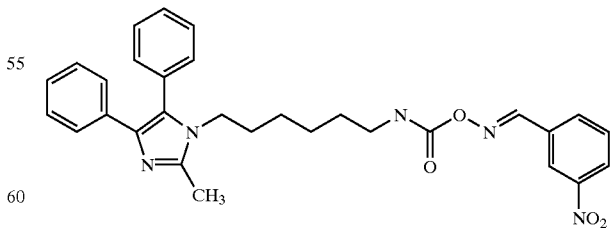

3-Nitrobenzaldehyde, O-[6-(2-methyl-4,5-diphenyl-1H-imidazol-1-yl)hexyl]amino]carbonyl]oxime: (Scheme 1 (D)) Prepared as described for the example above. Analytical HPLC 1.57 min (83%). Mass Spec: 526.32 (MH+).

EXAMPLE 50

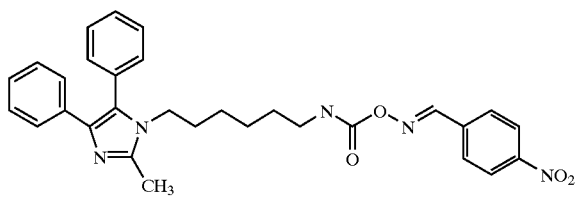

4-Nitrobenzaldehyde, O-[6-(2-methyl-4,5-diphenyl-1H-imidazol-1-yl)hexyl]amino]carbonyl]oxime: (Scheme 1 (D)) Prepared as described for the example above. Analytical HPLC 1.58 min (94%). Mass Spec: 526.29 (MH+).

EXAMPLE 51

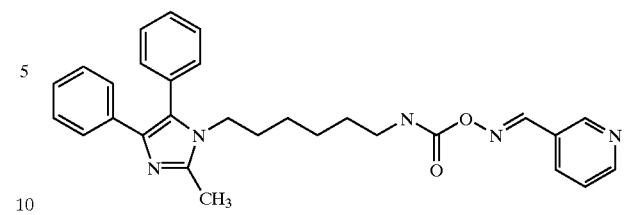

3-Pyridinecarboxaldehyde, O-[6-(2-methyl-4,5-diphenyl-1H-imidazol-1-yl)hexyl]amino]carbonyl]oxime: (Scheme 1 (D)) Prepared as described for the example above. Analytical HPLC 1.24 min (94%). Mass Spec: 482.26 (MH+).

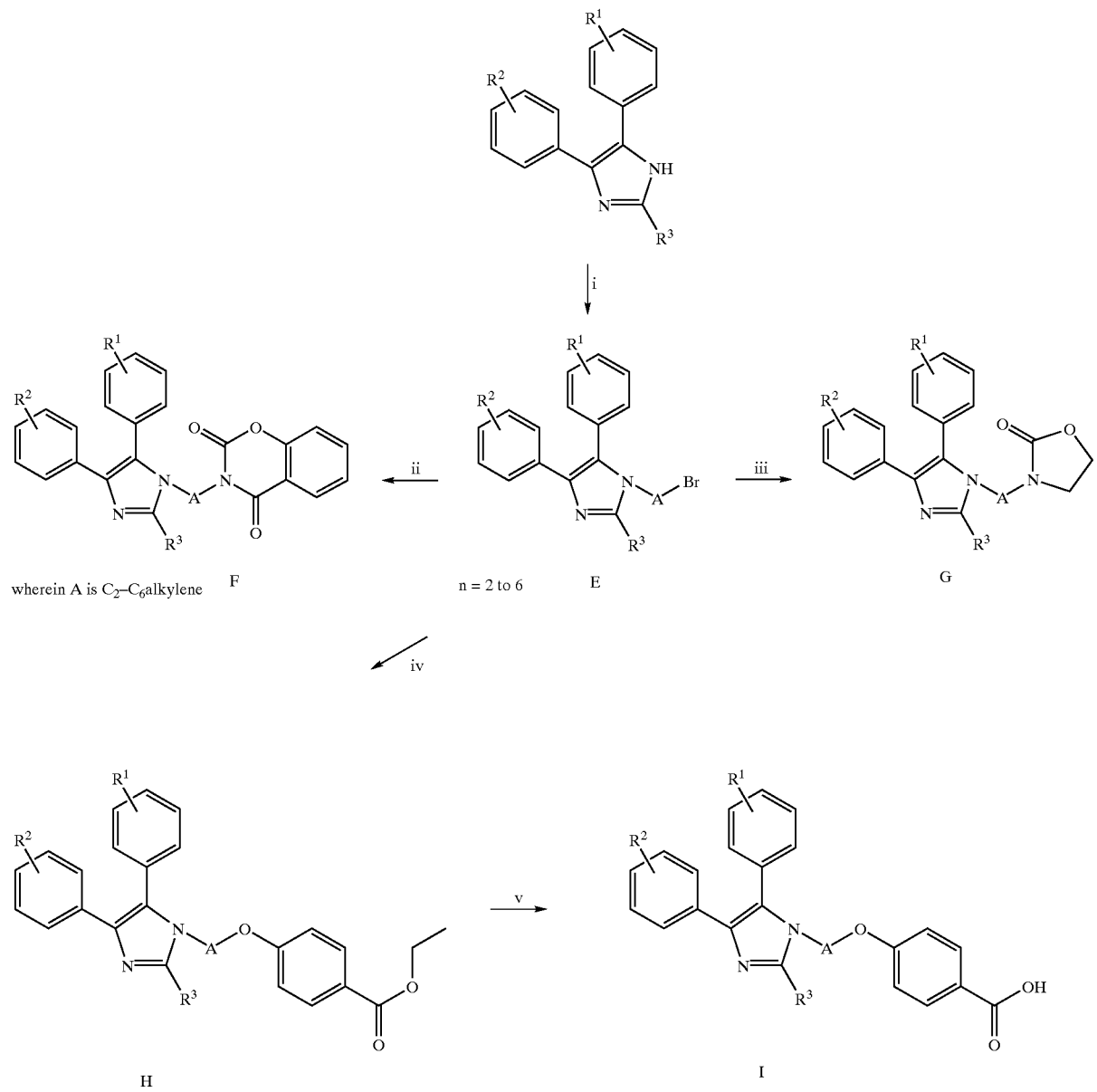

Scheme 2

-continued

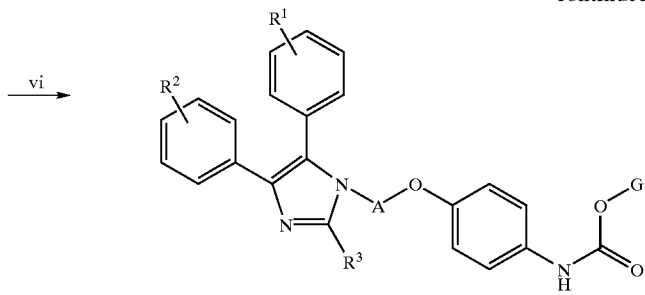

J

Reaction conditions: (i) dibromide, NaH, DMF, rt; (ii) 2 H-1,3-benz oxazine-2,4(3 H)-dione, K₂CO₃, DMF, 85° C.; (iii) 2-oxazolidone, NaH, DMF, rt; (iv) ethyl 4-hy droxybenzoate, K₂CO₃, DMF, 55° C.; (v) NaOH, EtOH, rt; (vi) (a) N₃P(O)(OPh)₂, Et₃N, toluene, 105° C., (b) GOH, 80° C.

The following Intermediates 14–20 may be used to synthesize Examples 52–74.

Intermediate 14

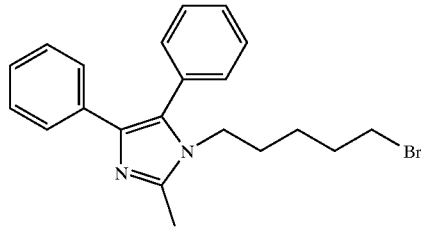

1-(5-Bromo-pentyl)-2-methyl-4,5-diphenyl-1H-imidazole: (Scheme 2 (E)) To a solution of 2-Methyl-4,5-diphenyl-1H-imidazole (2.0 g, 8.5 mmol) and 1,5-dibromopentane (3.01 g, 12.7 mmol) in DMF (100 mL) was added NaH (60% in mineral oil, 0.50 g, 12.7 mmol). The resulting mixture was stirred at rt for 1 hour, quenched by addition of water, extracted by CH₂Cl₂, washed by water, and then was dried over MgSO₄. After filtration and concentration in vacuo, the residue was purified by flash chromatography (SiO₂: EtOAc/Hexanes). This compound was obtained as a pale yellow oil (2.2 g, 5.7 mmol, 67% yield): $^1$H NMR (DMSO): δ1.20 (m, 2H), 1.47 (m, 2H), 1.64 (m, 2H), 2.41 (s, 3H), 3.45 (t, 2H), 3.72 (t, 2H), 7.16 (m, 3H), 7.31 (m, 4H), 7.55 (t, 3H). Mass Spec: 384.57 (MH⁺).

Intermediate 15

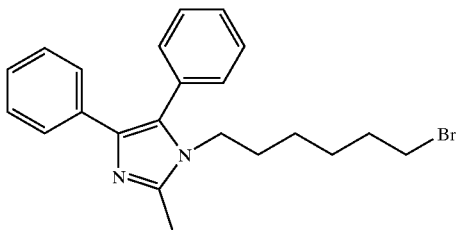

1-(6-Bromo-hexyl)-2-methyl-4,5-diphenyl-1H-imidazole: (Scheme 2 (E)) Prepared as described for the example above. $^1$H NMR (DMSO): δ1.2 (m, 4H), 1.5 (m, 2H), 1.75 (m, 2H), 2.5 (s, 3H), 3.4 (t, 2H), 3.69 (t, 2H), 7.14 (m, 3H), 7.36 (m, 4H), 7.516 (m, 3H). Mass Spec: 399.14 (MH⁺).

Intermediate 16

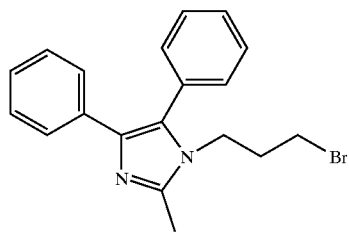

1-(3-Bromo-propyl)-2-methyl-4,5-diphenyl-1H-imidazole: (Scheme 2 (E)) Prepared as described for the example above. $^1$H NMR (DMSO): δ1.99 (m, 2H), 2.43 (s, 3H), 3.39 (t, 2H), 3.88 (t, 2H), 7.17 (m, 3H). 7.35 (m, 4H), 7.53 (m, 3H), Mass Spec: 356.59 (MH⁺).

Intermediate 17

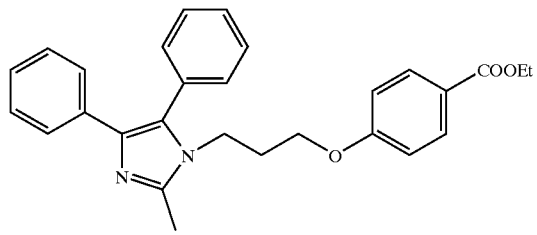

4-[3-(2-Methyl-4,5-diphenyl-imidazol-1-yl)-propoxy]-benzoic acid ethyl ester: (Scheme 2 (H)) To a solution of 1-(3-Bromo-propyl)-2-methyl-4,5-diphenyl-1H-imidazole (0.80 g, 2.2 mmol) and ethyl 4-hydroxybenzoate (1.20 g, 7.2 mmol) in DMF (30 mL) was added K₂CO₃ (0.40 g, 2.9 mmol). The resulting mixture was stirred at 55° C. for 1 hour, quenched by addition of water, extracted by EtOAc, washed by water, and then was dried over MgSO₄. After filtration and concentration in vacuo, the residue was purified by flash chromatography (SiO₂: EtOAc/Hexanes). This compound was obtained as a pale yellow gum (0.92 g, 2.0 mmol, 94% yield): $^1$H NMR (DMSO): δ1.32 (t, 3H), 1.85 (m, 2H), 2.402 (s, 3H), 3.87 (m, 4H), 4.28 (q, 2H), 6.89 (d, J=8.82 Hz, 2H), 7.143 (m, 3H), 7.36 (m, 4H), 7.46 (m, 3H), 7.82 (d, J=8.85 mHz, 2H). Mass spec: 441.28 (MH⁺).

Intermediate 18

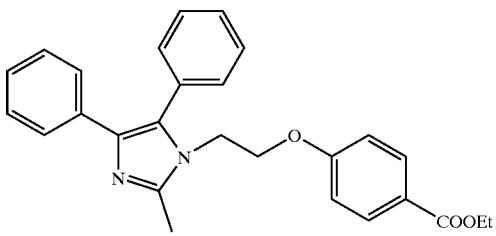

4-[2-(2-Methyl-4,5-diphenyl-imidazol-1-yl)-ethoxy]-benzoic acid ethyl ester: (Scheme 2 (H)) Prepared as described for the example above. ¹H NMR (DMSO): δ1.31 (t, 3H), 2.5 (s, 3H), 4.07 (m, 2H), 4.15 (m, 2H), 4.26 (q, 2H), 6.91 (d, J=8.88 mHz, 2H), 7.16 (m, 3H), 7.33 (d, J=7.56 mHz, 2H), 7.41 (m, 2H), 7.53 (m, 3H), 7.85 (d, J=8.85 mHz, 2H).

Intermediate 19

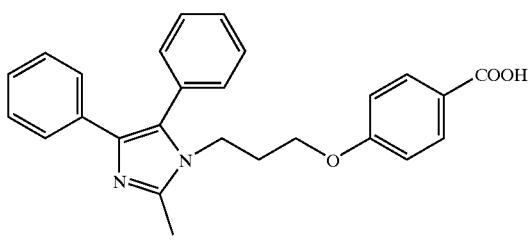

4-[3-(2-Methyl-4,5-diphenyl-imidazol-1-yl)-propoxy]-benzoic acid: (Scheme 2 (I)) To a solution of 4-[3-(2-Methyl-4,5-diphenyl-imidazol-1-yl)-propoxy]-benzoic acid ethyl ester (0.80 g, 1.8 mmol) in EtOH (20 mL) was added NaOH (10 N, 4.0 mL, 40.0 mmol). The resulting mixture was stirred at rt for 3 hours, diluted with water, acidified to pH~1 using 1N HCl, extracted by CH₂Cl₂, and then was dried over MgSO₄. After filtration and concentration in vacuo, the residue was purified by flash chromatography (SiO₂: MeOH/CH₂Cl₂). This compound was obtained as a white dry foam in HCl salt form (0.80 g, 1.8 mmol, 99% yield): ¹H NMR (DMSO): δ1.93 (m, 2H), 2.67 (s, 3H), 3.97 (t, 2H), 4.13 (t, 2H), 6.85 (d, J=8.82 mHz,2H), 7.33 (s, 5H), 7.43 (m, 2H), 7.55 (m, 3H), 7.86 (d, J=8.82 mHz, 2H), 12.64 (b, 1H).

Intermediate 20

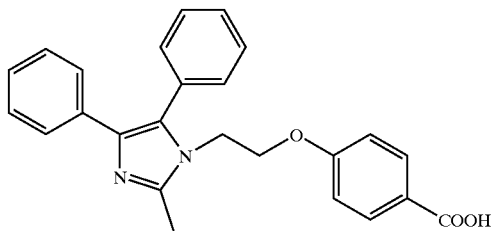

4-[2-(2-Methyl-4,5-diphenyl-imidazol-1-yl)-ethoxyl-benzoic acid: (Scheme 2 (I)) Prepared as described for the example above. ¹H NMR (DMSO): δ2.82 (s, 3H), 4.19 (m, 2H), 4.39 (m, 2H), 6.93 (d, J=8.85 mHz, 2H), 7.359 (m, 5H), 7.54 (m, 2H), 7.61 (m, 3H), 7.86 (d, J=8.76 mHz, 2H), 12.685 (b, 1H).

EXAMPLE 52

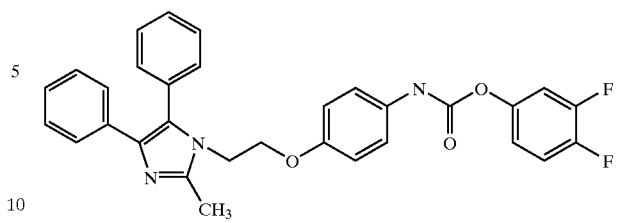

{4-[2-(2-Methyl-4,5-diphenyl-imidazol-1-yl)-ethoxy]-phenyl}-carbamic acid 3,4-difluoro-phenyl ester: (Scheme 2 (J)) To a suspension of 4-[2-(2-Methyl-4,5-diphenyl-imidazol-1-yl)-ethoxy]-benzoic acid (0.10 g, 0.23 mmol) in a mixture of Et₃N (0.09 g, 0.88 mmol) and toluene (2 mL) was added azide (0.1 g, 0.35 mmol). The resultant mixture was stirred at r.t. for 10 min. and then at 108° C. under N₂ for 45 min. After the mixture was cooled to r.t., 3,4-difluorophenol (0.10 g, 1.0 mmol) was added. The reaction mixture was stirred at r.t. for 10min and then at 80° C. for 1 h. The mixture was diluted with EtOAc, washed with H₂O. After filtration and concentration in vacuo, the residue was purified by preparative HPLC (YMC 30×100 mm (5 uM packing), 10% MeOH/90% water/01% TFA as mobile phase A, 90% MeOH/10%water/0.1% TFA as mobile phase B). This compound was obtained as a white solid (0.082 g, 0.13 mmol, 55% yield): ¹H NMR (DMSO): δ2.83 (s, 3H), 4.06 (t, 2H), 4.39 (t, 2H), 6.82 (d, J=7.05 mHz, 2H), 7.29 (m, 2H), 7.32 (m, 2H), 7.45 (m, 4H), 7.52 (m, 4H), 7.61 (m, 3H). Mass Spec: 526.22 (MH+).

EXAMPLE 53

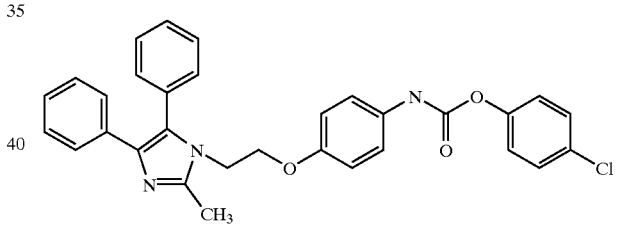

{4-[2-(2-Methyl-4,5-diphenyl-imidazol-1-yl)-ethoxy]-phenyl}-carbamic acid 4-chloro-phenyl ester: (Scheme 2 (J)) Prepared as described for the example above. ¹H NMR (DMSO): δ2.83 (s, 3H), 4.07 (t, 2H), 4.39 (t, 2H), 6.83 (d, J=10.3 mHz, 2H), 7.24 (d, J=10.3 mHz, 2H), 7.30 (m, 2H), 7.36 (m, 5H), 7.46 (d, J=12.6 mHz, 2H), 7.59 (m, 2H), 7.61 (m, 3H). Mass Spec: 524.18 (MH+).

EXAMPLE 54

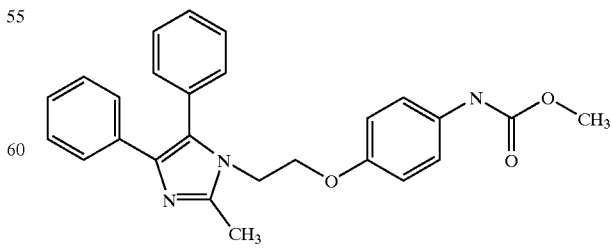

{4-[2-(2-Methyl-4,5-diphenyl-imidazol-1-yl)-ethoxy]-phenyl}-carbamic acid methyl ester: (Scheme 2 (J)) Prepared as described for the example above. ¹H NMR (DMSO): δ2.82 (s, 3H), 3.62 (s, 3H), 4.05 (t, 2H), 4.38 (t, 2H), 6.77 (d, J=7 mHZ, 2H), 7.28 (m, 1H), 7.31 (m, 3H), 7.36 (m, 3H), 7.53 (m, 2H), 7.61 (m, 3H), 9.45 (b, 1H). Mass Spec: 428.24 (MH+).

EXAMPLE 55

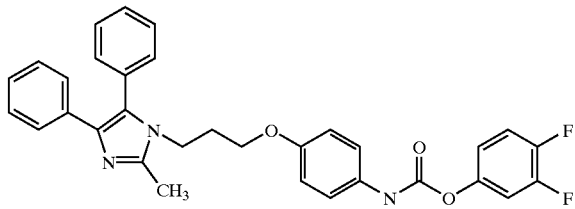

{4-[3-(2-Methyl-4,5-diphenyl-imidazol-1-yl)-propoxy]-phenyl}-carbamic acid 3,4-difluoro-phenyl ester: (Scheme 2 (J)) Prepared as described for the example above. Analytical HPLC 1.66 min (95%). Mass Spec: 540.25 (MH+).

EXAMPLE 56

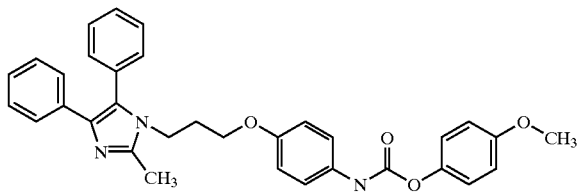

{4-[3-(2-Methyl-4,5-diphenyl-imidazol-1-yl)-propoxy]-phenyl}-carbamic acid 4-methoxy-phenyl ester: (Scheme 2 (J)) Prepared as described for the example above. Analytical HPLC 1.52 min (98%). Mass Spec: 534.35 (MH+).

EXAMPLE 57

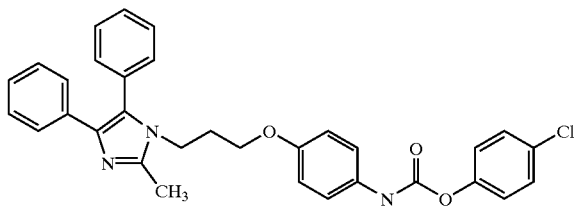

{4-[3-(2-Methyl-4,5-diphenyl-imidazol-1-yl)-propoxy]-phenyl}-carbamic acid 4-chloro-phenyl ester: (Scheme 2 (J)) Prepared as described for the example above. Analytical HPLC 1.62 min (81%). Mass Spec: 538.22 (MH+).

EXAMPLE 58

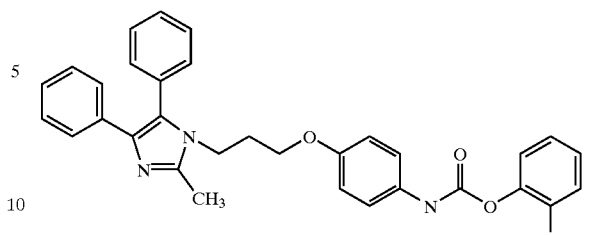

{4-[3-(2-Methyl-4,5-diphenyl-imidazol-1-yl)-propoxy]-phenyl}-carbamic acid 2-methoxy-phenyl ester: (Scheme 2 (J)) Prepared as described for the example above. Analytical HPLC 1.49 min (95%). Mass Spec: 534.43 (MH+).

EXAMPLE 59

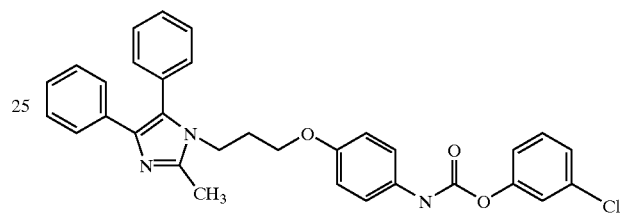

{4-[3-(2-Methyl-4,5-diphenyl-imidazol-1-yl)-propoxy]-phenyl}-carbamic acid 3-chloro-phenyl ester: (Scheme 2 (J)) Prepared as described for the example above. Analytical HPLC 1.71 min (90%). Mass Spec: 538.23 (MH+).

EXAMPLE 60

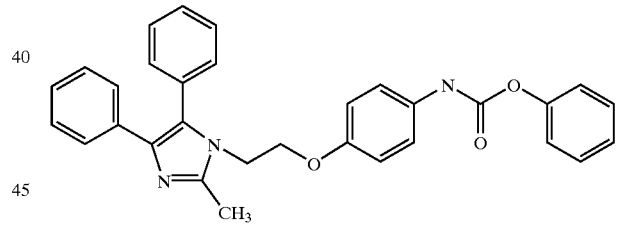

{4-[2-(2-Methyl-4,5-diphenyl-imidazol-1-yl)-ethoxy]-phenyl}-carbamic acid phenyl ester: (Scheme 2 (J)) Prepared as described for the example above. Analytical HPLC 1.58 min (84%). Mass Spec: 490.25 (MH+).

EXAMPLE 61

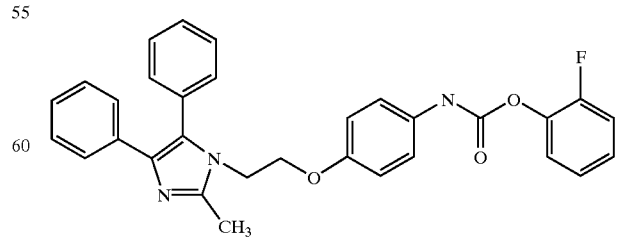

{4-[2-(2-Methyl-4,5-diphenyl-imidazol-1-yl)-ethoxy]-phenyl}-carbamic acid 2-fluoro-phenyl ester: (Scheme 2 (J))

Prepared as described for the example above. Analytical HPLC 1.49 min (92%). Mass Spec: 508.23 (MH+).

EXAMPLE 62

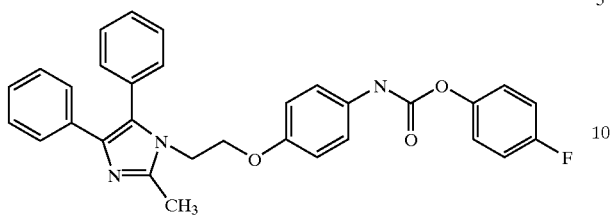

{4-[2-(2-Methyl-4,5-diphenyl-imidazol-1-yl)-ethoxy]-phenyl}-carbamic acid 4-fluoro-phenyl ester: (Scheme 2 (J)) Prepared as described for the example above. Analytical HPLC 1.53 min (92%). Mass Spec: 508.23 (MH+).

EXAMPLE 63

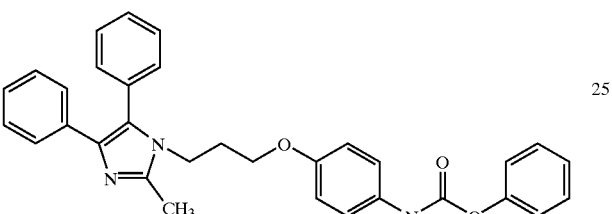

{4-[3-(2-Methyl-4,5-diphenyl-imidazol1-yl)-propoxy]-phenyl}-carbamic acid phenyl ester: (Scheme 2 (J)) Prepared as described for the example above. Analytical HPLC 1.53 min (95%). Mass Spec: 504.39 (MH+).

EXAMPLE 64

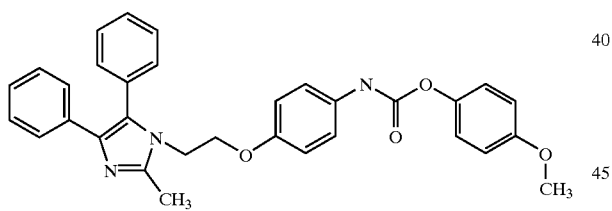

{4-[2-(2-Methyl-4,5-diphenyl-imidazol-1-yl)-ethoxy]-phenyl}-carbamic acid 4-methoxy-phenyl ester: (Scheme 2 (J)) Prepared as described for the example above. Analytical HPLC 1.50 min (94%). Mass Spec: 520.24 (MH+).

EXAMPLE 65

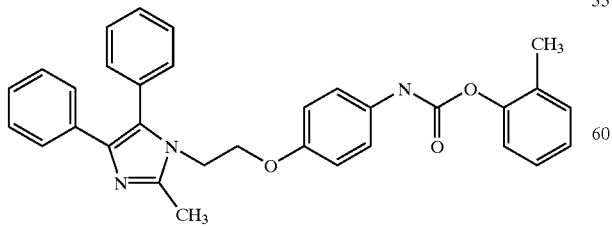

{4-[2-(2-Methyl-4,5-diphenyl-imidazol-1-yl)-ethoxy]-phenyl}-carbamic acid o-tolyl ester: (Scheme 2 (J)) Prepared as described for the example above. Analytical HPLC 1.54 min (92%). Mass Spec: 504.25 (MH+).

EXAMPLE 66

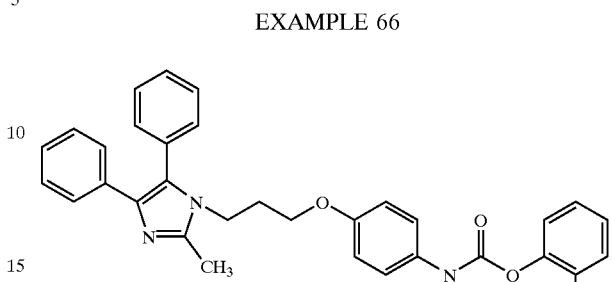

{4-[3-(2-Methyl-4,5-diphenyl-imidazol-1-yl)-propoxy]-phenyl}-carbamic acid 2-fluoro-phenyl ester: (Scheme 2 (J)) Prepared as described for the example above. Analytical HPLC 1.52 min (95%). Mass Spec: 522.32 (MH+).

EXAMPLE 67

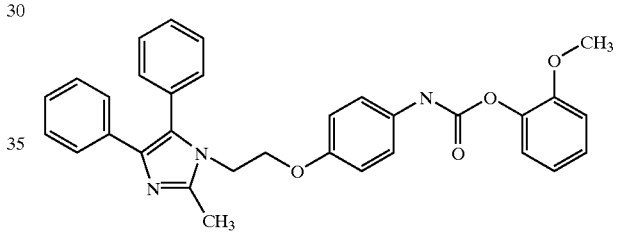

{4-[2-(2-Methyl-4,5-diphenyl-imidazol-1-yl)-ethoxy]-phenyl}-carbamic acid 2-methoxy-phenyl ester: (Scheme 2 (J)) Prepared as described for the example above. Analytical HPLC 1.46 min (97%). Mass Spec: 520.25 (MH+).

EXAMPLE 68

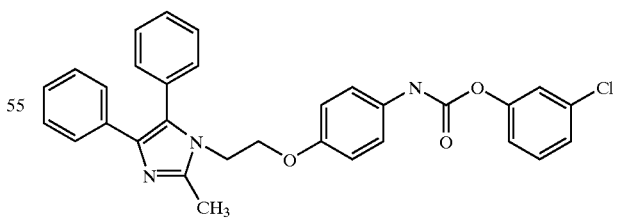

{4-[2-(2-Methyl-4,5-diphenyl-imidazol-1-yl)-ethoxy]-phenyl}-carbamic acid 3-chloro-phenyl ester: (Scheme 2 (J)) Prepared as described for the example above. Analytical HPLC 1.61 min (97%). Mass Spec: 524.18 (MH+).

EXAMPLE 69

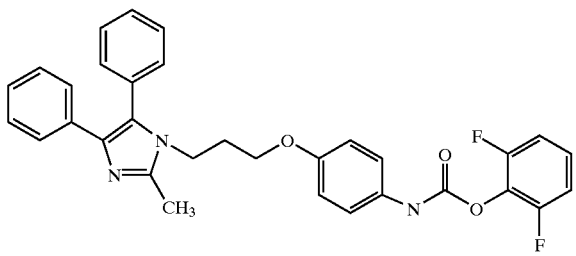

{4-[3-(2-Methyl-4,5-diphenyl-imidazol-1-yl)-propoxy]-phenyl}-carbamic acid 2,6-difluoro-phenyl ester: (Scheme 2 (J)) Prepared as described for the example above. Analytical HPLC 1.58 min (90%). Mass Spec: 540.25 (MH+). Notebook number:

EXAMPLE 70

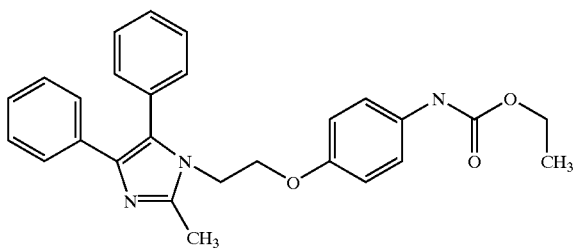

{4-[2-(2-Methyl-4,5-diphenyl-imidazol-1-yl)-ethoxy]-phenyl}-carbamic acid ethyl ester: (Scheme 2 (J)) Prepared as described for the example above. Analytical HPLC 1.45 min (72%). Mass Spec: 442.25 (MH+).

Scheme 3

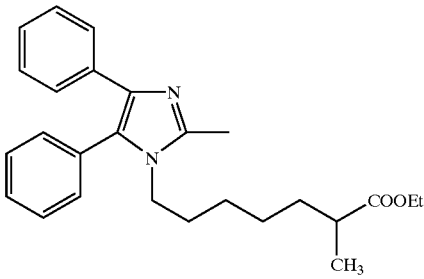

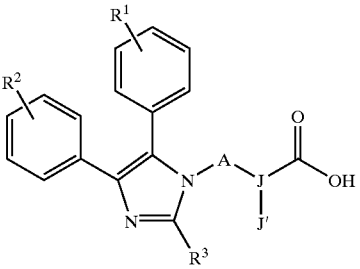

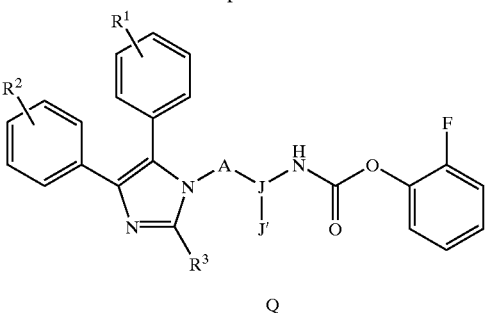

Reaction conditions: (i) [(CH$_3$)$_3$Si]$_2$NNa, THF, R$_5$I, -78° C. to rt; (ii) NaOH, MeOH, Reflux; (iii) (a) N$_3$P(O)(OPh)$_2$, Et$_3$N, toluene, 108° C., (b) 2-fluorophenol, 100° C.

The following Intermediates 21–24 may be used to synthesize Examples 75–77.

Intermediate 21

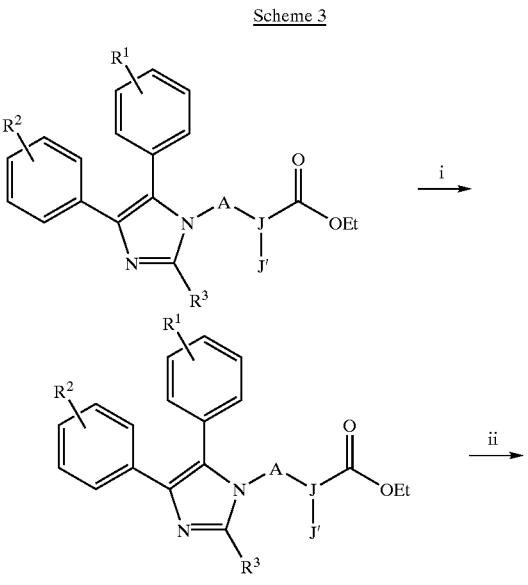

2-Methyl-7-(2-methyl-4,5-diphenyl-imidazol-1-yl)-heptanoic acid ethyl ester: (Scheme 3 (O)) Sodium bis(trimethylsilyl)amide (1M in THF) (3.0 ml, 3.0 mmole) was added dropwise to a solution of starting material 7-(2-Methyl-4,5-diphenyl-imidazol-1-yl)-heptanoic acid ethyl ester (1 g, 2.5 mmole) in anhydrous THF (10 ml) at −78° C. under Nitrogen. After addition, the reaction was let stirred 2 minutes, then Iodomethane (0.06 ml, 0.96 mmole) was added slowly at −78° under Nitrogen. The reaction mixture was let stirred at −78° C. for 1 hr, then warming up to room temperature and let stirred for 18 hrs. The next day, analysis by TLC indicated consumption of starting material. The reaction was quenched with aqueous Ammonium Chloride (10 ml). The aqueous layer was extracted with Ethyl Acetate (3×25 ml). The organic layers obtained were combined, dried over Sodium Sulfate and filtered. The resultant filtrate was concentrated in vacuo. Purification by flash column chromatography using Hexane/Ethyl Acetate (4:1) gave rise to product (150 mg, 45%). $^1$H NMR (CDCl$_3$): δ1.09 (d, J=6.95 mHz, 6H), 1.15 (t, 3H), 1.51 (m, 2H), 2.32 (m, 1H), 2.50 (s, 3H), 3.70 (t, 2H), 4.11 (q, 2H), 7.25 (m, 3H), 7.32 (m, 2H), 7.45 (m, 5H), $^{13}$C NMR (CDCl$_3$): δ13.7, 14.3, 17.1, 26.4, 26.6, 30.3, 33.4, 39.4, 43.8, 60.2, 125.9, 126.5, 128.0, 128.4, 128.5, 129.0, 131.1, 131.8, 134.8, 136.3, 144.0, 176.6. Anal. Calcd. for C$_{26}$H$_{32}$N$_2$O$_2$·0.25 H$_2$O: C, 76.34; H, 8.01; N, 6.85. Found: C, 76.38; H, 8.13; N, 6.83. Mass Spec: 405.29 (MH+).

Intermediate 22

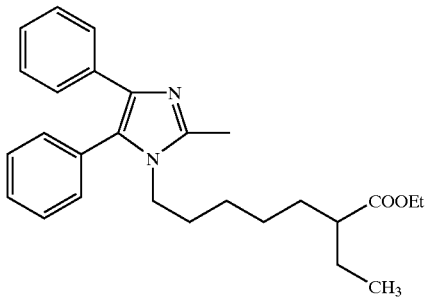

2-Ethyl-7-(2-methyl-4,5-diphenyl-imidazol-1-yl)-heptanoic acid ethyl ester: (Scheme 3 (O)) This compound was obtained using the procedures as described above. The following scales and reagents were used: 7-(2-Methyl-4,5-diphenyl-imidazol-1-yl)-heptanoic acid ethyl ester (390 mg, 1 mmole), Sodium bis(trimethylsilyl)amide (1M in THF) (1.2 ml, 1.2 mmole), Iodoethane (0.4 ml, 779.8 mg, 5 mmole), anhydrous THF (10 ml). Product was obtained (100 mg, 24%). $^1$H NMR (CDCl$_3$): δ0.88 (t, 3H), 1.23 (m, 4H), 1.33 (t, 3H), 1.54 (m, 4H), 1.68 (b, 1H), 2.04 (s, 1H), 2.17 (m, 1H), 2.49 (s, 3H), 3.709 (t, 2H), 4.15 (m, 2H), 7.19 (m, 3H), 7.42 (m, 3H), 7.46 (m, 4H). $^{13}$C NMR (CDCl$_3$): δ12.0, 13.9, 14.6, 25.7, 26.6, 27.0, 30.5, 31.9, 44.0, 47.3, 60.2, 126.1, 126.7, 128.2, 128.7, 129.2, 131.3. Anal. Calcd. for C$_{27}$H$_{34}$N$_2$O$_2$: C, 77.48; H, 8.19; N, 6.69. Found: C, 77.34; N, 8.01; N, 6.56. Mass Spec: 419.32 (MH+).

Intermediate 23

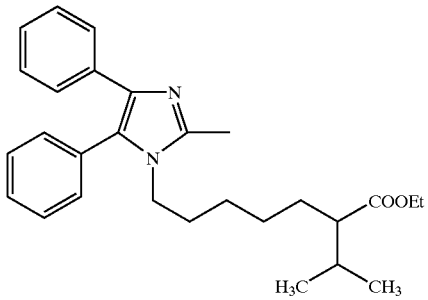

2-Isopropy -7-(2-methyl-4,5-diphenyl-imidazol-1-yl)-heptanoic acid ethyl ester: (Scheme 3 (O)) Sodium bis(trimethylsilyl)amide (1M in THF) (1.2 ml, 1.2 mmole) was added dropwise to a solution 7-(2-Methyl-4,5-diphenyl-imidazol-1-yl)-heptanoic acid ethyl ester (390 mg, 1 mmole) in anhydrous THF (10 ml) at −78° C. under Nitrogen. The reaction solution was let stirred warming up to room temperature during a period of 3 hrs. The reaction solution was cooled to −78° C., and 2-Iodopropane (499.97 ul, 849.95 mg, 5 mmole) was added in dropwise. The reaction was let stirred at room temperature for 1 hr, then at 50° C. for 1 hr. Analysis by TLC indicated consumption of starting material. The reaction was worked-up using the procedures as described above. Crude material was purified by flash column chromatography using Hexane/Ethyl Acetate (4:1) to give product (80 mg, 18.5%). $^1$H NMR CDCl$_3$): δ0.89 (t, 6H), 1.14 (m, 4H), 1.249 (t, 3H), 1.49 (m, 3H), 1.81 (m, 2H), 1.989 (m, 1H), 2.49 (s, 3H), 3.70 (t, 2H), 4.1 (m, 2H), 7.15 (m, 1H), 7.31 (t, 2H), 7.40 (m, 2H), 7.445 (m, 5H). $^{13}$C NMR (CDCl$_3$): δ13.7, 14.4, 20.2, 20.4, 26.5, 27.2, 29.3, 30.3, 30.7, 43.8, 52.6, 59.9, 125.9, 126.5, 128.0, 128.3, 128.5, 129.0, 131.0, 131.8, 134.8, 136.3, 144.0, 175.6. Anal. Calcd. for C$_{28}$H$_{36}$N$_2$O$_2$·0.21 H$_2$O: C, 77.07, H, 8.41; N, 6.42. Found: C, 77.08; H, 8.84; N, 6.22. Mass Spec: 433.2 (MH+).

Intermediate 24

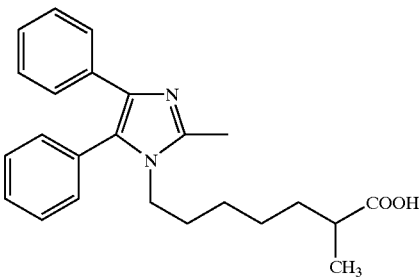

2-Methyl-7-(2-methyl-4,5-diphenyl-imidazol-1-yl)-heptanoic acid: (Scheme 3 (P)) A solution of starting material 2-Methyl-7-(2-methyl-4,5-diphenyl-imidazol-1-yl)-heptanoic acid ethyl ester (130 mg, 0.32 mmole) in Methanol (5 ml) and Sodium Hydroxide (64 mg, 1.61 mmole) was let stirred under reflux for 18 hrs. The next day, the reaction was let cooled to room temperature and concentrated in vacuo. The residue was diluted with water, and acidified with Hydrochloric Acid (3N). The aqueous layer was extracted with Dichloromethane (3×10 ml). The organic layers were combined, dried over Sodium Sulfate and filtered. The resultant filtrate was concentrated in vacuo to afford product as a white solid (120 mg, 99%). Mass Spec: 377 (MH+).

Intermediate 25

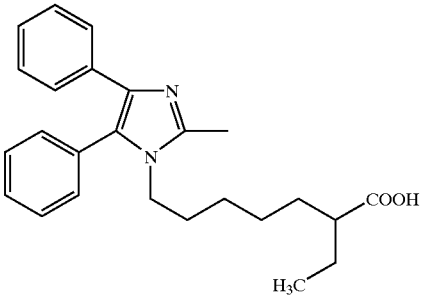

2-Ethyl-7-(2-methyl-4,5-diphenyl-imidazol-1-yl)-heptanoic acid: (Scheme 3 (P)) This compound was obtained using the procedures as described above. The following scales and reagents were used: 2-Ethyl-7-(2-methyl-4,5-diphenyl-imidazol-1-yl)-heptanoic acid ethyl ester (100 mg, 0.24 mmole), Sodium hydroxide (2N, 0.5 mL, 1.0 mmole), Methanol (5 mL). Product was obtained as white solid (90 mg, 96%). Mass Spec: 391.25 (MH+).

Intermediate 26

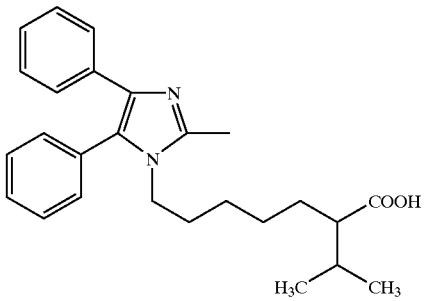

2-Ethyl-7-(2-methyl-4,5-diphenyl-imidazol-1-yl)-heptanoic acid: (Scheme 3 (P)) This compound was obtained using the procedures as described above. The following scales and reagents were used: 2-Isopropyl-7-(2-methyl-4,5-diphenyl-imidazol-1-yl)-heptanoic acid ethyl ester (80 mg, 0.18 mmole), Sodium hydroxide (2N, 0.5 mL, 1.0 mmole), Methanol (5 mL). Product was obtained as white solid (46 mg, 64%). Mass Spec: 405.37 (MH+).

EXAMPLE 71

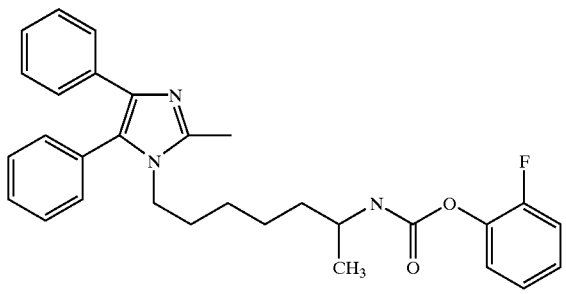

[1-Methyl-6-(2-methyl-4,5-diphenyl-imidazol-1-yl)-hexyl]-carbamic acid 2-fluoro-phenyl ester: (Scheme 3 (Q)) Diphenylphosphoryl Azide (0.083 ml, 0.38 mmole) was added to a suspension of starting material 2-methyl-7-(2-methyl-4,5-diphenyl-imidazol-1-yl)-heptanoic acid (120 mg, 0.32 mmole) and Triethylamine (0.14 ml, 1.005 mmole) in Toluene (5 ml) at room temperature. The reaction mixture was let stirred at room temperature for 10 minutes under Nitrogen, then at 108° C. for 90 minutes. The reaction was let cooled to room temperature, to which 2-Fluorophenol (0.03 ml, 0.038 g, 0.338 mmole) was added. The reaction mixture was let stirred at room temperature for 30 minutes, then at 100° C. for 18 hrs. The next day, analysis by TLC (Dichloromethane/Ethyl Acetate 3:1) indicated consumption of starting material. The reaction was let cooled to room temperature, where the solvent was removed by rotorvap. The crude material was purified by flash column chromatography using Dichloromethane/Ethyl Acetate (6:1 to 3:1). Product was obtained (110 mg, 71%). $^1$H NMR (CDCl$_3$): δ1.21 (d, J=8.75 mHz, 6H), 1.35 (m, 2H), 1.51 (m, 2H), 2.50 (s, 3H), 3.71 (m, 3H), 4.93 (b, 1H), 7.18 (m, 6H), 7.32 (m, 2H), 7.46 (m, 6H). $^{13}$C NMR (CDCl$_3$): δ13.7, 21.1, 25. 2, 30.3, 36.7, 43.7, 47.5, 116.5, 116.650, 124.132, 124.325, 125.943, 126.520, 128.027, 128.347, 128.509, 129.018, 131.101, 131.796, 134.8,136.4, 138.6, 144.1,153.0, 153.7, 155.6. Anal. Calcd. for C$_{30}$H$_{32}$FN$_3$O$_2$.0.42 H$_2$O: C, 73.06; H, 6.71; N, 8.52. Found: C, 73.24; H, 6.82; N, 8.29. Mass Spec: 486.27 (MH+).

EXAMPLE 72

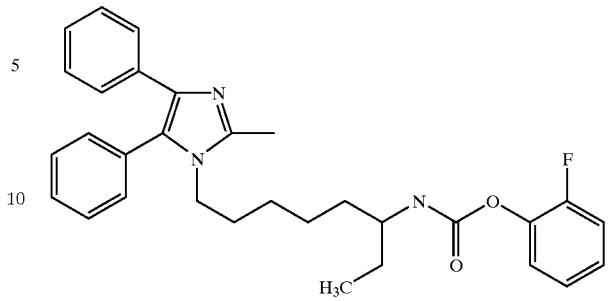

[1-Ethyl-6-(2-methyl-4,5-diphenyl-imidazol-1-yl)-hexyl]-carbamic acid 2-fluoro-phenyl ester: (Scheme 3 (Q)) This compound was prepared using the procedures as described above. The following scales and reagents were used: Starting material 2-ethyl-7-(2-methyl-4,5-diphenyl-imidazol-1-yl)-heptanoic acid (90 mg, 0.23 mmole), Diphenylphosphoryl Azide (0.060 ml, 0.276 mmole), Triethylamine (0.14 ml, 1.005 mmole), and 2-Fluorophenol (30 ul, 0.338 mmole). After purification by flash column chromatography, product was obtained (90 mg, 18%). $^1$H NMR (CDCl$_3$): δ0.96 (t, 3H), 1.24 (m, 5H), 1.51 (m, 2H), 1.54 (m, 3H), 2.50 (s, 3H), 3.72 (t, 2H), 4.77 (d, J=9.28 mHz, 1H), 7.16 (m, 7H), 7.342 (m, 2H), 7.45 (m, 5H). $^{13}$C NMR (CDCl$_3$): δ10.2, 13.7, 25.1, 26.3, 28.2, 30.3, 34.7, 43.7, 53.076, 116.466, 116.650, 124.108, 124.276, 125.937, 126.527, 128.015, 128.348, 128.483, 129.001, 131.1, 131.8, 134.8, 136.3, 144.1, 153.5. Anal. Calcd. for C$_{31}$H$_{34}$FN$_3$O$_2$: C, 74.52; H, 6.86; N, 8.41. Found: C, 74.43; H, 6.98; N, 8.32. Mass Spec: 500.34 (MH+).

EXAMPLE 73

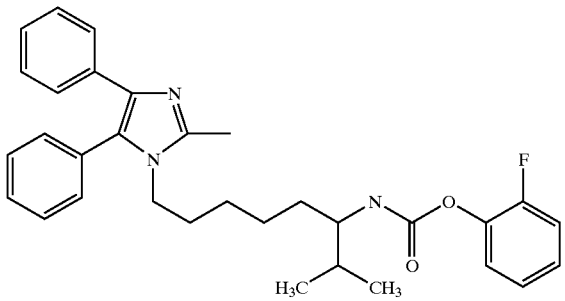

[1-Isopropyl-6-(2-methyl-4,5-diphenyl-imidazol-1-yl)-hexyl]-carbamic acid 2-fluoro-phenyl ester: (Scheme 3 (Q)) This compound was obtained using the procedures as described above. The following scales and reagents were used: Starting material 2-isopropyl-7-(2-methyl-4,5-diphenyl-imidazol-1-yl)-heptanoic acid (45.8 mg, 0.113 mmole), Diphenylphosphoryl Azide (0.029 ml, 0.135 mmole), Triethylamine (0.049 ml, 0.351 mmole), and 2-Fluorophenol (0.012 ml, 0.135 mmole). After purification by flash column chromatography, product was obtained (27.5 mg, 47%). $^1$H NMR (CDCl$_3$): δ0.95 (m, 6H), 1.27 (m, 5H), 1.53 (m, 2H), 1.73 (m, 2H), 2.50 (s, 3H), 3.56 (m, 1H), 3.73 (t, 2H), 4.75 (d, J=10 mHz, 1H), 7.19 (m, 7H), 7.33 (m, 2H), 7.45 (m, 5H). $^{13}$C NMR (CDCl$_3$): δ13.7, 17.5, 19.3, 25.5, 26.3, 30.3, 32.2, 32.3, 43.7, 56.7, 116.5, 116.6, 124.1, 124.3, 124.3, 125.9, 126.4, 126.5, 128.0, 128.3, 128.5, 128.8, 131.1, 131.8, 134.8, 136.4, 144.1, 153.7. Anal. Calcd. for C$_{32}$H$_{36}$FN$_3$O$_2$·0.59 H$_2$O: C, 73.31; H, 7.15; N, 8.01. Found: C, 73.45; 7.20; N, 7.61. Mass Spec: 514.2 (MH+).

Scheme 4

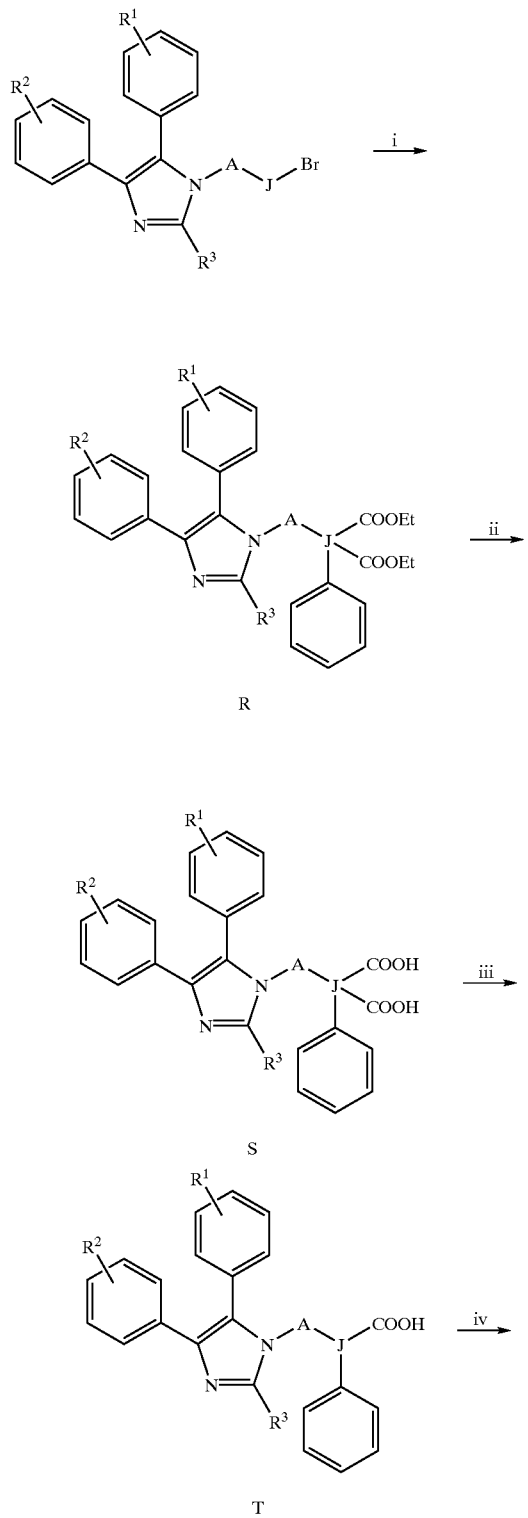

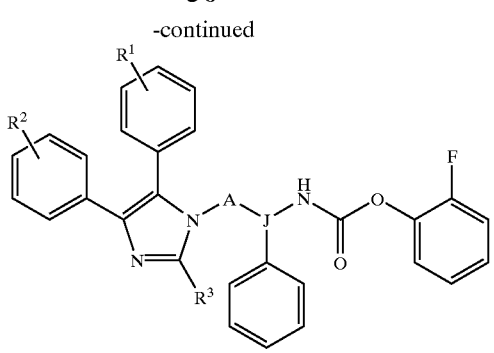

U

Reaction conditions: (i) (a) NaH, DMF, rt, (b) diethyl phenyl malo nate, 45–50° C. (ii) NaOH, THF, 80° C.; (iii) CH$_3$COOH, reflux; (iv) (a) N$_3$P(O)(OPh)$_2$, Et$_3$N, toluene, 108° C., (b) 2-fluorophenol, 100° C.

The following Intermediates 27–29 may be used to synthesize Example 78.

Intermediate 27

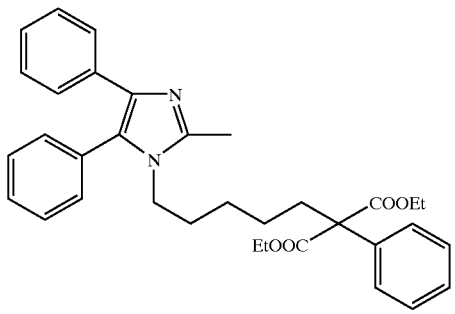

2-[5-(2-Methyl-4,5-diphenyl-imidazol-1-yl)-pentyl]-2-phenyl]-malonic acid diethyl ester: (Scheme 4 (R)) A solution of star[]ting material 1-(5-bromo-pentyl)-2-methyl-4,5-diphenyl-1H-imidazole (0.5 g, 1.3 mmole) in DMF (5 ml) was added to a suspension of Sodium Hydride (63 mg, 1.56 mmole) in DMF (5 ml) at room temperature under Nitrogen. The reaction suspension was let stirred for 30 minutes at room temperature. Diethyl Phenyl Malonate (0.29 ml, 313.5 mg, 1.3 mmole) was added to the reaction suspension dropwise at room temperature under nitrogen. The reaction mixture was let stirred at 45–50° C. for 48 hrs. Analysis by TLC indicated only a trace of starting material remained. The reaction was let cooled to room temperature, then poured into saturated Sodium Chloride solution. The aqueous layer was extracted with Ethyl Acetate (3×25 ml). The organic layers were combined and washed with water (1×30 ml). The organic layer was separated, dried over Sodium Sulfate and filtered. The filtrate was concentrated in vacuo. The crude material was purified by flash column chromatography using Ethyl Acetate/Toluene (2.5:7.5). Product was obtained as a colorless oil (650 mg, 93%). $^1$H NMR (CDCl$_3$): δ1.12 (m, 4H), 1.20 (t, 6H), 1.47 (m, 2H), 2.16 (t, 2H), 2.46 (s, 3H), 3.66 (t, 2H), 4.22 (m, 4H), 7.15 (m, 1H), 7.26 (m, 4H), 7.32 (m, 5H), 7.43 (m, 5H). $^{13}$C NMR (CDCl$_3$): δ13.7, 14.0, 24.2, 26.8, 30.2, 35.7, 43.8, 61.5, 62.5, 125.9, 126.5, 127.5, 127.9, 128.1, 128.2, 128.3, 128.5, 129.0, 131.0, 144.1, 170.6. Anal. Calcd. for $C_{34}H_{38}N_2O_4 \cdot 0.34$ Toluene: C, 76.77; H, 7.20; N, 4.91. Found: C, 76.64; H, 7.27; N, 4.78. Mass Spec: 539.29 (MH+).

Intermediate 28

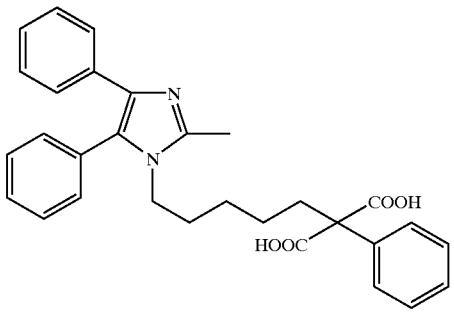

2-[5-(2-Methyl-4,5-diphenyl-imidazol-1-yl)-pentyl]-2-phenyl-malonic acid: (Scheme 4 (S)) A solution of starting material 2-[5-(2-methyl-4,5-diphenyl-imidazol-1-yl)-pentyl]-2-phenyl-malonic acid diethyl ester (630 mg, 1.17 mmole) in THF (18 ml) and Sodium hydroxide (2N) (8 ml) was let stirred at 80° C. for 18 hrs. The next day, analysis by TLC indicated no significant change in the reaction. The THF solvent was removed by rotorvap. The residue was diluted in Methanol (20 ml). The reaction solution was let stirred under reflux for 2 hrs. Analysis by TLC indicated consumption of starting material. The organic solvent was removed by rotorvap. The residue was diluted with water (20 ml). The aqueous layer was extracted Diethyl Ether (2×20 ml). The organic layers were combined and extracted with Sodium Hydroxide (10%) (2×10 ml). The basic aqueous layers were combined and acidified with Hydrochloric acid (3N) to pH=1, then extracted with dichloromethane (2×20 ml). The organic layers were combined, dried over Sodium Sulfate and filtered. The resultant filtrate was concentrated in vacuo to provide product as a white solid (580 mg, quantitative yield). Mass Spec: 483.54 (MH+).

Intermediate 29

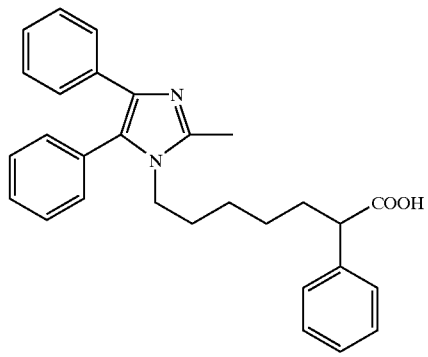

7-(2-Methyl-4,5-diphenyl-imidazol-1-yl)-2-phenyl-heptanoic acid: (Scheme 4 (T)) A solution of starting material 2-[5-(2-methyl-4,5-diphenyl-imidazol-1-yl)-pentyl]-2-phenyl-malonic acid (580 mg, 1.32 mmole)) in glacial Acetic Acid (20 ml) was let stirred under reflux for 18 hrs. The next day, the reaction was let cooled to room temperature and concentrated in vacuo. Product was obtained (398.6 mg, 77.7%). $^1$H NMR (CDCl$_3$): δ1.11 (b, 4H), 1.42 (bd, 2H), 1.59 (m, 1H), 1.96 (m, 1H), 2.55 (s, 3H), 3.43 (t, 1H), 3.96 (t, 2H), 7.199 (m, 3H), 7.27 (m, 7H), 7.39 (m, 2H), 7.45 (m, 3H), 11.857 (b, 1H), $^{13}$C NMR (CDCl$_3$): δ6 12.0, 21.4, 26.1, 26.8, 29.5, 29.7, 33.1, 44.2, 52.2, 127.0, 127.2, 127.4, 128.0, 128.4, 128.4, 128.5, 129.1, 129.3, 129.5, 130.6, 131.0, 133.0, 139.8, 144.1, 175.8, 177.7. Mass Spec: 439.24 (MH+).

EXAMPLE 74

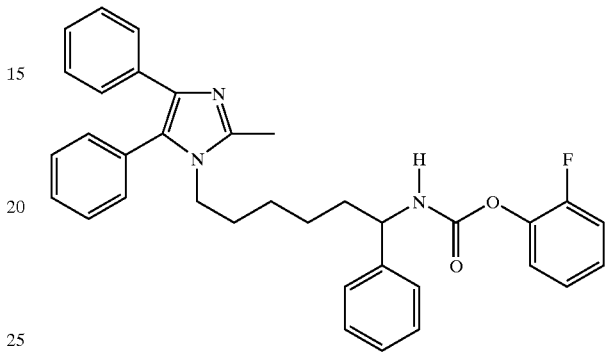

[6-(2-Methyl-4,5-diphenyl-imidazol-1-yl)-1-phenyl-hexyl]-carbamic acid 2-fluoro-phenyl ester: (Scheme 4 (U)) Diphenylphosphoryl Azide (0.083 ml, 0.38 mmole) was added to a suspension of starting material 7-(2-Methyl-4,5-diphenyl-imidazol-1-yl)-2-phenyl-heptanoic acid (140 mg, 0.32 mmole) and Triethylamine (0.14 ml, 1.005 mmole) in Toluene (5 ml) at room temperature. The reaction mixture was let stirred at room temperature for 10 minutes under Nitrogen, then at 108° C. for 90 minutes. The reaction was let cooled to room temperature, to which 2-Fluorophenol (0.03 ml, 0.038 g, 0.338 mmole) was added. The reaction mixture was let stirred at room temperature for 10 minutes, then at 100° C. for 18 hrs. The next day, analysis by TLC (Dichloromethane/Ethyl Acetate 3:1) indicated consumption of starting material. The reaction was let cooled to room temperature, where the solvent was removed by rotorvap. The crude material was purified by flash column chromatography using dichloromethane/Ethyl Acetate (6:1 to 3:1). Product was obtained (58 mg, 33.1%). $^1$H NMR (CDCl$_3$): δ1.18 (t, 3H), 1.27 (t, 2H), 1.497 (t, 2H), 2.47 (s, 3H), 3.70 (t, 2H), 4.63 (q, 1H), 5.38 (d, J=8.16 mHz, 1H), 7.18 (m, 7H), 7.37 (m, 7H), 7.44 (m, 5H). $^{13}$C NMR (CDCl3): δ13.6, 25.4, 26.1, 30.2, 36.0, 43.6, 55.7, 116.5, 116.7, 124.1, 124.3, 124.3, 126.0, 126.4, 126.5, 127.7, 128.0, 128.3, 128.5, 128.8, 129.0, 131.0, 131.7, 134.7, 136.3, 141.6, 144.1, 153.0. Anal. Calcd. for $C_{35}H_{34}FN_3O_2 \cdot 0.42$ H$_2$O: C, 75.71; H, 6.32; N, 7.57. Found: C, 75.75; H, 6.49; N, 7.50. Mass Spec: 548.27 (MH+).

Determination of FAAH Activity

Homogenates of crude membranes were prepared from H4 cells that express transfected human FAAH (H4-FAAH cells). Briefly, cells were grown in DMEM supplemented with 10% FBS and Geneticin at a final concentration of 500 μg/ml(Gibco BRL, Rockville, Md.). Confluent cultures of H4-FAAH cells were rinsed twice with phosphate-buffered saline [138 mM NaCl, 4.1 mM KCl, 5.1 mM Na$_2$PO$_4$, 1.5 mM KH$_2$PO$_4$ (pH 7.5), 37° C.] and incubated for 5–10 min. at 4° C. in lysis buffer [1 mM sodium bicarbonate]. Cells were transferred from plates to polypropylene tubes (16×100 mm), homogenized and centrifuged at 32,000×g for 30 min.

Pellets were resuspended by homogenization in lysis buffer and centrifuged at 32,000×g for 30 min. Pellets were resuspended in lysis buffer (15–20 μg protein/ml) then stored at −80° C. until needed. On the day of an experiment, membranes were diluted to 2.67 μg protein/ml in 125 mM Tris-Cl, pH 9.0

Activity of FAAH was measured using a modification of the method described by Omeir et al., 1995 (Life Sci 56:1999, 1995). Membrane homogenates (240 ng protein) were incubated at room temperature for one hour with 1.67 nM anandamide [ethanolamine 1-$^3$H] (American Radiolabeled Chemical Inc., St Louis, Mo.) and 10 μM anandamide (Sigma/RBI, St. Louis, Mo.) in the absence and presence of inhibitors. The reaction was stopped by the addition of 1 volume of a solution of methanol and dichloroethane (1:1). The mixture was shaken and then centrifuged at 1000×g for 15 min. to separate the aqueous and organic phases. An aliquot of the aqueous phase, containing [$^3$H]-ethanolamine was withdrawn and counted by scintillation spectroscopy. Data were expressed as the percentage of [$^3$H]-ethanolamine formed versus vehicle, after subtraction of the background radioactivity determined in the presence of 10 μM arachidonyl trifluoromethyl ketone (ATFMK), an inhibitor of FAAH. $IC_{50}$ values were determined using a four-parameter logistic equation for dose-response curves. Compounds for which $IC_{50}$ values are not provided herein showed no FAAH inhibition or marginal FAAH inhibition in preliminary tests.

* A<10 nM; B 10 nM<100 nM; C 100 nM<1,000 nM; D 1,000 nM<10,000 nM

| Example No. | $IC_{50}$ (nM)* |
|---|---|
| 1 | A |
| 2 | D |
| 3 | D |
| 5 | D |
| 6 | B |
| 8 | C |
| 9 | A |
| 10 | A |
| 11 | A |
| 12 | A |
| 13 | B |
| 14 | A |
| 15 | B |
| 16 | C |
| 17 | C |
| 18 | C |
| 19 | B |
| 20 | A |
| 21 | B |
| 22 | A |
| 23 | B |
| 24 | A |
| 25 | B |
| 26 | B |
| 27 | A |
| 28 | C |
| 29 | B |
| 30 | C |
| 31 | B |
| 32 | B |
| 33 | B |
| 34 | B |
| 35 | B |
| 36 | B |
| 37 | C |
| 38 | B |
| 39 | D |
| 40 | C |
| 41 | A |
| 43 | A |

-continued

| Example No. | $IC_{50}$ (nM)* |
|---|---|
| 44 | B |
| 45 | C |
| 46 | B |
| 47 | B |
| 48 | B |
| 49 | B |
| 50 | B |
| 51 | B |
| 52 | D |
| 53 | D |
| 55 | C |
| 56 | C |
| 57 | C |
| 59 | C |
| 60 | D |
| 61 | D |
| 62 | D |
| 63 | D |
| 64 | D |
| 66 | D |
| 69 | D |
| 70 | D |
| 71 | A |
| 72 | B |
| 73 | C |
| 74 | C |

In vivo results

In FIG. 1., example 1, was active in phase I (acute phase) and phase II (chronic phase) of the rat formalin test. In animals that received 25 mg/kg, i.v, of Example 1, the number of paw flinches was reduced by nearly 40% in the first 10 minutes after administration of formalin. Paw flinches were reduced by approximately 30% over the following 50 minutes. The effect of example 1 was similar to that seen with a 3 mg/kg, i.p. dose of morphine.

Figure 2:
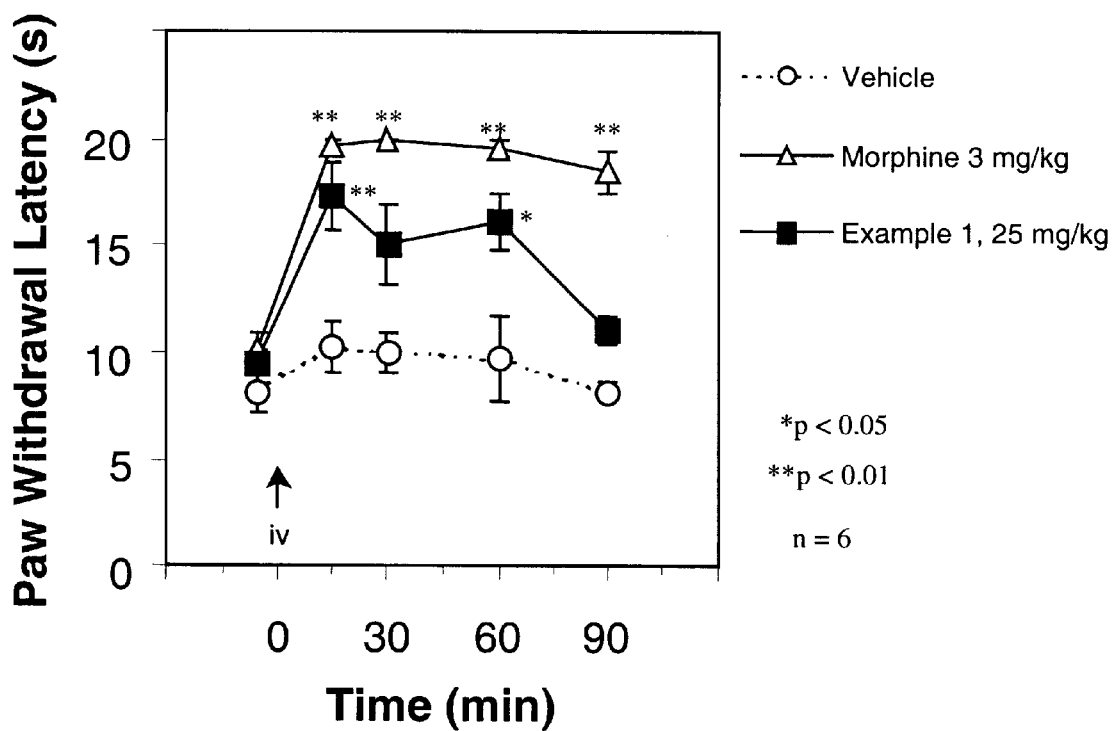
FIG. 2 illustrates results from the Hargreaves Test used for measuring acute thermal pain. The single asterisk (*) applies when p is less than 0.5 whereas the double asterisk (**) applies when p is less than 0.01. n=6.

In FIG. 2., animals that received Example 1, the latency to paw withdrawal was increased significantly. The present results confirm, the activity of Example 1 against acute pain.

Figure 3:
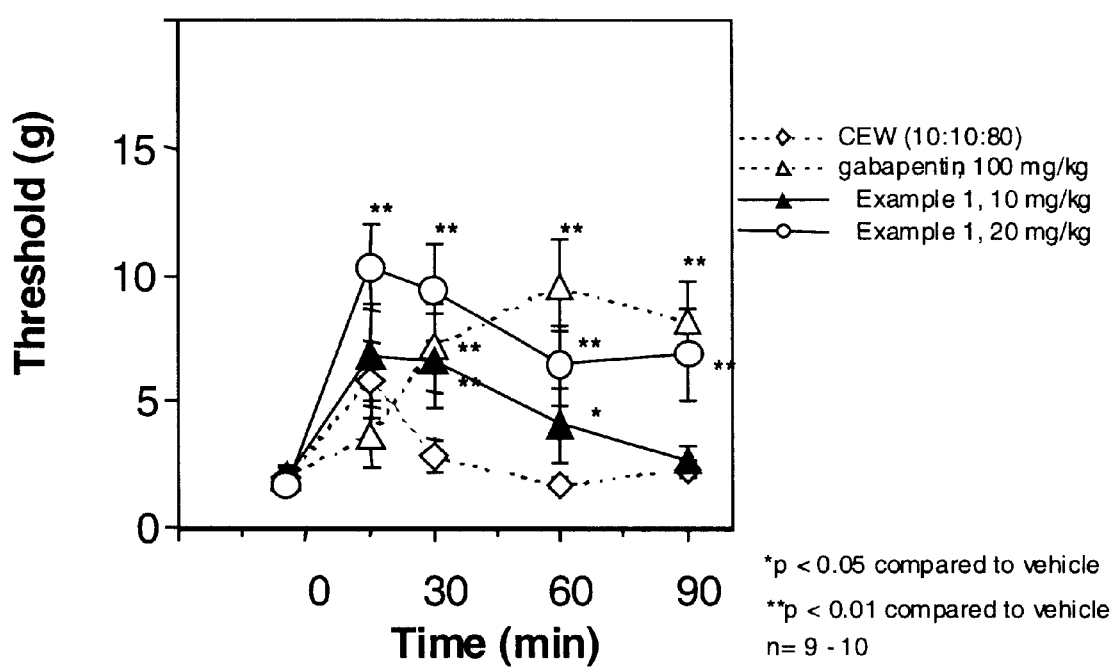
FIG. 3. illustrates results from the Chung Model used for measuring neuropathic pain. The single asterisk (*) applies when p is less than 0.05 whereas the double asterisk (**) applies when p is less than 0.01. n=9–10.

In FIG. 3., Example 1 was examined in the Chung model of neuropathic pain where animals exhibit a pain response (paw withdrawal) to a normally innocuous stimulus (light touch), In animals with a neuropathic injury, the threshold for withdrawal of the injured paw was increased (toward normal) in a dose-dependent fashion by Example 1. The anti-neuropathic effect observed with 20 mg/kg Example 1 exhibited earlier onset of action compared to 100 mg/kg gabapentin (reference compound) with similar peak efficacy.

What is claimed is:

1. Compounds of Formula (I)

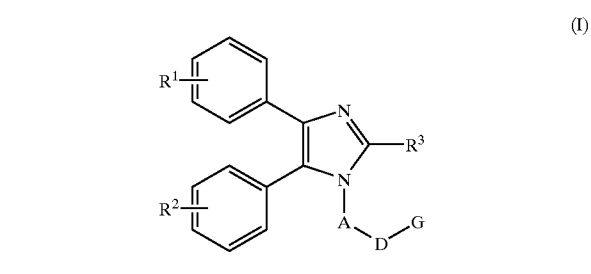

(I)

and pharmaceutically acceptable salts and solvates thereof wherein $R^1$ are $R^2$ are each independently H, $C_{1-3}$ alkyl or halo;
$R^3$ is $C_1$–$C_3$alkyl or $C_{3-7}$cycloalkyl;
A is L;
    L is -phenyl-O—$C_{1-4}$alkylene wherein said $C_{1-4}$alkylene is attached to D;

provided that if A is L, then D is X(O)O and A—D is not interrupted with J—J', —Z-phenyl- or —Z—C$_{1-3}$alkylene;

D is X(O)O, X(O)N(G'), HYC(O)O or HYC(O)ON═C(G');

X is C and is attached to A;

Y is N and is attached to A;

G is H, C$_{1-5}$alkyl, C$_{1-5}$haloalkyl, C$_{3-7}$cycloalkyl, phenyl, —C$_{1-2}$alkylene-phenyl, C-pyridyl or N-pyridyl, said phenyl or —C$_{1-2}$alkylene-phenyl are each optionally and independently substituted with one or more of the same or different substitutents selected from the group consisting of halo, NO$_2$, CN, —C(O)O—C$_{1-3}$-alkyl, C$_{1-3}$alkyl, hydroxy and C$_{1-3}$alkoxy;

G' is H, C$_{1-5}$alkyl or C$_{1-5}$haloalkyl; and wherein A—D is optionally interrupted with J—J', —Z-phenyl- or —Z—C$_{1-3}$alkylene;

wherein

Z is O or S and is attached to A;

J is CH and is attached to A, D and J';

J' is C$_{1-4}$alkyl or phenyl;

provided that if A—D is interrupted with —Z-phenyl-, then A is C$_{1-5}$ alkylene;

if A—D is not interrupted with —Z-phenyl-, then A is C$_{5-12}$ alkylene.

2. Compounds of Formula (I)

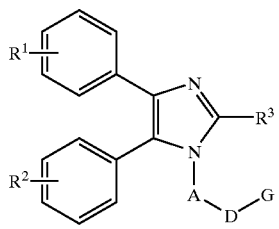

(I)

and pharmaceutically acceptable salts and solvates thereof wherein

R$^1$ are R$^2$ are each independently H; C$_{1-3}$alkyl or halo;

R$^3$ is C$_1$-C$_3$alkyl or C$_{3-7}$cycloalkyl;

A is C$_{1-12}$alkylene or L;

L is -phenyl-O—C$_{1-4}$alkylene wherein said C$_{1-4}$alkylene is attached to D;

provided that if A is L, then D is X(O)O and A—D is not interrupted with J—J', —Z-phenyl- or —Z—C$_{1-3}$alkylene;

D is HYC(O)O;

X is C and is attached to A;

Y is N and is attached to A;

G is H, C$_{1-5}$alkyl, C$_{1-5}$haloalkyl, C$_{3-7}$cycloalkyl, phenyl, —C$_{1-2}$alkylene-phenyl, C-pyridyl or N-pyridyl, said phenyl or —C$_{1-2}$alkylene-phenyl are each optionally and independently substituted with one or more of the same or different substitutents selected from the group consisting of halo, NO$_2$, CN, —C(O)O—C$_{1-3}$-alkyl, C$_{1-3}$alkyl, hydroxy and C$_{1-3}$alkoxy;

G' is H, C$_{1-5}$alkyl or C$_{1-5}$haloalkyl; and wherein A—D is optionally interrupted with J—J', —Z-phenyl- or —Z—C$_{1-3}$alkylene;

wherein

Z is O or S and is attached to A;

J is CH and is attached to A, D and J';

J' is C$_{1-4}$alkyl or phenyl;

provided that if A—D is interrupted with —Z-phenyl-, then A is C$_{1-5}$ alkylene;

if A—D is not interrupted with —Z-phenyl-, then A is C$_{5-12}$ alkylene.

3. Compounds of Formula (I)

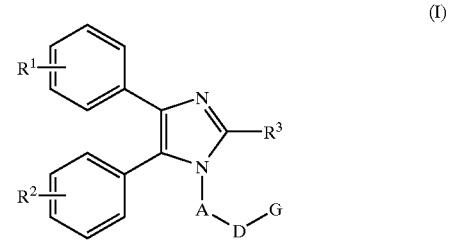

(I)

and pharmaceutically acceptable salts and solvates thereof wherein

R$^1$ are R$^2$ are each independently H; C$_{1-3}$alkyl or halo;

R$^3$ is C$_1$-C$_3$alkyl or C$_{3-7}$cycloalkyl;

A is C$_{1-12}$alkylene or L;

L is -phenyl-O—C$_{1-4}$alkylene wherein said C$_{1-4}$alkylene is attached to D;

provided that if A is L, then D is X(O)O and A—D is not interrupted with J—J', —Z-phenyl- or —Z—C$_{1-3}$alkylene;

D is HYC(O)ON═C(G');

X is C and is attached to A;

Y is N and is attached to A;

G is H, C$_{1-5}$alkyl, C$_{1-5}$haloalkyl, C$_{3-7}$cycloalkyl, phenyl, —C$_{1-2}$alkylene-phenyl, C-pyridyl or N-pyridyl, said phenyl or —C$_{1-2}$alkylene-phenyl are each optionally and independently substituted with one or more of the same or different substitutents selected from the group consisting of halo, NO$_2$, CN, —C(O)O—C$_{1-3}$-alkyl, C$_{1-3}$alkyl, hydroxy and C$_{1-3}$alkoxy;

G' is H, C$_{1-5}$alkyl or C$_{1-5}$haloalkyl; and wherein A—D is optionally interrupted with J—J', —Z-phenyl- or —Z—C$_{1-3}$alkylene;

wherein

Z is O or S and is attached to A;

J is CH and is attached to A, D and J';

J' is C$_{1-4}$alkyl or phenyl;

provided that if A—D is interrupted with —Z-phenyl-, then A is C$_{1-5}$ alkylene;

if A—D is not interrupted with —Z-phenyl-, then A is C$_{5-12}$ alkylene.

4. Compounds of Formula (I)

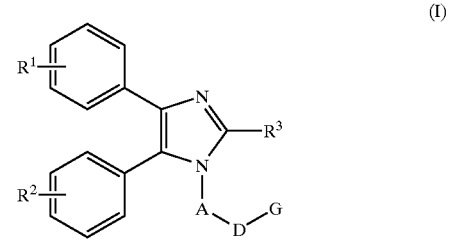

(I)

and pharmaceutically acceptable salts and solvates thereof wherein

R¹ are R² are each independently H, $C_{1-3}$alkyl or halo;
R³ is $C_1$–$C_3$alkyl or $C_{3-7}$cycloalkyl;
A is $C_{1-12}$alkylene or L;
  L is -phenyl-O—$C_{1-4}$alkylene wherein said $C_{1-4}$alkylene is attached to D;
  provided that if A is L, then D is X(O)O and A—D is not interrupted with J—J', —Z-phenyl- or —Z—$C_{1-3}$alkylene;
D is X(O)O, X(O)N(G'), HYC(O)O or HYC(O)ON=C(G');
  X is C and is attached to A;
  Y is N and is attached to A;
G is $C_{3-7}$cycloalkyl; and
wherein A—D is optionally interrupted with J—J', —Z-phenyl- or —Z—$C_{1-3}$alkylene;
  wherein
  Z is O or S and is attached to A;
  J is CH and is attached to A, D and J';
  J' is $C_{1-4}$alkyl or phenyl;
provided that
  if A—D is interrpted with —Z-phenyl-, then A is $C_{1-5}$ alkylene;
  if A—D is not interrpted with —Z-phenyl-, then A is $C_{5-12}$ alkylene.

5. Compounds of Formula (I)

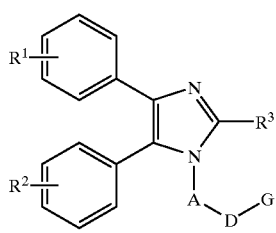

(I)

and pharmaceutically acceptable salts and solvates thereof
wherein
R¹ are R² are each independently H, $C_{1-3}$alkyl or halo;
R³ is $C_1$–$C_3$alkyl or $C_{3-7}$cycloalkyl;
A is $C_{1-12}$alkylene or L;
  L is -phenyl-O—$C_{1-4}$alkylene wherein said $C_{1-4}$alkylene is attached to D;
  provided that if A is L, then D is X(O)O and A—D is not interrupted with J—J', —Z-phenyl- or —Z—$C_{1-3}$alkylene;
D is X(O)O, X(O)N(G'), HYC(O)O or HYC(O)ON=C(G');
  X is C and is attached to A;
  Y is N and is attached to A;
G is —$C_{1-2}$alkylene-phenyl said —$C_{1-2}$alkylene-phenyl is optionally substituted with one or more of the same or different substitutents selected from the group consisting of halo, $NO_2$, CN, —C(O)O—$C_{1-3}$-alkyl, $C_{1-3}$alkyl, hydroxy and $C_{1-3}$alkoxy;
G' is H, $C_{1-5}$alkyl or $C_{1-5}$haloalkyl; and
wherein A—D is optionally interrupted with J—J', —Z-phenyl- or —Z—$C_{1-3}$alkylene;
  wherein
  Z is O or S and is attached to A;
  J is CH and is attached to A, D and J';
  J' is $C_{1-4}$alkyl or phenyl;
provided that
  if A—D is interrpted with —Z-phenyl-, then A is $C_{1-5}$ alkylene;
  if A—D is not interrpted with —Z-phenyl-, then A is $C_{5-12}$ alkylene.

6. Compounds of Formula (I)

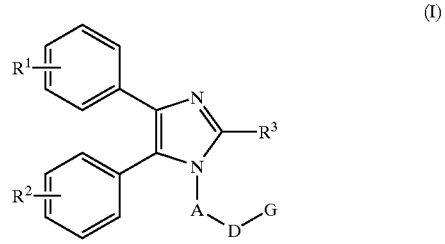

(I)

and pharmaceutically acceptable salts and solvates thereof
wherein
R¹ are R² are each independently H, $C_{1-3}$alkyl or halo;
R³ is $C_1$–$C_3$alkyl or $C_{3-7}$cycloalkyl;
A is $C_{1-12}$alkylene or L;
  L is -phenyl-O—$C_{1-4}$alkylene wherein said $C_{1-4}$alkylene is attached to D;
  provided that if A is L, then D is X(O)O and A—D is not interrupted with J—J', —Z-phenyl- or —Z—$C_{1-3}$alkylene;
D is X(O)O, X(O)N(G'), HYC(O)O or HYC(O)ON=C(G');
  X is C and is attached to A;
  Y is N and is attached to A;
G is phenyl or —$C_{1-2}$alkylene-phenyl, said phenyl or phenyl of said —$C_{1-2}$alkylene-phenyl are optionally substituted with the same or different substitutents selected from the group consisting of halo, CN, —C(O)O—$C_{1-3}$-alkyl, $C_{1-3}$alkyl and $C_{1-3}$alkoxy;
G' is H, $C_{1-5}$alkyl or $C_{1-5}$haloalkyl; and
wherein A—D is optionally interrupted with J—J', —Z-phenyl- or —Z—$C_{1-3}$alkylene;
  wherein
  Z is O or S and is attached to A;
  J is CH and is attached to A, D and J';
  J' is $C_{1-4}$alkyl or phenyl;
provided that
  if A—D is interrpted with —Z-phenyl-, then A is $C_{1-5}$ alkylene;
  if A—D is not interrpted with —Z-phenyl-, then A is $C_{5-12}$ alkylene.

7. Compounds of Formula (I)

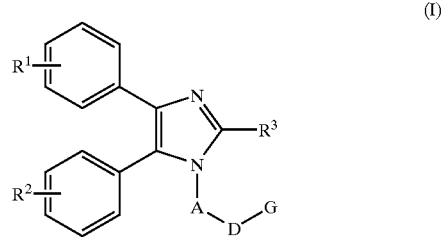

(I)

and pharmaceutically acceptable salts and solvates thereof
wherein
R¹ are R² are each independently H, $C_{1-3}$alkyl or halo;
R³ is $C_1$–$C_3$alkyl or $C_{3-7}$cycloalkyl;
A is $C_{1-12}$alkylene or L;
  L is -phenyl-O—$C_{1-4}$alkylene wherein said $C_{1-4}$alkylene is attached to D;

provided that if A is L, then D is X(O)O and A—D is not interrupted with J—J', —Z-phenyl- or —Z—C$_{1-3}$alkylene;

D is X(O)O, X(O)N(G'), HYC(O)O or HYC(O)ON=C(G');

X is C and is attached to A;

Y is N and is attached to A;

G is phenyl or —C$_{1-2}$alkylene-phenyl, said phenyl or phenyl of said —C$_{1-2}$alkylene-phenyl are substituted with halo, —C(O)O—C$_{1-3}$-alkyl, C$_{1-3}$alkyl or C$_{1-3}$alkoxy;

G' is H, C$_{1-5}$alkyl or C$_{1-5}$haloalkyl; and wherein A—D is optionally interrupted with J—J', —Z-phenyl- or —Z—C$_{1-3}$alkylene;

wherein

Z is O or S and is attached to A;

J is CH and is attached to A, D and J';

J' is C$_{1-4}$alkyl or phenyl;

provided that if A—D is interrpted with —Z-phenyl-, then A is C$_{1-5}$ alkylene;

if A—D is not interrpted with —Z-phenyl-, then A is C$_{5-12}$ alkylene.

8. Compounds of Formula (I)

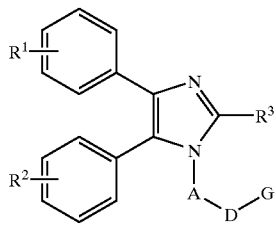

and pharmaceutically acceptable salts and solvates thereof wherein

R$^1$ are R$^2$ are each independently H, C$_{1-3}$alkyl or halo;

R$^3$ is C$_1$–C$_3$alkyl or C$_{3-7}$cycloalkyl;

A is C$_{1-12}$alkylene or L;

L is -phenyl-O—C$_{1-4}$alkylene wherein said C$_{1-4}$alkylene is attached to D;

provided that if A is L, then D is X(O)O and A—D is not interrupted with J—J', —Z-phenyl- or —Z—C$_{1-3}$ alkylene;

D is X(O)O, X(O)N(G'), HYC(O)O or HYC(O)ON=C(G');

X is C and is attached to A;

Y is N and is attached to A;

G is phenyl or —C$_{1-2}$alkylene-phenyl, said phenyl or phenyl of said —C$_{1-2}$alkylene-phenyl are substituted with fluoro;

G' is H, C$_{1-5}$alkyl or C$_{1-5}$haloalkyl; and wherein A—D is optionally interrupted with J—J', —Z-phenyl- or —Z—C$_{1-3}$alkylene;

wherein

Z is O or S and is attached to A;

J is CH and is attached to A, D and J';

J' is C$_{1-4}$alkyl or phenyl;

provided that if A—D is interrpted with —Z-phenyl-, then A is C$_{1-5}$ alkylene;

if A—D is not interrpted with —Z-phenyl-, then A is C$_{5-12}$ alkylene.

9. Compounds of Formula (I)

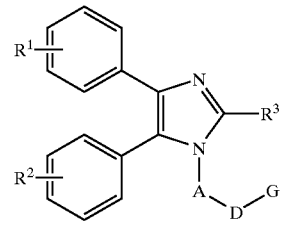

and pharmaceutically acceptable salts and solvates thereof wherein

R$^1$ are R$^2$ are each independently H, C$_{1-3}$alkyl or halo;

R$^3$ is C$_1$–C$_3$alkyl or C$_{3-7}$cycloalkyl;

A is C$_{1-12}$alkylene or L;

L is -phenyl-O—C$_{1-4}$alkylene wherein said C$_{1-4}$alkylene is attached to D;

provided that if A is L, then D is X(O)O and A—D is not interrupted with J—J', —Z-phenyl- or —Z—C$_{1-3}$ alkylene;

D is X(O)O, X(O)N(G'), HYC(O)O or HYC(O)ON=C(G');

X is C and is attached to A;

Y is N and is attached to A;

G is phenyl or —C$_{1-2}$alkylene-phenyl, said phenyl or phenyl of said —C$_{1-2}$alkylene-phenyl are substituted with cyano;

G' is H, C$_{1-5}$alkyl or C$_{1-5}$haloalkyl; and wherein A—D is optionally interrupted with J—J', —Z-phenyl- or —Z—C$_{1-3}$alkylene;

wherein

Z is O or S and is attached to A;

J is CH and is attached to A, D and J';

J' is C$_{1-4}$alkyl or phenyl;

provided that if A—D is interrpted with —Z-phenyl-, then A is C$_{1-5}$ alkylene;

if A—D is not interrpted with —Z-phenyl-, then A is C$_{5-12}$ alkylene.

10. Compounds of Formula (I)

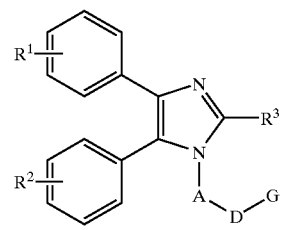

and pharmaceutically acceptable salts and solvates thereof wherein

R$^1$ are R$^2$ are each H;

R$^3$ is C$_1$–C$_3$alkyl;

A is C$_{7-10}$alkylene;

D is HYC(O)O;

Y is N and is attached to A;

G is H, C$_{1-5}$alkyl, C$_{1-5}$haloalkyl, C$_{3-7}$cycloalkyl, phenyl, —C$_{1-2}$alkylene-phenyl, C-pyridyl or N-pyridyl, said phenyl or —C$_{1-2}$alkylene-phenyl are each optionally and independently substituted with one or more of the same or different substitutents selected from the group consisting of halo, NO$_2$, CN, —C(O)O—C$_{1-3}$-alkyl, C$_{1-3}$alkyl, hydroxy and C$_{1-3}$alkoxy; and G' is H, C$_{1-5}$alkyl or C$_{1-5}$haloalkyl.

11. Compounds of Formula (I)

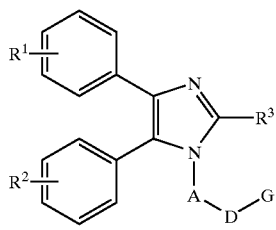

(I)

and pharmaceutically acceptable salts and solvates thereof wherein

R$^1$ are R$^2$ are each H;
R$^3$ is C$_1$–C$_3$alkyl;
A is C$_{1-5}$alkylene;
D is HYC(O)O;
Y is N and is attached to A;
G is H, C$_{1-5}$alkyl, C$_{1-5}$haloalkyl, C$_{3-7}$cycloalkyl, phenyl, —C$_{1-2}$alkylene-phenyl, C-pyridyl or N-pyridyl, said phenyl or —C$_{1-2}$alkylene-phenyl are each optionally and independently substituted with one or more of the same or different substitutents selected from the group consisting of halo, NO$_2$, CN, —C(O)O—C$_{1-3}$-alkyl, C$_{1-3}$alkyl, hydroxy and C$_{1-3}$alkoxy;
G' is H, C$_{1-5}$alkyl or C$_{1-5}$haloalkyl; and
wherein A—D is interrupted with J—J', —Z-phenyl- or —Z—C$_{1-3}$alkylene;
wherein
Z is O or S and is attached to A;
is CH and is attached to A, D and J';
J' is C$_{1-4}$alkyl or phenyl;
provided that
if A—D is interrpted with —Z-phenyl-, then A is C$_{1-5}$ alkylene;
if A—D is not interrpted with —Z-phenyl-, then A is C$_{5-12}$ alkylene.

12. Compounds of Formula (I)

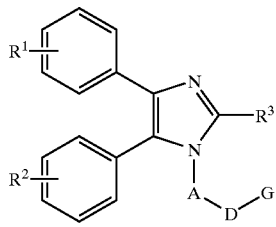

(I)

and pharmaceutically acceptable salts and solvates thereof wherein

R$^1$ are R$^2$ are each H;
R$^3$ is C$_1$–C$_3$alkyl;
A is C$_{7-10}$alkylene;
D is HYC(O)ON=C(G');
Y is N and is attached to A;
G is H, C$_{1-5}$alkyl, C$_{1-5}$haloalkyl, C$_{3-7}$cycloalkyl, phenyl, —C$_{1-2}$alkylene-phenyl, C-pyridyl or N-pyridyl, said phenyl or —C$_{1-2}$alkylene-phenyl are each optionally and independently substituted with one or more of the same or different substitutents selected from the group consisting of halo, NO$_2$, CN, —C(O)O—C$_{1-3}$-alkyl, C$_{1-3}$alkyl, hydroxy and C$_{1-3}$alkoxy; and G' is H, C$_{1-5}$alkyl or C$_{1-5}$haloalkyl.

13. Compounds of Formula (I)

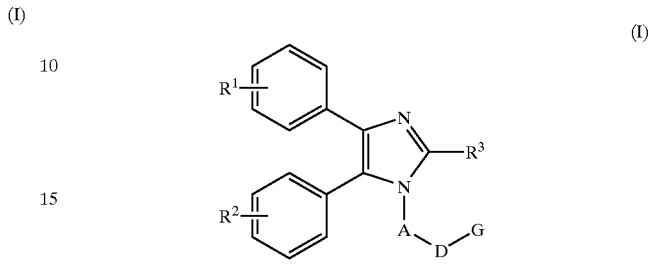

(I)

and pharmaceutically acceptable salts and solvates thereof wherein

R$^1$ are R$^2$ are each H;
R$^3$ is C$_1$–C$_3$alkyl;
A is C$_{1-5}$alkylene;
D is HYC(O)ON=C(G');
Y is N and is attached to A;
G is H, C$_{1-5}$alkyl, C$_{1-5}$haloalkyl, C$_{3-7}$cycloalkyl, phenyl, —C$_{1-2}$alkylene-phenyl, C-pyridyl or N-pyridyl, said phenyl or —C$_{1-2}$alkylene-phenyl are each optionally and independently substituted with one or more of the same or different substitutents selected from the group consisting of halo, NO$_2$, CN, —C(O)O—C$_{1-3}$-alkyl, C$_{1-3}$alkyl, hydroxy and C$_{1-3}$alkoxy;
G' is H, C$_{1-5}$alkyl or C$_{1-5}$haloalkyl; and
wherein A—D is interrupted with J—J', —Z-phenyl- or —Z—C$_{1-3}$alkylene;
wherein
Z is O or S and is attached to A;
J is CH and is attached to A, D and J';
J' is C$_{1-4}$alkyl or phenyl;
provided that
if A—D is interrpted with —Z-phenyl-, then A is C$_{1-5}$ alkylene;
if A—D is not interrpted with —Z-phenyl-, then A is C$_{5-12}$ alkylene.

14. [6-(2-Methyl-4,5-diphenyl-imidazol-1-yl)-hexyl]-carbamic acid 2-fluoro-phenyl ester;
[6-(2-Ethyl-4,5-diphenyl-imidazol-1-yl)-hexyl]-carbamic acid tert-butyl ester;
6-(2-Ethyl-4,5-diphenyl-imidazol-1-yl)-hexyl]-carbamic acid sec-butyl ester;
[6-(2-Methyl-4,5-diphenyl-imidazol-1-yl)-hexyl]-carbamic acid benzyl ester;
2-Propanone,O-[6-(2-methyl-4,5-diphenyl-1H-imidazol-1-yl)hexyl]amino]carbonyl]oxime;
[6-(2-Methyl-4,5-diphenyl-imidazol-1-yl)-hexyl]-carbamic acid methyl ester;
6-(2-Methyl-4,5-diphenyl-imidazol-1-yl)-hexyl]-carbamic acid phenyl ester;
[6-(2-Methyl-4,5-diphenyl-imidazol-1-yl)-hexyl]-carbamic acid 4-fluoro-phenyl ester;
[6-(2-Methyl-4,5-diphenyl-imidazol-1-yl)-hexyl]-carbamic acid 2,4-difluoro-phenyl ester;
[6-(2-Methyl-4,5-diphenyl-imidazol-1-yl)-hexyl]-carbamic acid 4-chloro-phenyl ester;
[6-(2-Methyl-4,5-diphenyl-imidazol-1-yl)-hexyl]-carbamic acid 4-methoxy-phenyl ester;

[6-(2-Methyl-4,5-diphenyl-imidazol-1-yl)-hexyl]-carbamic acid o-tolyl ester;
[6-(2-Methyl-4,5-diphenyl-imidazol-1-yl)-hexyl]-carbamic acid 4-cyano-phenyl ester;
[6-(2-Methyl-4,5-diphenyl-imidazol-1-yl)-hexyl]-carbamic acid 2,6-dimethoxy-phenyl ester;
[6-(2-Methyl-4,5-diphenyl-imidazol-1-yl)-hexyl]-carbamic acid 2-methoxy-phenyl ester;
[7-(2-Methyl-4,5-diphenyl-imidazol-1-yl)-heptyl]-carbamic acid methyl ester;
[7-(2-Methyl-4,5-diphenyl-imidazol-1-yl)-heptyl]-carbamic acid ethyl ester;
[7-(2-Methyl-4,5-diphenyl-imidazol-1-yl)-heptyl]-carbamic acid phenyl ester;
[7-(2-Methyl-4,5-diphenyl-imidazol-1-yl)-heptyl]-carbamic acid 4-fluoro-phenyl ester;
[7-(2-Methyl-4,5-diphenyl-imidazol-1-yl)-heptyl]-carbamic acid 2-fluoro-phenyl ester;
[7-(2-Methyl-4,5-diphenyl-imidazol-1-yl)-heptyl]-carbamic acid 2,4-difluoro-phenyl ester;
[7-(2-Methyl-4,5-diphenyl-imidazol-1-yl)-heptyl]-carbamic acid 4-chloro-phenyl ester;
[7-(2-Methyl-4,5-diphenyl-imidazol-1-yl)-heptyl]-carbamic acid 4-methoxy-phenyl ester;
[7-(2-Methyl-4,5-diphenyl-imidazol-1-yl)-heptyl]-carbamic acid o-tolyl ester;
[7-(2-Methyl-4,5-diphenyl-imidazol-1-yl)-heptyl]-carbamic acid 4-cyano-phenyl ester;
[7-(2-Methyl-4,5-diphenyl-imidazol-1-yl)-heptyl]-carbamic acid 2,6-dimethoxy-phenyl ester;
[7-(2-Methyl-4,5-diphenyl-imidazol-1-yl)-heptyl]-carbamic acid 2-methoxy-phenyl ester;
[5-(2-Methyl-4,5-diphenyl-imidazol-1-yl)-pentyl]-carbamic acid ethyl ester;
[5-(2-Methyl-4,5-diphenyl-imidazol-1-yl)-pentyl]-carbamic acid phenyl ester;
[5-(2-Methyl-4,5-diphenyl-imidazol-1-yl)-pentyl]-carbamic acid 4-fluoro-phenyl ester;
[5-(2-Methyl-4,5-diphenyl-imidazol-1-yl)-pentyl]-carbamic acid 2,4-difluoro-phenyl ester;
[5-(2-Methyl-4,5-diphenyl-imidazol-1-yl)-pentyl]-carbamic acid 2-fluoro-phenyl ester;
[5-(2-Methyl-4,5-diphenyl-imidazol-1-yl)-pentyl]-carbamic acid 4-chloro-phenyl ester;
[5-(2-Methyl-4,5-diphenyl-imidazol-1-yl)-pentyl]-carbamic acid 4-methoxy-phenyl ester;
[5-(2-Methyl-4,5-diphenyl-imidazol-1-yl)-pentyl]-carbamic acid o-tolyl ester;
[5-(2-Methyl-4,5-diphenyl-imidazol-1-yl)-pentyl]-carbamic acid 4-cyano-phenyl ester;
[5-(2-Methyl-4,5-diphenyl-imidazol-1-yl)-pentyl]-carbamic acid 2,6-dimethoxy-phenyl ester;
[5-(2-Methyl-4,5-diphenyl-imidazol-1-yl)-pentyl]-carbamic acid 2-methoxy-phenyl ester;
[6-(2-Methyl-4,5-diphenyl-imidazol-1-yl)-hexyl]-carbamic acid 3,4-difluoro-phenyl ester;
{6-[4,5-Bis-(4-fluoro-phenyl)-2-methyl-imidazol-1-yl]-hexyl}-carbamic acid 2-fluoro-phenyl ester;
{6-[4,5-Bis-(4-fluoro-phenyl)-2-methyl-imidazol-1-yl]-hexyl}-carbamic acid 2,6-difluoro-phenyl ester;
[6-(2-Methyl-4,5-diphenyl-imidazol-1-yl)-hexyl]-carbamic acid ethyl ester;
Benzaldehyde, O-[6-(2-methyl-4,5-diphenyl-1H-imidazol-1-yl)hexyl]amino]carbonyl]oxime;
4-Fluorobenzaldehyde,O-[6-(2-methyl-4,5-diphenyl-1H-imidazol-1-yl)hexyl]amino]carbonyl]oxime;
2-Nitrobenzaldehyde, O-[6-(2-methyl-4,5-diphenyl-1H-imidazol-1yl)hexyl]amino]carbonyl]oxime;
3-Nitrobenzaldehyde, O-[6-(2-methyl-4,5-diphenyl-1H-imidazol-1-yl)hexyl]amino]carbonyl]oxime;
4-Nitrobenzaldehyde, O-[6-(2-methyl-4,5-diphenyl-1H-imidazol-1-yl)hexyl]amino]carbonyl]oxime;
3-Pyridinecarboxaldehyde, O-[6-(2-methyl-4,5-diphenyl-1H-imidazol-1-yl)hexyl]amino]carbonyl]oxime;
4-[2-(2-Methyl-4,5-diphenyl-imidazol-1-yl)-ethoxy]-phenyl-carbamic acid 3,4-difluoro-phenyl ester;
{4-[2-(2-Methyl-4,5-diphenyl-imidazol-1-yl)-ethoxy]-phenyl}-carbamic acid 4-chloro-phenyl ester;
{4-[3-(2-Methyl-4,5-diphenyl-imidazol-1-yl)-propoxy]-phenyl}-carbamic acid 3,4-difluoro-phenyl ester;
{4-[3-(2-Methyl-4,5-diphenyl-imidazol-1-yl)-propoxy]-phenyl}-carbamic acid 4-methoxy-phenyl ester;
{4-[3-(2-Methyl-4,5-diphenyl-imidazol-1-yl)-propoxy]-phenyl}-carbamic acid 4-chloro-phenyl ester;
{4-[3-(2-Methyl-4,5-diphenyl-imidazol-1-yl)-propoxy]-phenyl}-carbamic acid 2-methoxy-phenyl ester;
{4-[3-(2-Methyl-4,5-diphenyl-imidazol-1-yl)-propoxy]-phenyl}-carbamic acid 3-chloro-phenyl ester;
{4-[2-(2-Methyl-4,5-diphenyl-imidazol-1-yl)-ethoxy]-phenyl}-carbamic acid phenyl ester;
{4-[2-(2-Methyl-4,5-diphenyl-imidazol-1-yl)-ethoxy]-phenyl}-carbamic acid 2-fluoro-phenyl ester;
{4-[2-(2-Methyl-4,5-diphenyl-imidazol-1-yl)-ethoxy]-phenyl}-carbamic acid 4-fluoro-phenyl ester;
{4-[3-(2-Methyl-4,5-diphenyl-imidazol-1-yl)-propoxy]-phenyl}-carbamic acid phenyl ester;
{4-[2-(2-Methyl-4,5-diphenyl-imidazol-1-yl)-ethoxy]-phenyl}-carbamic acid 4-methoxy-phenyl ester;
{4-[3-(2-Methyl-4,5-diphenyl-imidazol-1-yl)-propoxy]-phenyl}-carbamic acid 2-fluoro-phenyl ester;
{4-[3-(2-Methyl-4,5-diphenyl-imidazol-1-yl)-propoxy]-phenyl}-carbamic acid 2,6-difluoro-phenyl ester;
{4-[2-(2-Methyl-4,5-diphenyl-imidazol-1-yl)-ethoxy]-phenyl}-carbamic acid ethyl ester;
[1-Methyl-6-(2-methyl-4,5-diphenyl-imidazol-1-yl)-hexyl]-carbamic acid 2-fluoro-phenyl ester;
[1-Ethyl-6-(2-methyl-4,5-diphenyl-imidazol-1-yl)-hexyl]-carbamic acid 2-fluoro-phenyl ester;
[1-Isopropyl-6-(2-methyl-4,5-diphenyl-imidazol-1-yl)-hexyl]-carbamic acid 2-fluoro-phenyl ester or
[6-(2-Methyl-4,5-diphenyl-imidazol-1-yl)-1-phenyl-hexyl]-carbamic acid 2-fluoro-phenyl ester.

15. [6-(2-Methyl-4,5-diphenyl-imidazol-1-yl)-hexyl]-carbamic acid 2-fluoro-phenyl ester;
2-Propanone,O-[6-(2-methyl-4,5-diphenyl-1H-imidazol-1-yl)hexyl]amino]carbonyl]oxime;
[6-(2-Methyl-4,5-diphenyl-imidazol-1-yl)-hexyl]-carbamic acid cyclohexyl ester;
[6-(2-Methyl-4,5-diphenyl-imidazol-1-yl)-hexyl]-carbamic acid methyl ester;
6-(2-Methyl-4,5-diphenyl-imidazol-1-yl)-hexyl]-carbamic acid phenyl ester;
[6-(2-Methyl-4,5-diphenyl-imidazol-1-yl)-hexyl]-carbamic acid 4-fluoro-phenyl ester;
[6-(2-Methyl-4,5-diphenyl-imidazol-1-yl)-hexyl]-carbamic acid 2,4-difluoro-phenyl ester;
[6-(2-Methyl-4,5-diphenyl-imidazol-1-yl)-hexyl]-carbamic acid 4-chloro-phenyl ester;
[6-(2-Methyl-4,5-diphenyl-imidazol-1-yl)-hexyl]-carbamic acid 4-methoxy-phenyl ester;
[6-(2-Methyl-4,5-diphenyl-imidazol-1-yl)-hexyl]-carbamic acid o-tolyl ester;
[6-(2-Methyl-4,5-diphenyl-imidazol-1-yl)-hexyl]-carbamic acid 4-cyano-phenyl ester;
[6-(2-Methyl-4,5-diphenyl-imidazol-1-yl)-hexyl]-carbamic acid 2,6-dimethoxy-phenyl ester;

[6-(2-Methyl-4,5-diphenyl-imidazol-1-yl)-hexyl]-carbamic acid 2-methoxy-phenyl ester;
[7-(2-Methyl-4,5-diphenyl-imidazol-1-yl)-heptyl]-carbamic acid methyl ester;
[7-(2-Methyl-4,5-diphenyl-imidazol-1-yl)-heptyl]-carbamic acid ethyl ester;
[7-(2-Methyl-4,5-diphenyl-imidazol-1-yl)-heptyl]-carbamic acid phenyl ester;
[7-(2-Methyl-4,5-diphenyl-imidazol-1-yl)-heptyl]-carbamic acid 4-fluoro-phenyl ester;
[7-(2-Methyl-4,5-diphenyl-imidazol-1-yl)-heptyl]-carbamic acid 2-fluoro-phenyl ester;
[7-(2-Methyl-4,5-diphenyl-imidazol-1-yl)-heptyl]-carbamic acid 2,4-difluoro-phenyl ester;
[7-(2-Methyl-4,5-diphenyl-imidazol-1-yl)-heptyl]-carbamic acid 4-chloro-phenyl ester;
[7-(2-Methyl-4,5-diphenyl-imidazol-1-yl)-heptyl]-carbamic acid 4-methoxy-phenyl ester;
[7-(2-Methyl-4,5-diphenyl-imidazol-1-yl)-heptyl]-carbamic acid o-tolyl ester;
[7-(2-Methyl-4,5-diphenyl-imidazol-1-yl)-heptyl]-carbamic acid 4-cyano-phenyl ester;
[7-(2-Methyl-4,5-diphenyl-imidazol-1-yl)-heptyl]-carbamic acid 2,6-dimethoxy-phenyl ester;
[7-(2-Methyl-4,5-diphenyl-imidazol-1-yl)-heptyl]-carbamic acid 2-methoxy-phenyl ester;
[5-(2-Methyl-4,5-diphenyl-imidazol-1-yl)-penty]-carbamic acid ethyl ester;
[5-(2-Methyl-4,5-diphenyl-imidazol-1-yl)-pentyl]-carbamic acid phenyl ester;
[5-(2-Methyl-4,5-diphenyl-imidazol-1-yl)-pentyl]-carbamic acid 4-fluoro-phenyl ester;
[5-(2-Methyl-4,5-diphenyl-imidazol-1-yl)-pentyl]-carbamic acid 2,4-difluoro-phenyl ester;
[5-(2-Methyl-4,5-diphenyl-imidazol-1-yl)-pentyl]-carbamic acid 2-fluoro-phenyl ester;
[5-(2-Methyl-4,5-diphenyl-imidazol-1-yl)-pentyl]-carbamic acid 4-chloro-phenyl ester;
[5-(2-Methyl-4,5-diphenyl-imidazol-1-yl)-pentyl]-carbamic acid 4-methoxy-phenyl ester;
[5-(2-Methyl-4,5-diphenyl-imidazol-1-yl)-pentyl]-carbamic acid o-tolyl ester;
[5-(2-Methyl-4,5-diphenyl-imidazol-1-yl)-pentyl]-carbamic acid 4-cyano-phenyl ester;
[5-(2-Methyl-4,5-diphenyl-imidazol-1-yl)-pentyl]-carbamic acid 2-methoxy-phenyl ester;
[6-(2-Methyl-4,5-diphenyl-imidazol-1-yl)-hexyl]-carbamic acid 3,4-difluoro-phenyl ester;
[6-(2-Methyl-4,5-diphenyl-imidazol-1-yl)-hexyl]-carbamic acid isopropyl ester;
{6-[4,5-Bis-(4-fluoro-phenyl)-2-methyl-imidazol-1-yl]-hexyl}-carbamic acid 2-fluoro-phenyl ester;
{6-[4,5-Bis-(4-fluoro-phenyl)-2-methyl-imidazol-1-yl]-hexyl}-carbamic acid 2,6-difluoro phenyl ester;
[6-(2-Methyl-4,5-diphenyl-imidazol-1-yl)-hexyl]-carbamic acid ethyl ester;
Benzaldehyde, O-[6-(2-methyl-4,5-diphenyl-1H-imidazol-1-yl)hexyl]amino]carbonyl]oxime;
4-Fluorobenzaldehyde, O-[6-(2-methyl-4,5-diphenyl-1H-imidazol-1-yl)hexyl]amino]carbonyl]oxime;
2-Nitrobenzaldehyde, O-[6-(2-methyl-4,5-diphenyl-1H-imidazol-1-yl)hexyl]amino]carbonyl]oxime;
3-Nitrobenzaldehyde, O-[6-(2-methyl-4,5-diphenyl-1H-imidazol-1-yl)hexyl]amino]carbonyl]oxime;
4-Nitrobenzaldehyde, O-[6-(2-methyl-4,5-diphenyl-1H-imidazol-1-yl)hexyl]amino]carbonyl]oxime;
3-Pyridinecarboxaldehyde, O-[6-(2-methyl-4,5-diphenyl-1H-imidazol-1-yl)hexyl]amino]carbonyl]oxime;
{4-[3-(2-Methyl-4,5-diphenyl-imidazol-1-yl)-propoxy]-phenyl}-carbamic acid 3,4-difluoro-phenyl ester;
{4-[3-(2-Methyl-4,5-diphenyl-imidazol-1-yl)-propoxy]-phenyl}-carbamic acid 4-methoxy-phenyl ester;
{4-[3-(2-Methyl-4,5-diphenyl-imidazol-1-yl)-propoxy]-phenyl}-carbamic acid 4-chloro-phenyl ester;
{4-[3-(2-Methyl-4,5-diphenyl-imidazol-1-yl)-propoxy]-phenyl}-carbamic acid 2-methoxy-phenyl ester;
{4-[3-(2-Methyl-4,5-diphenyl-imidazol-1-yl)-propoxy]-phenyl}-carbamic acid 3-chloro-phenyl ester;
[1-Methyl-6-(2-methyl-4,5-diphenyl-imidazol-1-yl)-hexyl]-carbamic acid 2-fluoro-phenyl ester;
[1-Ethyl-6-(2-methyl-4,5-diphenyl-imidazol-1-yl)-hexyl]-carbamic acid 2-fluoro-phenyl ester;
[1-Isopropyl-6-(2-methyl-4,5-diphenyl-imidazol-1-yl)-hexyl]-carbamic acid 2-fluoro-phenyl ester; or
[6-(2-Methyl-4,5-diphenyl-imidazol-1-yl)-1-phenyl-hexyl]-carbamic acid 2-fluoro-phenyl ester.

16. [6-(2-Methyl-4,5-diphenyl-imidazol-1-yl)-hexyl]-carbamic acid 2-fluoro-phenyl ester;
2-Propanone,O-[6-(2-methyl-4,5-diphenyl-1H-imidazol-1-yl)hexyl]amino]carbonyl]oxime;
6-(2-Methyl-4,5-diphenyl-imidazol-1-yl)-hexyl]-carbamic acid phenyl ester;
[6-(2-Methyl-4,5-diphenyl-imidazol-1-yl)-hexyl]-carbamic acid 4-fluoro-phenyl ester;
[6-(2-Methyl-4,5-diphenyl-imidazol-1-yl)-hexyl]-carbamic acid 2,4-difluoro-phenyl ester;
[6-(2-Methyl-4,5-diphenyl-imidazol-1-yl)-hexyl]-carbamic acid 4-chloro-phenyl ester;
[6-(2-Methyl-4,5-diphenyl-imidazol-1-yl)-hexyl]-carbamic acid 4-methoxy-phenyl ester;
[6-(2-Methyl-4,5-diphenyl-imidazol-1-yl)-hexyl]-carbamic acid o-tolyl ester;
[6-(2-Methyl-4,5-diphenyl-imidazol-1-yl)-hexyl]-carbamic acid 4-cyano-phenyl ester;
[7-(2-Methyl-4,5-diphenyl-imidazol-1-yl)-heptyl]-carbamic acid ethyl ester;
[7-(2-Methyl-4,5-diphenyl-imidazol-1-yl)-heptyl]-carbamic acid phenyl ester;
[7-(2-Methyl-4,5-diphenyl-imidazol-1-yl)-heptyl]-carbamic acid 4-fluoro-phenyl ester;
[7-(2-Methyl-4,5-diphenyl-imidazol-1-yl)-heptyl]-carbamic acid 2-fluoro-phenyl ester;
[7-(2-Methyl-4,5-diphenyl-imidazol-1-yl)-heptyl]-carbamic acid 2,4-difluoro-phenyl ester;
[7-(2-Methyl-4,5-diphenyl-imidazol-1-yl)-heptyl]-carbamic acid 4-chloro-phenyl ester;
[7-(2-Methyl-4,5-diphenyl-imidazol-1-yl)-heptyl]-carbamic acid 4-methoxy-phenyl ester;
[7-(2-Methyl-4,5-diphenyl-imidazol-1-yl)-heptyl]-carbamic acid o-tolyl ester;
[7-(2-Methyl-4,5-diphenyl-imidazol-1-yl)-heptyl]-carbamic acid 4-cyano-phenyl ester;
[7-(2-Methyl-4,5-diphenyl-imidazol-1-yl)-heptyl]-carbamic acid 2-methoxy-phenyl ester;
[5-(2-Methyl-4,5-diphenyl-imidazol-1-yl)-pentyl]-carbamic acid phenyl ester;
[5-(2-Methyl-4,5-diphenyl-imidazol-1-yl)-pentyl]-carbamic acid 4-fluoro-phenyl ester;
[5-(2-Methyl-4,5-diphenyl-imidazol-1-yl)-pentyl]-carbamic acid 2,4-difluoro-phenyl ester;
[5-(2-Methyl-4,5-diphenyl-imidazol-1-yl)-pentyl]-carbamic acid 2-fluoro-phenyl ester;
[5-(2-Methyl-4,5-diphenyl-imidazol-1-yl)-pentyl]-carbamic acid 4-chloro-phenyl ester;
[5-(2-Methyl-4,5-diphenyl-imidazol-1-yl)-pentyl]-carbamic acid 4-methoxy-phenyl ester;

[5-(2-Methyl-4,5-diphenyl-imidazol-1-yl)-pentyl]-carbamic acid 4-cyano-phenyl ester;
[5-(2-Methyl-4,5-diphenyl-imidazol-1-yl)-pentyl]-carbamic acid 2,6-dimethoxy-phenyl ester;
[6-(2-Methyl-4,5-diphenyl-imidazol-1-yl)-hexyl]-carbamic acid 3,4-difluoro-phenyl ester;
{6-[4,5-Bis-(4-fluoro-phenyl)-2-methyl-imidazol-1-yl]-hexyl}-carbamic acid 2-fluoro-phenyl ester;
{6-[4,5-Bis-(4-fluoro-phenyl)-2-methyl-imidazol-1-yl]-hexyl}-carbamic acid 2,6-difluoro-phenyl ester;
Benzaldehyde, O-[6-(2-methyl-4,5-diphenyl-1H-imidazol-1-yl)hexyl]amino]carbonyl]oxime;
4-Fluorobenzaldehyde,O-[6-(2-methyl-4,5-diphenyl-1H-imidazol-1-yl)hexyl]amino]carbonyl]oxime;
2-Nitrobenzaldehyde, O-[6-(2-methyl-4,5-diphenyl-1H-imidazol-1-yl)hexyl]amino]carbonyl]oxime;
3-Nitrobenzaldehyde, O-[6-(2-methyl-4,5-diphenyl-1H-imidazol-1-yl)hexyl]amino]carbonyl]oxime;
4-Nitrobenzaldehyde, O-[6-(2-methyl-4,5-diphenyl-1H-imidazol-1-yl)hexyl]amino]carbonyl]oxime;
3-Pyridinecarboxaldehyde, O-[6-(2-methyl-4,5-diphenyl-1H-imidazol-1-yl)hexyl]amino]carbonyl]oxime;
[1-Methyl-6-(2-methyl-4,5-diphenyl-imidazol-1-yl)-hexyl]-carbamic acid 2-fluoro-phenyl ester; or
[1-Ethyl-6-(2-methyl-4,5-diphenyl-imidazol-1-yl)-hexyl]-carbamic acid 2-fluoro-phenyl ester.

17. [6-(2-Methyl-4,5-diphenyl-imidazol-1-yl)-hexyl]-carbamic acid 2-fluoro-phenyl ester;
6-(2-Methyl-4,5-diphenyl-imidazol-1-yl)-hexyl]-carbamic acid phenyl ester;
[6-(2-Methyl-4,5-diphenyl-imidazol-1-yl)-hexyl]-carbamic acid 4-fluoro-phenyl ester;
[6-(2-Methyl-4,5-diphenyl-imidazol-1-yl)-hexyl]-carbamic acid 2,4-difluoro-phenyl ester;
[6-(2-Methyl-4,5-diphenyl-imidazol-1-yl)-hexyl]-carbamic acid 4-chloro-phenyl ester;
[6-(2-Methyl-4,5-diphenyl-imidazol-1-yl)-hexyl]-carbamic acid o-tolyl ester;
[7-(2-Methyl-4,5-diphenyl-imidazol-1-yl)-heptyl]-carbamic acid phenyl ester;
[7-(2-Methyl-4,5-diphenyl-imidazol-1-yl)-heptyl]-carbamic acid 2-fluoro-phenyl ester;
[7-(2-Methyl-4,5-diphenyl-imidazol-1-yl)-heptyl]-carbamic acid 4-chloro-phenyl ester;
[7-(2-Methyl-4,5-diphenyl-imidazol-1-yl)-heptyl]-carbamic acid 4-cyano-phenyl ester;
[6-(2-Methyl-4,5-diphenyl-imidazol-1-yl)-hexyl]-carbamic acid 3,4-difluoro-phenyl ester;
{6-[4,5-Bis-(4-fluoro-phenyl)-2-methyl-imidazol-1-yl]-hexyl}-carbamic acid 2-fluoro-phenyl ester; or
[1-Methyl-6-(2-methyl-4,5-diphenyl-imidazol-1-yl)-hexyl]-carbamic acid 2-fluoro-phenyl ester.

18. A method of treating chronic pain, acute pain or neuropathic pain in a mammal in need thereof by the administration of an effective amount of a pharmaceutical composition comprising a compound according to claims 1, 2, 3 or 4.

19. A method of treating chronic pain, acute pain and neuropathic pain by the administration of a pharmaceutical composition comprising

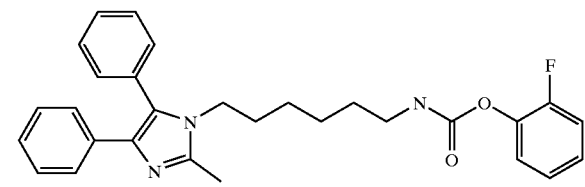

or salt or solvate thereof.

20. A method of treating neuropathic pain by the administration of a pharmaceutical composition comprising

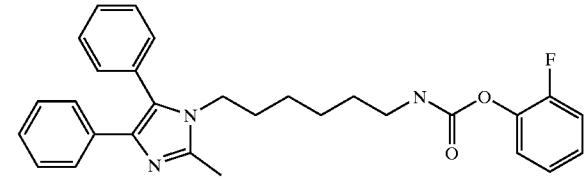

or salt or solvate thereof.

* * * * *